(12) United States Patent
Felix et al.

(10) Patent No.: US 8,642,265 B2
(45) Date of Patent: Feb. 4, 2014

(54) COMPOSITIONS AND METHODS FOR THE DETECTION OF TOPOISOMERASE II COMPLEXES WITH DNA

(75) Inventors: Carolyn A. Felix, Ardmore, PA (US); Donald A Baldwin, Newtown Square, PA (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 533 days.

(21) Appl. No.: 12/487,789

(22) Filed: Jun. 19, 2009

(65) Prior Publication Data

US 2010/0167944 A1 Jul. 1, 2010

Related U.S. Application Data

(62) Division of application No. 11/222,626, filed on Sep. 9, 2005, now abandoned.

(60) Provisional application No. 60/608,331, filed on Sep. 9, 2004.

(51) Int. Cl.
*C12Q 1/68* (2006.01)
*C12P 19/34* (2006.01)

(52) U.S. Cl.
USPC .......................... 435/6.12; 435/6.1; 435/6.11

(58) Field of Classification Search
None
See application file for complete search history.

(56) References Cited

U.S. PATENT DOCUMENTS

| | | | |
|---|---|---|---|
| 6,368,791 B1 * | 4/2002 | Felix et al. | 435/6 |
| 2001/0044137 A1 * | 11/2001 | Heyman et al. | 435/91.1 |
| 2003/0044783 A1 | 3/2003 | Williams et al. | |
| 2003/0096255 A1 | 5/2003 | Felix et al. | |
| 2003/0124542 A1 | 7/2003 | Shah et al. | |
| 2003/0143539 A1 | 7/2003 | Bertucci et al. | |
| 2004/0018513 A1 | 1/2004 | Downing et al. | |
| 2006/0063179 A1 | 3/2006 | Felix et al. | |

FOREIGN PATENT DOCUMENTS

WO 02/058534 11/2001

OTHER PUBLICATIONS

Strissel et al., An In Vivo Topoisomerase II Cleavage Site and a DNase I Hypersensitive Site Colocalize Near Exon 9 in the MLL Breakpoint Cluster Region, Blood, vol. 92, No. 10 (Nov. 15), 1998: pp. 3793-3803.*

Mao et al., p53 Dependence of Topoisomerase I Recruitment in Vivo, Cancer Res 2000;60:4538-4543. Published online Aug. 1, 2000.*

Bojanowski et al., DNA Topoisomerase I1 and Casein Kinase I1 Associate in a Molecular Complex That Is Catalytically Active, The Journal of Biological Chemistry, vol. 268, No. 30, Issue of Oct. 25, pp. 22920-22926, 1993.*

Lund et al., Minimal DNA Requirement for Topoisomerase II-mediated Cleavage in Vitro, Journal of Biological Chemistry, vol. 265, No. 23, Issue of Aug. 15, pp. 1385&13863, 1990.*

Barbaux et al., Use of degenerate oligonucleotide primed PCR (DOP-PCR) for the genotyping of low-concentration DNA samples, J Mol Med (2001) 79:329-332.*

Yamamoto, K., et al., "Two distinct portions of LTG19/ENL at 19p13 are involved in t(11;19) leukemia," Oncogene, 8:2617-2625 (1993).

Wong, W.T., et al., "The human eps15 gene, encoding a tyrosine kinase substrate, is conserved in evolution and maps to 1p31-p32," Oncogene, 9:1591-1597 (1994).

Taki, T., et al., "Fusion of the MLL gene with two different genes, AF-6 and AF-5 alpha, by a complex translocation involving chromosomes 5, 6, 8 and 11 in infant leukemia," Oncogene, 13:2121-2130 (1996).

Sandoval, C., et al., "Secondary acute myeloid leukemia in children previously treated with alkylating agents, intercalating topoisomerase II inhibitors, and irradiation," J. Clin. Oncol., 11(6):1039-1045 (Jun. 1993).

Rowley, J.D., et al., "International workshop on the relationship of prior therapy to balanced chromosome aberrations in therapy-related myelodysplastic syndromes and acute leukemia: overview report," Genes, Chromosomes & Cancer, 33:331-345 (2002).

Rogaia, D., et al., "The localization of the HRX/ALL1 protein to specific nuclear subdomains is altered by fusion with its eps15 translocation partner," Cancer Res., 57:799-802 (Mar. 1, 1997).

Mitterbauer, G., et al., "Monitoring of minimal residual disease in patients with MLL-AF6-positive acute myeloid leukaemia by reverse transcriptase polymerase chain reaction," Br. J. Haematol., 109:622-628 (2000).

Iida, S., et al., "MLLT3 gene on 9p22 involved in t(9;11) leukemia encodes a serine/proline rich protein homologous to MLLT1 on 19p13," Oncogene, 8(11):3085-92 (1993).

Kushner, B.H., et al., "Neuroblastoma and treatment-related myelodysplasia/leukemia: the memorial Sloan-Kettering experience and a literature review," J. Clin. Oncol., 16(12):3880-3889 (Dec. 1998).

Fortune, J.M., et al., "Topoisomerase II as a target for anticancer drugs: when enzymes stop being nice," Progress in Nucleic Acid Res. and Molecular Biol., 64:221-253 (2000).

Felix, C.A., et al., "MLL genomic breakpoint distribution within the breakpoint cluster region in de novo leukemia in children," J. Pediatr. Hematol./Oncol., 20(4):299-308 (Jul./Aug. 1998).

Felix, C.A., "Leukemias related to treatment with DNA topoisomerase II inhibitors," Med. Pediatr. Oncol., 36:525-535 (2001).

(Continued)

*Primary Examiner* — Young J Kim
(74) *Attorney, Agent, or Firm* — Dann, Dorfman, Herrell & Skillman; Robert C. Netter, Jr.

(57) ABSTRACT

Compositions, methods, and kits for detecting DNA topoisomerase II-DNA complexes are disclosed.

19 Claims, 21 Drawing Sheets

(56) References Cited

OTHER PUBLICATIONS

Capranico, G., et al., "DNA sequence selectivity of topoisomerases and topoisomerase poisons," Biochim. Biophys. Acta, 1400:185-194 (1998).

Bernard, O.A., et al., "A novel gene, AF-1p, fused to HRX in t(1;11)(p32;q23), is not related to AF-4, AF-9 nor ENL," Oncogene, 9:1039-1045, (1994).

Whitmarsh, R.J., et al., "Reciprocal DNA topoisomerase II cleavage events at 5'-TATTA-3' sequences in MLL and AF-9 create homologous single-stranded overhangs that anneal to form der(11) and der(9) genomic breakpoint junctions in treatment-related AML without further processing," Oncogene, 22:8448-8459, (2003).

Wechsler, D.S., et al., "A novel chromosomal inversion at 11q23 in infant acute myeloid leukemia fuses MLL to CALM, a gene that encodes a clathrin assembly protein," Genes, Chromosomes & Cancer, 36:26-36, (2003).

Tse, W., et al., "A novel gene, AF1q, fused to MLL in t(1;11)(q21;q23), is specifically expressed in leukemic and immature hematopoietic cells," Blood, 85(3):650-656, (Feb. 1, 1995).

Tkachuk, D.C., et al., "Involvement of a homolog of Drosophila Trithorax by 11q23 chromosomal translocations in acute leukemias," Cell, 71:691-700, (Nov. 13, 1992).

Chervinsky, D.S., et al. "Complex MLL rearrangement in a patient with T-cell acute lymphoblastic leukemia." Genes Chromosomes Cancer. Sep. 1995;14(1):76-84.

Mitterbauer-Hohendanner, et al. "The biological and clinical significance of MLL abnormalities in haematological malignancies" European Journal of Clinical Investigation, Aug. 2004, vol. 34 (Suppl. 2), pp. 12-24.

Metzler, M., et al. "Asymmetric multiplex-polymerase chain reaction—a high throughput method for detection and sequencing genomic fusion sites in t(4;11)." Br J Haematol. Jan. 2004;124(1):47-54.

Klein, F., et al. "T lymphoid differentiation in human bone marrow." Proc Natl Acad Sci U S A. May 27, 2003;100 (11):6747-52. Epub May 8, 2003.

Invitrogen, TRIzol® Max. Bacterial RNA Isolation Kit, Part No. 25-0669, Rev. Date: Jul. 25, 2003, pp. 1-4.

Mecucci, M., et al. "Genetic profile of acute myeloid leukemia." Rev Clin Exp Hematol. Mar. 2002;6(1):3-25; discussion 86-7.

Hosono, S., et al. "Unbiased whole-genome amplification directly from clinical samples." Genome Res. May 2003;13 (5):954-64. Epub Apr. 14, 2003.

Akao, Y., et al., "Molecular analysis of the rearranged genome and chimeric mRNAs caused by the t(6;11)(q27;q23) chromosome translocation involving MLL in an infant acute monocytic leukemia," Genes, Chromosomes & Cancer, 27:412-417 (2000).

Blanco, J.G., et al., "Molecular emergence of acute myeloid leukemia during treatment for acute lymphoblastic leukemia," PNAS, 98(18):10338-10343 (Aug. 28, 2001).

Boyd, K.E., et al., "c-Myc target gene specificity is determined by a post-DNA-binding mechanism," Proc. Natl. Acad. Sci. USA, 95:13887-13892, (Nov. 1998).

Bromberg, K.D., et al., "DNA cleavage and religation by human topoisomerase IIalpha at high temperature," Biochem., 40:8410-8418, (2001).

Busson-Le Coniat, M., et al., "Mll-AF1q fusion resulting from t(1;11) in acute leukemia," Leukemia, 13:302-306, (1999).

Capranico, G., et al., "Nucleosome positioning as a critical determinant for the DNA cleavage sites of mammalian DNA topoisomerase II in reconstituted Simian virus 40 chromatin," Nuc. Acids Res., 18(15):4553-4559, (1990).

Capranico, G., et al., "Mapping drug interactions at the covalent topoisomerase II-DNA complex by bisantrene/amsacrine congeners," J. Biol. Chem., 273(21):12732-12739, (1998).

Chinwalla, V., et al., "A t(11;15) fuses MLL to two different genes, AF15q14 and a novel gene MPFYVE on chromosome 15," Oncogene, 22:1400-1410, (2003).

Corral, J., et al., "Acute leukemias of different lineages have similar MLL gene fusions encoding related chimeric proteins resulting from chromosomal translocation," Proc. Natl. Acad. Sci. USA, 90:8538-8542, (Sep. 1993).

Felxi, C.A., et al., "Panhandle PCR: a technical advance to amplify MLL genomic translocation breakpoints," Leukemia, 12:976-981, (1998).

Fu, J-F., et al., "Identification of CBL, a proto-oncogene at 11q23.3 as a novel MLL fusion partner in a patient with de novo acute myeloid leukemia," Genes, Chromosomes & Cancer, 37:214-219, (2003).

Hayakawa, A., et al., "Genomic organization, tissue expression, and cellular localization of AF3p21, a fusion partner of MLL in therapy-related leukemia," Genes, Chromosomes & Cancer, 30:364-374, (2001).

Hayashi, Y., et al., "SN-1, a novel leukemic cell line with t(11;16)(q23;p13): myeloid characteristics and resistance to retinoids and vitamin D3," Cancer Res., 60:1139-1145, (Feb. 15, 2000).

Hayette, S., et al., "AF15q14, a novel partner gene fused to the MLL gene in an acute myeloid leukaemia with a t(11;15)(q23;q14)," Oncogene, 19:4446-4450, (2000).

Hillion, J., et al., "AF6q21, a novel partner of the MLL gene in t(6;11)(q21;q23), defines a forkhead transcriptional factor subfamily," Blood, 90(9):3714-3719, (Nov. 1, 1997).

Huret, J.L., et al., "An atlas on chromosomes in hematological malignancies. Example: 11q23 and MLL partners," Leukemia, 15:987-989, (2001).

Joh, T., et al., "Chimeric MLL products with a Ras binding cytoplasmic protein AF6 involved in t(6;11) (q27;q23) leukemia localize in the nucleus," Oncogene, 15:1681-1687, (1997).

Krishnan, A., et al., "Predictors of therapy-related leukemia and myelodysplasia following autologous transplantation for lymphoma: an assessment of risk factors," Blood, 95(5):1588-1593, (Mar. 1, 2000).

Langer, T., et al., "Analysis of t(9;11) chromosomal breakpoint sequences in childhood acute leukemia: almost identical MLL breakpoints in therapy-related AML after treatment without etoposides," Genes, Chromosomes & Cancer, 36:393-401, (2003).

Lo Nigro, L., et al., "Reverse panhandle PCR identifies Ribosomal Protein S3 (RPS3) as a new partner gene of MLL in a three-way MLL rearrangement in infant acute monoblastic leukemia," Proc. ASCO, 18:565a, (1999). [Abstract].

Lo Nigro, L., et al., "Two new partner genes of MLL and additional heterogeneity in t(11;19) (q23;p13) translocations," Blood, 100(Supp. 11):531a, (2002). [Abstract].

Lorsbach, R.B., et al., "TET1, a member of a novel protein family, is fused to MLL in acute myeloid leukemia containing the t(10;11)(q22;q23)," Leukemia, 17:637-641, (2003).

Lovett, B.D., et al., "Etoposide metabolites enhance DNA topoisomerase II cleavage near leukemia-associated MLL translocation breakpoints," Biochem., 40:1159-1170, (2001).

Lovett, B.D., et al., "Near-precise interchromosomal recombination and functional DNA topoisomerase II cleavage sites at MLL and AF-4 genomic breakpoints in treatment-related acute lymphoblastic leukemia with t(4;11) translocation," PNAS, 98(17):9802-9807, (Aug. 14, 2001).

Maki, K., et al., "Transcriptional inhibition of p53 by the MLL/MEN chimeric protein found in myeloid leukemia," Blood, 93(10):3216-3224, (May 15, 1999).

Martineau, M., et al., "The t(6;11)(q27;q23) translocation in acute leukemia: a laboratory and clinical study of 30 cases," Leukemia, 12:788-791, (1998).

McIlhatton, M.A., et al., "Genomic organization, complex splicing pattern and expression of a human septin gene on chromosome 17q25.3," Oncogene, 20:5930-5939, (2001).

Megonigal, M.D., et al., "t(11;22)(q23;q11.2) in acute myeloid leukemia of infant twins fuses MLL with hCDCrel, a cell division cycle gene in the genomic region of deletion in DiGeorge and velocardinofacial syndromes," Proc. Natl. Acad. Sci. USA, 95:6413-6418, (May 1998).

(56) References Cited

OTHER PUBLICATIONS

Megonigal, M.D., et al., "Detection of leukemia-associated MLL-GAS7 translocation early during chemotherapy with DNA topoisomerase II inhibitors," PNAS, 97(6):2814-2819, (Mar. 14, 2000).

Megonigal, M.D., et al., "Panhandle PCR for cDNA: a rapid method for isolation of MLL fusion transcripts involving unknown partner genes," PNAS, 97(17):9597-9602, (Aug. 15, 2000).

Mitani, K., et al., "Cloning of several species of MLL/MEN chimeric cDNAs in myeloid leukemia with t(11;19)(q23; p13.1) translocation," Blood, 85(8):2017-2024, (Apr. 15, 1995).

Moorman, A.V., et al., "The translocations, t(11;19)(q23;p13.1) and t(11;19)(q23;p13.3): a cytogenetic and clinical profile of 53 patients," Leukemia, 12:805-810, (1998).

Nakamura, T., et al., "Genes on chromosomes 4, 9, and 19 involved in 11q23 abnormalities in acute leukemia share sequence homology and/or common motifs," Proc. Natl. Acad. Sci. USA, 90:4631-4635, (May 1993).

Ono, R., et al., "LCX, leukemia-associated protein with a CXXC domain, is fused to MLL in acute myeloid leukemia with trilineage dysplasia having t(10;11)(q22;q23)," Cancer Res., 62:4075-4080, (Jul. 15, 2002).

Pegram, L.D., et al., "t(3;11) translocation in treatment-related acute myeloid leukemia fuses MLL with the GMPS (Guanosine 5' Monophosphate Synthetase) gene," Blood, 96(13):4360-4362, (Dec. 15, 2000).

Prasad, R., et al., "Cloning of the ALL-1 fusion partner, the AF-6 gene, involved in acute myeloid leukemias with the t(6;11) chromosome translocation," Cancer Res., 53:5624-5628, (Dec. 1, 1993).

Raffini, L.J., et al., "Panhandle and reverse-panhandle PCR enable cloning of der(11) and der(other) genomic breakpoint junctions of MLL translocations and identify complex translocation of MLL, AF-4, and CDK6," PNAS, 99(7):4568-4573, (Apr. 2, 2002).

Rowley, J.D., et al., "All patients with the T(11;16)(q23;p13.3) that involves MLL and CBP have treatment-related hematologic disorders," Blood, 90(2):535-541, (Jul. 15, 1997).

Rubnitz, J.E., et al., "Molecular analysis of t(11;19) breakpoints in childhood acute leukemias," Blood, 87(11):4804-4808, (Jun. 1, 1996).

Sano, K., "Structure of AF3p21, a new member of mixed lineage leukemia (MLL) fusion partner proteins-implication for MLL-induced leukemogenesis," Leukemia and Lymphoma, 42(4):595-602, (2001).

Satake, N., et al., "Novel MLL-CBP fusion transcript in therapy-related chronic myelomonocytic leukemia with a t(11;16)(q23;p13) chromosome translocation," Genes, Chromosomes & Cancer, 20:60-63, (1997).

Shilatifard, A., et al., "An RNA polymerase II elongation factor encoded by the human ELL gene," Science, 271:1873-1876, (Mar. 29, 1996).

Slater, D.J., et al., "MLL-SEPTIN6 fusion recurs in novel translocation of chromosomes 3, X, and 11 in infant acute myelomonocytic leukaemia and in t(X;11) in infant acute myeloid leukaemia, and MLL genomic breakpoint in complex MLL-SEPTIN6 rearrangement is a DNA topoisomerase II cleavage site," Oncogene, 21:4706-4714, (2002).

So, C.W., et al., "The interaction between EEN and Abi-1, two MLL fusion partners, and synaptojanin and dynamin: implications for leukaemogenesis," Leukemia, 14:594-601, (2000).

So, C.W., et al., "EEN encodes for a member of a new family of proteins containing an Src homology 3 domain and is the third gene located on chromosome 19p13 that fuses to MLL in human leukemia," Proc. Natl. Acad. Sci. USA, 94:2563-2568, (Mar. 1997).

Sobulo, O.M., et al., "MLL is fused to CBP, a histone acetyltransferase, in therapy-related acute myeloid leukemia with a t(11;16)(q23;p13.3)," Proc. Natl. Acad. Sci. USA, 94:8732-8737, (Aug. 1997).

Strehl, S., et al., "The human LASP1 gene is fused to MLL in an acute myeloid leukemia with t(11;17)(q23;q21)," Oncogene, 22:157-160, (2003).

Sugita, K., et al., "MLL-CBP fusion transcript in a therapy-related acute myeloid leukemia with the t(11;16)(q23;p13) which developed in an acute lymphoblastic leukemia patient with Fanconi Anemia," Genes, Chromosomes & Cancer, 27:264-269, (2000).

Taki, T., et al., "The t(11;16)(q23;p13) translocation in myelodysplastic syndrome fuses the MLL gene to the CBP gene," Blood, 89(11):3945-3950, (Jun. 1, 1997).

Thirman, M.J., et al., Cloning of ELL, a gene that fuses to MLL in a t(11;19)(q23;p13.1) in acute myeloid leukemia, Proc. Natl. Acad. Sci. USA, 91:12110-12114, (Dec. 1994).

\* cited by examiner

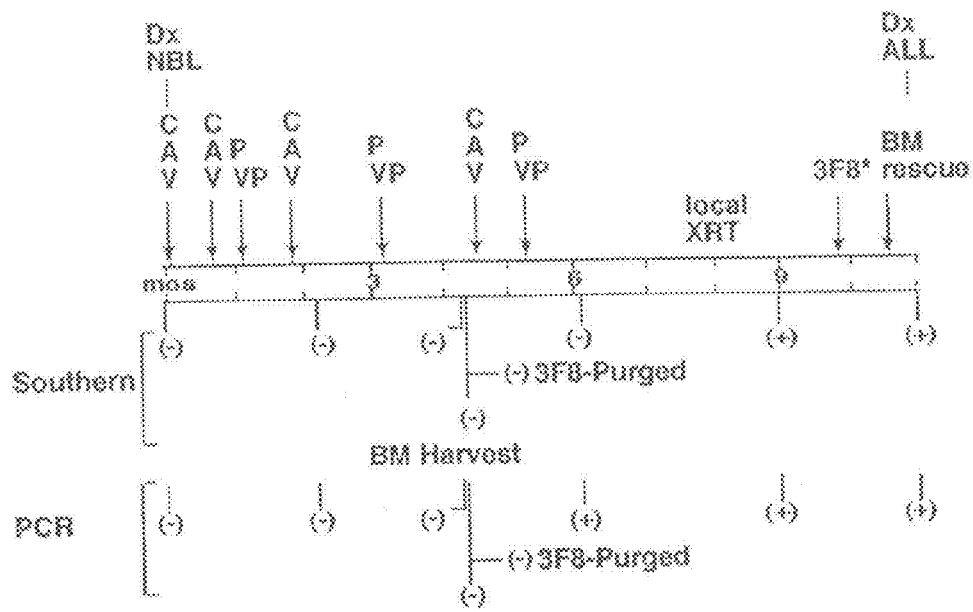
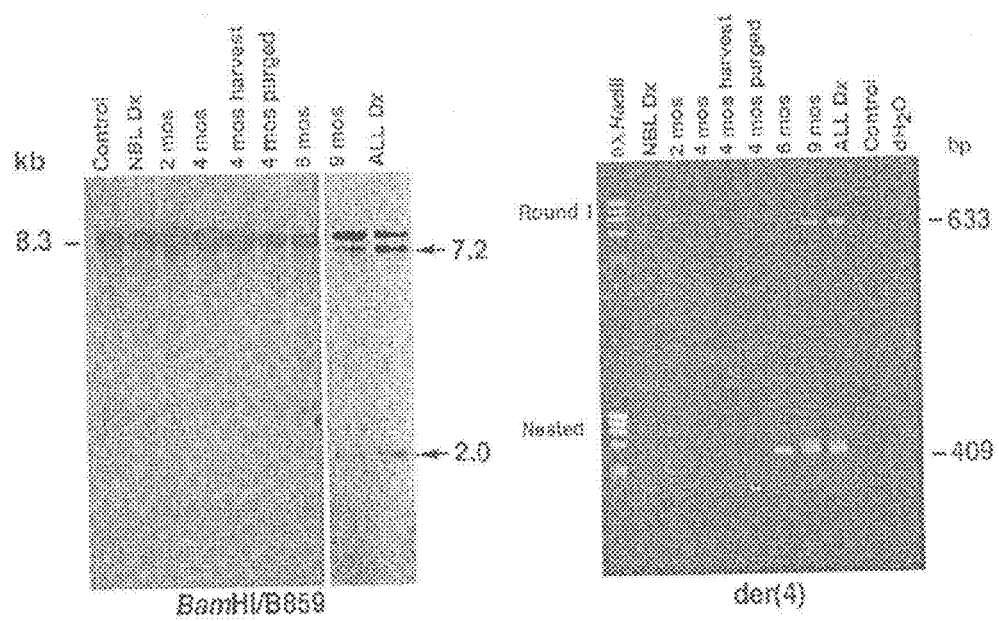
Fig. 1A
Fig. 1B
Fig. 1C

AlexFluor 546 0.2 µg   AlexaFluor 647 0.02 µg

COMPOSITIONS AND METHODS FOR THE DETECTION OF TOPOISOMERASE II COMPLEXES WITH DNA

This application is a divisional application of U.S. patent application Ser. No. 11/222,626, filed on Sep. 9, 2005 now abandoned, which claims priority under 35 U.S.C. §119(e) to U.S. Provisional Patent Application No. 60/608,331, filed on Sep. 9, 2004. The foregoing applications are incorporated by reference herein.

Pursuant to 35 U.S.C. §202(c) it is acknowledged that the U.S. Government has certain rights in the invention described herein, which was made in part with funds from the National Institutes of Health, Grant Numbers RO1 CA77683, CA85469, and CA80175.

FIELD OF THE INVENTION

The present invention relates to the fields of molecular biology and oncology. More specifically, the invention provides compositions and methods for detection of DNA topoisomerase II complexes with genomic DNA.

BACKGROUND OF THE INVENTION

Several publications and patent documents are cited throughout the specification in order to describe the state of the art to which this invention pertains. Each of these citations is incorporated herein by reference as though set forth in full.

Epipodophyllotoxins and anthracyclines, which are commonly used chemotherapeutic DNA topoisomerase II inhibitors, more accurately are called DNA topoisomerase II poisons because they increase the concentration of DNA topoisomerase II cleavage complexes and have the overall effect of enhancing cleavage, which is cytotoxic (1). These agents are associated with leukemia as a treatment complication (2). Most DNA topoisomerase II inhibitor-related leukemias have MLL (myeloid lymphoid leukemia) translocations (3). The translocations disrupt an 8.3 kb bcr between exons 5-11 of the ~100 kb MLL gene at chromosome band 11q23. The association of DNA topoisomerase II inhibitors with leukemia has suggested a translocation mechanism that involves chromosomal breakage from drug-stabilized DNA topoisomerase II cleavage and formation of the breakpoint junctions when the breakage is repaired (2). The drug stabilized complexes have been called ternary (drug-DNA-topoisomerase II) complexes in the literature. In previous reports, MLL translocations have been characterized and tracked in leukemias in two patients receiving chemotherapy (Megonigal 2000; Blanco 2001), and the role of chemotherapy-stabilized DNA topoisomerase II cleavage in the translocation process has been investigated in in vitro assays of DNA substrates outside of the cellular context (Lovett, 2001; Lovett 2001; Whitmarsh 2003). However, cell death from chemotherapy also forces bone marrow progenitor cell proliferation (4) and native DNA topoisomerase IIα expression is highest in proliferating cells (5, 6).

Genomic breakpoint junctions on derivative chromosomes arising from MLL translocations were cloned in two cases of leukemia following intensive neuroblastoma regimens (7, 8). Such chemotherapy regimens have been associated with a high incidence of leukemia as a treatment complication (9).

SUMMARY OF THE INVENTION

It is an objective of the present invention to provide compositions and methods for detecting ternary topoisomerase II/DNA complexes with cytotoxic chemotherapy drugs (e.g., DNA topoisomerase II poisons) or with natural compounds that have similar activity, as well as topoisomerase II complexes with DNA formed by the native enzyme as a means to assess strategies to prevent the oncogenic events associated with chemotherapy and exposure to natural topoisomerase II inhibitors.

In addition, it is known that cytotoxic chemotherapy may cause cell death that is followed by bone marrow progenitor cell proliferation with accompanying increased native DNA topoisomerase II expression. A patient has recently been identified with leukemia with an MLL translocation which emerged after chemotherapy that did not include a DNA topoisomerase II poison (Langer, 2003). Accordingly, it is another objective of the present invention to provide compositions and methods for detecting topoisomerase II/DNA complexes that are formed by the native enzyme at elevated levels, and as a means to prevent leukemogenic events associated with chemotherapy.

Thus, in accordance with the present invention, compositions, methods, and kits are provided for the detection of topoisomerase II-genomic DNA complexes. The detection of such complexes can be indicative of DNA damage, particularly in relation to treatment-related leukemia. An exemplary method entails providing cells which express topoisomerase II and exposing the cells to an agent suspected of inducing formation of agent-topoisomerase-DNA cleavage complexes for a time period sufficient for such complexes to form. The cells are then lysed and DNA-topoisomerase cleavage complexes are isolated. Alternatively, the cells can be exposed to agents that result in increased expression of topoisomerase II without formation of agent-topoisomerase-DNA cleavage complexes, in which topoisomerase II-DNA cleavage complexes can be measured. Following isolation, the DNA present in the isolated complexes can be amplified by degenerative oligonucleotide PCR and then assayed by real-time PCR with primers specific for the region of interest, such as, for example, the MLL breakpoint cluster region (bcr). Alternatively or additionally, the DNA present in the isolated complexes that has been amplified by degenerative oligonucleotide PCR can be labeled with a detectable label. The optionally labeled DNA is then characterized via hybridization to predetermined sequences present in the region of genomic DNA where the complexes form in order to characterize the sites of complex formation with DNA at the sequence level. In one aspect of the invention, the predetermined sequences are present on a microarray. According to another aspect, the genomic DNA sequences are from the MLL bcr. According to another aspect, the genomic DNA sequences, with or without DNA sequences from the MLL bcr, comprise partner genes which are fused with MLL in certain leukemias. In accordance with another aspect of the invention, the genomic DNA sequences are sequences associated with leukemia. In accordance with yet another aspect of the invention, the genomic DNA sequences comprise the entire human genome.

In accordance with another aspect of the instant invention, a method for identifying sequences present in DNA topoisomerase II-DNA complexes in cells is provided. The method comprises: a) providing cells suspected of containing DNA topoisomerase II-DNA complexes; b) isolating DNA topoisomerase II-DNA complexes from the cell; c) amplifying the DNA present in isolated DNA topoisomerase II-DNA complexes via polymerase chain reaction; and d) identifying the sequences present in said amplified DNA, thereby identifying the sequences present in said DNA topoisomerase II-DNA complexes. In a preferred embodiment, the DNA in the DNA topoisomerase II-DNA complexes is genomic DNA. In a particular embodiment, the identification of the sequences in step d) comprises 1) further amplifying the amplified DNA from step c) with gene specific primers; 2) further amplifying the amplified DNA from step c) by real-time PCR; and/or 3) hybridizing the amplified DNA from step c) with a microarray, such as those described hereinbelow. In another embodiment, the cells are CD34+ cells. Additionally, the amplified DNA of step c) may comprise sequences from the MLL gene. According to another aspect of the invention, the cells are exposed to an agent suspected of modulating formation of topoisomerase cleavage complexes.

In yet another aspect of the invention, microarrays are provided. In a particular embodiment, the microarray comprises at least one of the group consisting of MLL bcr oligonucleotide sequences and oligonucleotide sequences of MLL partner genes. In another embodiment, the MLL bcr oligonucleotide sequences hybridize to non-repetitive MLL bcr sequences. The microarrays may also further comprise oligonucleotide sequences from the Alu region between nucleotide positions 663-1779 in the MLL bcr and/or control sequences which are not involved in MLL translocations. Examples of control sequences include, without limitation, MLL exon 25, MLL exon 3, GAPDH, c-myc, and bacterial gene sequences. MLL partner genes include, without limitation, LAF-4, AF4 (MLLT2, FEL), AF5α, AF5q31, AF6q21 (FKHRL1), AF9 (MLLT3), AF10, MLL, AF17, ENL (MLLT1, LTG19), AFX, CBP, ELL (MEN), p300, AF3p21, LCX (TET1), AF15q14, AF1p (eps15), AF1q, GMPS, LPP, GRAF, AF6, CDK6, FBP17, ABI-1, CBL, MPFYVE, GAS7, LASP1, MSF, EEN, hCDCrel, SEPTIN6, CALM, LARG, GPHN, MYO1F, Alkaline Ceramidase, RPS3, and MIFL. In a particular embodiment of the invention, the microarray comprises oligonucleotide sequences of at least one of SEQ ID NOs 1-162. In another particular embodiment of the invention, the microarray comprises oligonucleotide sequences of at least one of SEQ ID NOs 163-246.

In accordance with yet another aspect of the instant invention, kits are provided for performing the methods of the instant invention, such as for the detection of DNA-DNA topoisomerase II complexes and the sequences of the DNA of these complexes. The kits may comprise any or all of the following: an agent and a buffer for lysing cells; a solid support; a buffer for isolating DNA-DNA topoisomerase II complexes; at least one primer for use in whole genome amplification method; a buffer for PCR amplification of isolated topoisomerase II bound DNA; primers and buffer for real-time PCR analysis of specific genes in the isolated, topoisomerase II-bound DNA that has been amplified by a whole genome amplification method; at least one detectable label for comparative labeling of topoisomerase II bound DNA from two cell populations that has been amplified by a whole genome amplification method or comparative labeling of topoisomerase II bound DNA from one cell population that has been amplified by a whole genome amplification method and a calibrated control DNA; calibrated control DNA for labeling and hybridization to the microarray at the same time as the test sample labeled with another detectable label; a microarray comprising sequences from at least one of the group consisting of the MLL bcr and MLL partner genes and, optionally, control sequences; and instruction material. In a particular aspect of the invention, the kit comprises: a) an agent and a buffer for lysing cells; b) a solid support and a buffer for isolating DNA-DNA topoisomerase II complexes; c) at least one primer and a buffer for PCR amplification of isolated DNA by whole genome amplification; d) at least one first detectable label for incorporation into products of whole genome amplification; e) calibrated reference standard DNA comprising a second detectable label; f) a microarray comprising oligonucleotide sequences from the MLL bcr; and g) instruction material.

BRIEF DESCRIPTION OF THE DRAWINGS

FIG. 1A is a summary of the clinical course and treatment of patient t-120 and the Southern blot and PCR analysis of sequential bone marrow specimens. The chemotherapy cycles administered according to the Memorial Sloan-Kettering N7 regimen were CAV (cyclophosphamide 4200 mg/m$^2$, doxorubicin 75 mg/m$^2$, vincristine 1.5 mg/m$^2$) or PVP (cisplatin 200 mg/m$^2$, etoposide 600 mg/m$^2$). 3F8* indicates radiolabeled anti-GD2 monoclonal antibody treatment. (+) or (−) indicates detection of MLL translocation by Southern blot analysis or by nested PCR with gene-specific primers. FIG. 1B is a gel of a Southern blot analysis of MLL breakpoint cluster region (bcr) rearrangements in sequential marrow specimens. FIG. 1C is a gel of Clonotypic PCR analysis (Round 1) and nested clonotypic PCR analysis of the der(4) genomic breakpoint junction in sequential marrow specimens.

FIG. 2A is an analysis of normal homologues of MLL genomic breakpoint sequences in ALL (acute lymphoblastic leukemia) of patient t-120. DNA topoisomerase II cleavage of MLL intron 8 coordinates 6513 to 6778. FIG. 2B is an analysis of normal homologues of AF-4 genomic breakpoint sequences in ALL of patient t-120 in DNA topoisomerase II in vitro cleavage assays. DNA topoisomerase II cleavage of AF-4 intron 3 coordinates 6956 to 7239. The indicated reactions were incubated for an additional 10 min at 75° C. before trapping of covalent complexes. The 5' side (−1 position) of the cleavage sites are shown. Corkscrew arrows at far right indicate translocation breakpoints.

In FIG. 3A, DNA topoisomerase II cleavage sites at MLL intron 8 position 6588 and AF-4 intron 3 position 7126 with 4-base 5' overhangs are shown at the top. The cleavage at MLL (fragment shown: top strand is SEQ ID NO: 258; bottom strand is SEQ ID NO: 266) intron 8 position 6588 was detected in the presence of etoposide, etoposide metabolites and doxorubicin. The cleavage at AF-4 (fragment shown: top strand is SEQ ID NO: 259; bottom strand is SEQ ID NO: 268) intron 3 position 7126 was detected in the presence of etoposide and etoposide metabolites. The processing includes exonucleolytic nibbling (italic) to form single-base homologies and create both breakpoint junctions of the t(4; 11) by error-prone non-homologous end joining (NHEJ) (boxes). In formation of the der(11) (top strand is SEQ ID NO: 260; bottom strand is SEQ ID NO: 267) positions 6590 to 6592 on the antisense strand of MLL and positions 7127 to 7129 on the sense strand of AF-4 are lost by exonucleolytic nibbling (italic, middle) before NHEJ (box, middle) joins the indicated bases (under exonucleolytic nibbling, left fragment: top strand is nucleotides 1-19 of SEQ ID NO: 258 and bottom strand is nucleotides 21-43 of SEQ ID NO: 266; right fragment: top strand is nucleotides 24-44 of SEQ ID NO: 259 and bottom strand is nucleotides 1-17 of SEQ ID NO: 268). Positions 7110 to 7126 on the sense strand of AF-4, positions 7111 to 7130 on the antisense strand of AF-4, positions 6589 to 6594 on the sense strand of MLL and positions 6593 to 6595 on the antisense strand of MLL are lost by exonucleolytic nibbling (italic, bottom) and the der(4) (top strand is SEQ ID NO: 261; bottom strand is SEQ ID NO: 269) also forms by NHEJ (box, bottom; under exonucleolytic nibbling, left fragment: top strand is nucleotides 1-23 of SEQ ID NO: 259 and bottom strand is nucleotides 18-44 of SEQ ID NO: 268; right fragment: top strand is nucleotides 20-43 of SEQ ID NO: 258 and bottom strand is nucleotides 1-20 of SEQ ID NO: 266). Similarly, FIG. 3B demonstrates the formation of der(11) (top strand is SEQ ID NO: 260; bottom strand is SEQ ID NO: 267) and der(4) (top strand is SEQ ID NO: 261; bottom strand is SEQ ID NO: 269) genomic breakpoint junctions wherein the DNA topoisomerase II cleavage sites at MLL (fragment shown: top strand is SEQ ID NO: 258; bottom strand is SEQ ID NO: 266) intron 8 position 6588 and AF-4 (fragment shown: top strand is SEQ ID NO: 259; bottom strand is SEQ ID NO: 268) intron 3 position 7114 are employed, the latter of which was detected in the presence of doxorubicin (top box, under exonucleolytic nibbling, left fragment: top strand is nucleotides 1-19 of SEQ ID NO: 258 and bottom strand is nucleotides 21-43 of SEQ ID NO: 266; right fragment: top strand is nucleotides 12-44 of SEQ ID NO: 259 and bottom strand is nucleotides 1-29 of SEQ ID NO: 268; bottom box, under exonucleolytic nibbling, left fragment: top strand is nucleotides 1-11 of SEQ ID NO: 259 and bottom strand is nucleotides 29-44 of SEQ ID NO: 268; right fragment: top strand is nucleotides 20-43 of SEQ ID NO: 258 and bottom strand is nucleotides 1-20 of SEQ ID NO: 266).

DETAILED DESCRIPTION OF THE INVENTION

Figure 2A:
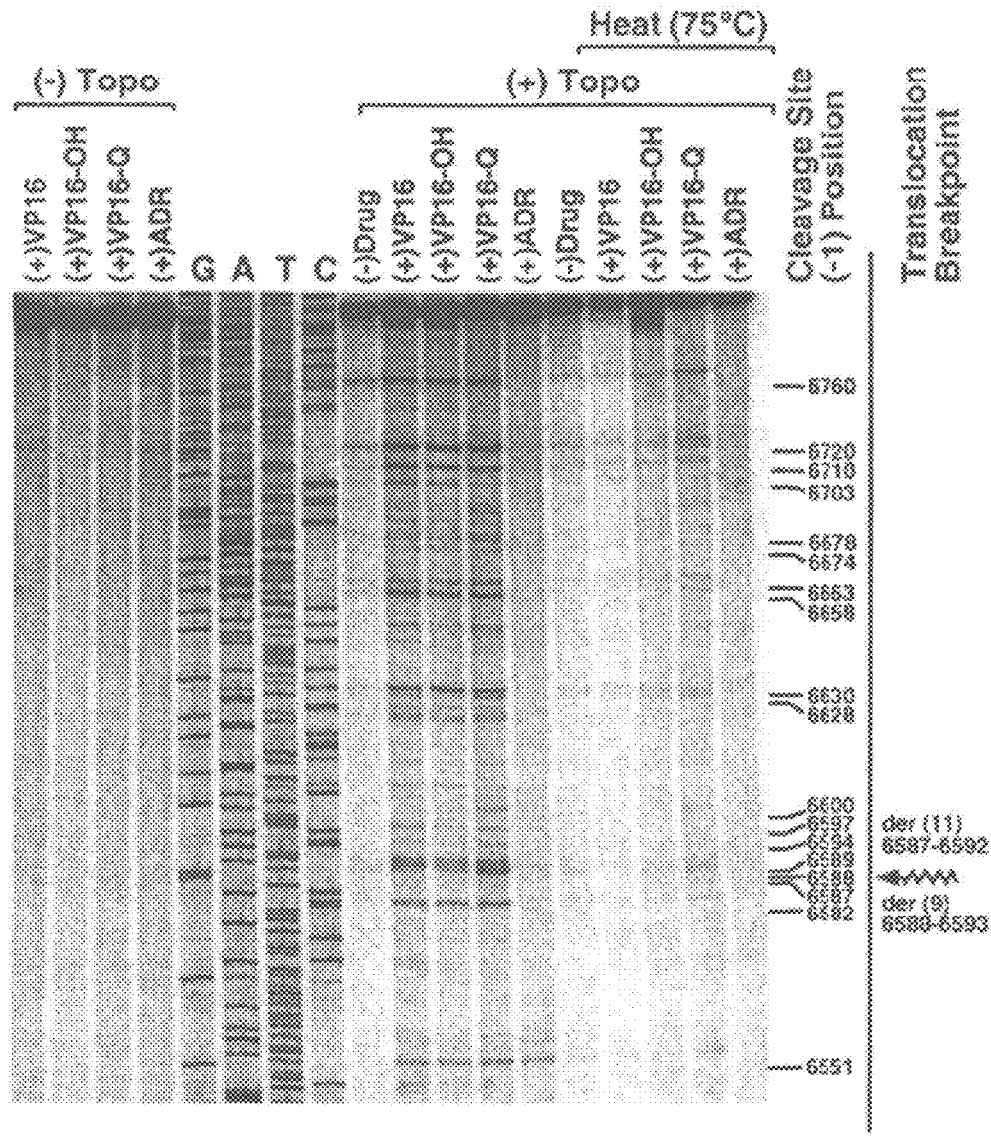
FIGS. 2A and 2B are images of autoradiographs showing the cleavage products after 10 min incubation at 37° C. of 25 ng (30,000 cpm) singly 5' end-labeled DNA with 147 nM human DNA topoisomerase IIα, 1 mM ATP and, where indicated, 20 μM etoposide (VP16), etoposide catechol (VP16-OH), etoposide quinone (VP16-Q), or doxorubicin (ADR).

The emergence of the MLL translocation relative to intensive multimodality neuroblastoma therapy administered to two patients with secondary acute leukemia was traced to assess the role of specific agents in the genesis of the translocations. An in vitro assay was employed and a CD34+ cell model developed in order to pinpoint whether the translocations arose from drug stimulated DNA topoisomerase IIα cleavage and formation of drug-DNA-topoisomerase II complexes at or in close proximity to the translocation breakpoints. Variability in the molecular emergence of traceable translocations was found. In one case, the t(4; 11) was first detectable 6 months after neuroblastoma diagnosis, following completion of all chemotherapy and exposure to etoposide and doxorubicin. Processing of functional DNA topoisomerase II cleavage sites enhanced by etoposide or its metabolites or doxorubicin resulted in both breakpoint junctions. In another case, doxorubicin was the only DNA topoisomerase II inhibitor exposure before detection of the MLL-GAS7 translocation at six weeks after starting treatment (7). There were strong DNA topoisomerase II cleavage sites detected without drug and further enhanced by doxorubicin in MLL and GAS7 that resulted in both breakpoint junctions. This is the first functional demonstration of relevance of doxorubicin-DNA-topoisomerase II covalent complexes with MLL and with its partner gene in the genesis of MLL translocations in treatment-related AML.

In the ALL of patient t-120 described above, the translocation breakpoint in the leukemia and the site of in vitro drug-DNA-topoisomerase II complex formation both were at the translocation breakpoint hotspot region 3' in intron 8 in the MLL bcr (reviewed in Whitmarsh 2003). In the recent treatment-related AML described by Langer (2003) where the leukemia occurred after cytotoxic chemotherapy without DNA topoisomerase II poisons, the translocation breakpoint also was at the same translocation breakpoint hotspot region. The in vitro assays described above as well as in Whitmarsh (2003) showed that not only drug-DNA-topoisomerase II complexes but also DNA-native topoisomerase II complexes were formed in this translocation breakpoint hotspot region.

It was important to devise a cellular model to further study the role of DNA topoisomerase II cleavage in the genesis of MLL translocations because cleavage sites in the cellular context should be more restricted than in vitro (Capranico et al., 1990). In the development of this cellular model it was important to focus on the breakpoint hotspot region 3' in intron 8 of the MLL bcr. DNA topoisomerase II was highly expressed in CD34+ cells and formed cleavage complexes with the MLL bcr at the 3' breakpoint hotspot region in untreated CD34+ cells and CD34+ cells treated with etoposide. These findings establish that DNA topoisomerase II forms cleavage complexes with the MLL bcr in bone marrow stem cells, and implicate not only drug-stabilized DNA topoisomerase II cleavage but also native DNA topoisomerase II cleavage as mechanisms to damage MLL.

A modified in vivo complex of enzyme (ICE) bioassay, which entails trapping and immunodetection of DNA covalently bound to DNA topoisomerase II, has been developed to examine native and chemotherapy-stabilized DNA topoisomerase II cleavage complexes in ex vivo stimulated CD34+ progenitor cells from normal human marrow. The details of the ICE assay as applied to cell lines were described in (Whitmarsh 2003). However, the ICE bioassay detects overall formation of DNA topoisomerase II covalent complexes genome-wide but does not address the enzyme-DNA interaction at the sequence level.

In accordance with the present invention, a new approach was created to detect DNA topoisomerase II covalent complexes with MLL bcr in CD34+ cells at the sequence level. Total genomic DNA samples including protein-bound DNA from untreated or etoposide-treated ex vivo-expanded human CD34+ cells were prepared on a CsCl cushions according to the ICE assay protocol. However, the ICE assay then utilizes immunoblotting to detect all DNA in total genomic DNA bound to DNA topoisomerase IIα by the covalent phosphotyrosine linkage formed between this enzyme and DNA (Whitmarsh et al., 2003) without attention to any specific sequences. The instant assay diverges, for example, from the ICE assay in the following manner: DNA topoisomerase IIα covalent complexes in the total genomic DNA isolated using the CsCl cushion are purified on an immuno-affinity column consisting of Protein A-Sepharose beads covalently coupled to a mouse anti-human DNA topoisomerase IIα antibody. Eluted material from the column is then subjected to degenerative oligonucleotide PCR (DOP) in order to generate template DNAs in sufficient quantity for real-time PCR. MLL bcr primers for real-time PCR were designed to amplify positions 6784 to 6851 at the junction of intron 8-exon 9 near the previously described translocation breakpoint hotspot (Whitmarsh et al., 2003). Other primer pairs would amplify a genomic region of GAPDH and a genomic region of MLL exon 25, which are not involved in MLL translocations (Langer et al., 2003). Yet other primers would amplify a region of the MLL bcr at the junction of intron 7-exon 8 near a region where other MLL translocation breakpoints have been identified in cases of leukemia in infants.

The finding of native DNA topoisomerase II complexes and etoposide-DNA-topoisomerase II complexes in total genomic DNA (without regard to any specific sequences in the genome) of CD34+ cells by ICE had never been described. Moreover, the assay disclosed herein that incorporates immuno affinity purification, whole genome amplification and real-time PCR after isolation of total cellular DNA including protein bound DNA, to rapidly detect DNA topoisomerase II covalently bound specifically to the MLL bcr in human CD34+ cells. Using this new assay, native as well as etoposide-stabilized DNA topoisomerase II covalent complexes with the MLL bcr were detectable in the immuno-affinity purified DNA topoisomerase II covalent complexes, demonstrating for the first time that DNA topoisomerase II forms covalent complexes with MLL at sites of translocation breakpoints in human CD34+ cells. Since DNA templates containing double-strand breaks from DNA topoisomerase II cleavage would not be amplified by PCR, these data indicate the presence of DNA-DNA topoisomerase II covalent complexes proximal to the amplicon (MLL bcr positions 6784 to 6851) where products were detected with resolution at the size of the DOP template. The use of chemotherapy creates a risk for leukemia as a treatment complication. Tracing of the temporal molecular emergence of the leukemia-associated MLL translocations relative to chemotherapy administration and analysis of the genomic breakpoint junction sequences in the leukemias and functional DNA topoisomerase II cleavage assays suggest that not only drug-stabilized but also native DNA topoisomerase II cleavage can result in translocations. In particular, a rare case of treatment-related leukemia recently was described where the prior chemotherapy exposure did not include a DNA topoisomerase II poison (Langer 2003) Native DNA topoisomerase II cleavage can be the cause of the DNA damage in such cases because cytotoxic chemotherapy in general typically is followed by bone marrow progenitor cell proliferation (Knudson, 1992), which would be associated with high DNA topoisomerase IIα expression (Isaacs et al., 1998; Woessner et al., 1991).

In accordance with the present invention, a custom oligonucleotide array comprising sequences that span the breakpoint cluster region of the MLL gene that is disrupted in infant leukemias and treatment-related leukemias is provided. This custom oligonucleotide array can be used as an alternative to the real time PCR approach to detect the specific sequences that are involved in the formation of DNA-topoisomerase complexes or drug-DNA-topoisomerase complexes. This microarray facilitates analysis of the formation of DNA topoisomerase II complexes with MLL upon various different treatments of primary human hematopoietic cells and hematopoietic cell lines or non-hematopoietic cells. Briefly, such complexes can be detected by 1) treating the cells (in vitro, ex vivo, or in vivo), 2) isolating total genomic DNA including protein bound DNA, 3) isolating DNA topoisomerase II-bound DNA (e.g., on an immunoaffinity column), 4) amplifying the DNA by degenerative oligonucleotide PCR or by alternative whole-genome amplification methods, 5) labeling the test sample and a calibrated reference sample with different detectable labels (e.g., two different fluorescent dyes), and 6) hybridizing the labeled test sample and the calibrated standard or, alternatively, two different test samples labeled with different dyes with an MLL bcr microarray with two different channels, one channel for each one of the two dyes. The Examples describe experiments utilizing real-time PCR and microarrays to further characterize topoisomerase II-genomic DNA complexes and the sequences bound by topoisomerase II. Partner genes identified by various panhandle PCR techniques (see, e.g., U.S. Pat. No. 6,368,791; U.S. patent application Ser. No. 10/118,783; and U.S. Provisional Application 60/599,385), or by other techniques that lead to the identification of the sequences of translocation breakpoints may also be used with the real-time PCR and microarrays (see Table 6 for list of exemplary partner genes). The partner genes can be employed, alone or in combination with the MLL bcr in order to determine the relationship of translocation breakpoints to sites of DNA topoisomerase complex formation in different types of cells.

Notably, DNA damage mediated by aberrant topoisomerase activity can occur following exposure to naturally occurring topoisomerase poisons/inhibitors rather than chemotherapeutic agents, and exposure of pregnant women to such agents has been linked to infant leukemias. The methods and compositions of the invention can be utilized to characterize this DNA damage and provide the means to develop strategies to prevent topoisomerase II mediated alteration of the fetal chromosomal DNA during pregnancy.

DEFINITIONS

As used herein, the term "microarray" refers to an ordered arrangement of hybridizable array elements. The array elements are arranged so that there are preferably at least one or more different array elements, more preferably at least 100 array elements, and most preferably at least 1,000 array elements on a solid support. Preferably, the hybridization signal from each of the array elements is individually distinguishable, the solid support is a chip, and the array elements comprise oligonucleotide probes.

The term "MLL partner gene" refers to the gene or genomic DNA sequence fused with MLL after a translocation, such as those fusions present in certain leukemias.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

For instance, one common formula for calculating the stringency conditions required to achieve hybridization between nucleic acid molecules of a specified sequence homology is set forth below (Sambrook et al., 1989):

$$T_m = 81.5° C. + 16.6 \text{ Log } [Na+] + 0.41(\% \, G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1× SSC and 0.5% SDS at 65° C. for 15 minutes.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

As used herein, an "instructional material" includes a publication, a recording, a diagram, or any other medium of expression which can be used to communicate the usefulness of the composition of the invention for performing a method of the invention.

The phrase "solid support" refers to any solid surface including, without limitation, any chip (for example, silica-based, glass, or gold chip), glass slide, membrane, bead, solid particle (for example, agarose, sepharose, polystyrene or magnetic bead), column (or column material), test tube, or microtiter dish.

The following materials and methods are provided to facilitate the practice of the present invention.

Cloning and Detection of MLL Genomic Breakpoint Junction Sequences in Sequential Bone Marrows Characterization of genomic breakpoint junction sequences of the der(11) and other derivative chromosomes in the leukemias of the patients designated patients t-120 and t-39 by panhandle PCR approaches and PCR with gene-specific primers was previously described (7, 8). Backtracking to examine molecular emergence of the translocation in sequential bone marrow specimens from patient t-39 and to date the translocation in relation to chemotherapy administration has been reported (7). For patient t-120 diagnosed with treatment-related ALL harboring t(4; 11), BamHI-digested DNAs from sequential marrow samples were analyzed with the B859 fragment of ALL-1 cDNA corresponding to the MLL bcr. The der(4) genomic breakpoint junction sequence obtained by reverse panhandle PCR (8) provided sequences for forward AF-4 primer 5'-ATTGTTCTGCCCCCAA-CATA-3' (SEQ ID NO: 247) and reverse MLL primer 5'-AGAGGCCCAGCTGTAGTTCT-3' (SEQ ID NO: 248), and nested forward AF-4 primer 5'-TCCGTAAGCTCGAC-CCTAGT-3' (SEQ ID NO: 249) and nested reverse MLL primer 5'-GCGCTCGTTCTCCTCTAAAC-3' (SEQ ID NO: 250), which were used for clonotypic PCR to examine sequential bone marrow samples for molecular emergence of the t(4; 11) translocation in relation to chemotherapy administered.

DNA Topoisomerase II In Vitro Cleavage Assays

DNA topoisomerase II in vitro cleavage assays were performed using previously described methods (10, 11). DNA fragments containing the normal homologues of each genomic breakpoint in MLL or GAS7 were subcloned into the EcoRI and BamHI sites, and the DNA fragment containing the normal homologue of the AF-4 genomic breakpoint into the BamHI and NotI sites of pBluescript II SK (Stratagene; La Jolla, Calif.). Twenty-five ng of singly 5' end-labeled DNA substrates from these plasmids were incubated with human DNA topoisomerase IIα, ATP and $MgCl_2$ in absence of drug or in the presence of etoposide, etoposide catechol, etoposide quinone or doxorubicin at 20 µM final concentration for 10 min at 37° C. DNA topoisomerase II cleavage complexes were irreversibly trapped by adding SDS, without heating or after subsequent incubation for 10 min at 75° C. to evaluate heat stability (12). Cleavage complexes were deproteinized and electrophoresed in a DNA sequencing gel alongside a dideoxy sequencing ladder to locate the cleavage sites (10, 11). In addition, doxorubicin was studied over a range of lower concentrations because of its known mixed effects of DNA topoisomerase II cleavage enhancement at low concentrations and DNA topoisomerase II catalytic inhibition due to intercalation at high concentrations (Capranico, 1998).

Ex Vivo Expansion of CD34+ Cells

Ten×$10^6$ primary human cadaveric bone marrow CD34+ cells obtained through NHLBI were established in culture at a density of 2×$10^4$ to 2×$10^5$ cells per ml and expanded in two T-75 flasks for 8 days in HPGM serum-free medium (Cambrex, Walkersville, Md.) supplemented with 100 ng/ml each of stem cell factor, Flk2/Flt3 ligand (FL) and IL-6, 10 ng/ml thrombopoietin and 1 µg/ml soluble IL-6 receptor (R&D Systems, Minneapolis, Minn.), conditions that promote minimal differentiation (13).

Western Blot Analysis

DNA topoisomerase IIα protein expression was examined with a mouse anti-human DNA topoisomerase IIα antibody (DAKO, Glostrup, Denmark) in 3 µg of total cellular protein from untreated ex vivo-expanded CD34+ cells and compared to that in the hematopoietic cell lines RS4:11, SEM-K2 and K562 (14-16). Protein concentrations were measured using the RCDC protein assay kit (Biorad, Hercules, Calif.) and Western blot analysis was performed with the Western Breeze kit (Invitrogen, Carlsbad, Calif.). The filter was simultaneously hybridized to a mouse anti-human β-actin antibody (Abcam, Cambridge, Mass.).

Real-Time PCR Analysis of DNA Topoisomerase IIα mRNA Expression

Quantitative real-time PCR analysis was performed on 10 ng of cDNA prepared from total RNA from untreated ex vivo-expanded CD34+ cells by 'Assays on Demand' for DNA topoisomerase IIα and GAPDH (Applied Biosystems, Foster City, Calif.) and compared to that in cultured hematopoietic cell lines using $2^{-\Delta\Delta C_t}$ analysis of relative gene expression data (17).

ICE (In Vivo Complex of Enzyme) Bioassay

Modified ICE assays were performed exactly as described (11). Five×10$^6$ ex vivo expanded CD34+ cells were incubated without drug or with 100 µM final concentration of etoposide at 37° C. in 2 ml of HPGM medium for 2 hours. Percentages of viable cells were assessed by Trypan Blue exclusion. Treated and untreated cells were pelleted and lysed as described (11). After flash-freezing and thawing at 37° C., the DNA was sheared by passage through a 25$_{1/2}$ G needle. Supernatants were collected and layered onto a CsCl cushion, and total genomic DNA including protein-bound DNA was isolated by ultracentrifugation at 80,000×g in an NVT90 rotor (Beckman; Palo Alto, Calif.) (11). The pellet was dissolved in 200 µl of 10 mM Tris-HCl (pH 8.0) 1 mM EDTA buffer, the DNA was quantified and 5.6 µg of DNA was analyzed on a Western blot with a mouse anti-human DNA topoisomerase IIα antibody (DAKO, Glostrup, Denmark) to detect DNA topoisomerase IIα-bound DNA (11).

Affinity Column Purification of DNA-DNA Topoisomerase IIα Covalent Complexes and Detection of MLL-Bound DNA Topoisomerase IIα

Each 1 ml affinity column consisted of Protein A-Sepharose Beads (Pharmacia Biotech, Upsala, Sweden) covalently coupled to mouse anti-human DNA topoisomerase IIα antibody (DAKO, Glostrup, Denmark) in PBS/0.02% sodium azide (18). The column was pre-washed with 10 volumes of 1×PBS. Total genomic DNA samples including protein-bound DNA from 32.5×10$^6$ untreated or etoposide-treated ex vivo-expanded human CD34+ cells was prepared according to the ICE assay protocol and diluted to a volume of 10 ml with cold 1×PBS. Samples were pre-cleared by incubation with Protein A Sepharose for 30 min while rotating at 4° C. in a 15 ml conical tube (18) and then centrifuged at 1200 rpm for 5 min in a Beckman G6 low-speed centrifuge. Supernatants were transferred to clean 15 ml conical tubes and incubated with the 1 ml of anti-human DNA topoisomerase IIα antibody-conjugated beads for 2 hrs while rotating at 4° C. and then run by gravity flow over affinity columns, followed by washing of the columns with 10 volumes of cold 1×PBS. Antibody-bound DNA topoisomerase IIα-DNA complexes from the untreated and etoposide-treated CD34+ cells were eluted with 1 ml of 100 mM glycine pH 2.7 and collected in 1.5 ml Eppendorf tubes containing a few drops of 1×PBS pH 11 for neutralization (18). The eluted material was PCI-extracted, ethanol-precipitated with NaOAc, washed with 70% EtOH and resuspended in 25 µl of dH$_2$0 and 1 µl was subjected to degenerative oligonucleotide PCR (DOP) using the primer 5'-CCGACTC-GAGNNNNNNNATGTGG-3' (SEQ ID NO: 251) (19) to generate template DNAs in sufficient quantity for real-time PCR. The products were quantified by OD$_{260}$ measurements and their sizes determined on an agarose gel.

MLL bcr primers for real-time PCR were selected using Primer Express v. 2.0 software, and their specificity confirmed using the BLAST algorithm. Forward and reverse primers 5'-ATAGTTTGTGTATTGCCAAGTCTGTTG-3' (SEQ ID NO: 252) and 5'-GGCGCTCGTTCTCCTCTAAA-3' (SEQ ID NO: 253), respectively, spanned MLL bcr positions 6784 to 6851 at the junction of intron 8-exon 9. The primer pair 5'-ACCACCGGGACCGCTACT-3' (SEQ ID NO: 254) and 5'-GTGGCCCTAAGACATGATCAACT-3' (SEQ ID NO: 255), was designed to amplify a genomic region of MLL exon 25, and a genomic region of GAPDH was examined by an intra-exon 'Assay on Demand' (Applied Biosystems); these genomic regions are not involved in MLL translocations. MGB oligonucleotide fluorogenic probes, which were synthesized by Applied Biosystems, were non-overlapping with the respective primer pairs and were designed according to Applied Biosystems guidelines using Primer Express v. 2.0 (20-23). Fluorogenic probe sequences for the amplicons at the MLL intron 8-exon 9 junction and MLL exon 25, respectively, were 5'-CCCTTCCACAAGTTTT-3' (SEQ ID NO: 256) and 5'-ATCTTGAATCAAGTGCCAAA-3' (SEQ ID NO: 257). Real-time PCR reactions were performed in duplicate in a MicroAmp 96-well plate using 50 ng of DOP-generated template, and the ABI Prism 7700 Sequence Detection System was used to examine product accumulation.

The following examples are provided to illustrate various embodiments of the present invention. They are not intended to limit the invention in any way.

EXAMPLE I

Identification and Tracing of Translocation Breakpoint Sequences in Leukemias in Patients, and Evidence from In Vitro Assays to Suggest that Translocation Breakpoints are Topoisomerase Ii Cleavage Sites Therapy, Clinical Course and Detection of MLL-AF-4 Translocation in Sequential Bone Marrow Specimens of Patient t-120

In patient t-120, rearrangements consistent with both derivative chromosomes from the t(4; 11) translocation were detected by Southern blot analysis in the bone marrow from ALL diagnosis, and both breakpoint junctions were characterized by panhandle PCR approaches (Raffini et al., 2002). The clinical course, primary neuroblastoma therapy and molecular analyses are summarized in FIG. 1A. All available sequential bone marrows were examined for the presence of the translocation. The translocation also was detectable by Southern blot at 9 months from the start of treatment. The translocation was not detectable by Southern blot analysis in the cells used for autologous marrow rescue or in any other marrow samples (FIG. 1B, 1C). By first-round PCR analysis of the der(4) breakpoint junction in 200 ng genomic DNA prepared from cryopreserved sequential bone marrow samples (~20,000 cell equivalent), only the marrows at 9 months after neuroblastoma diagnosis and at ALL diagnosis contained the translocation. By nested PCR (FIG. 1B, 1C) the translocation also was detectable in the marrow from 6 months after neuroblastoma diagnosis, after all 7 chemotherapy cycles and bone marrow harvest. This was before local radiation therapy, radiolabeled 3F8 monoclonal antibody and autologous marrow rescue, 5 months before leukemia was diagnosed. Spiking DNA from the ALL sample into peripheral blood lymphocyte DNA from a normal subject and serial dilutions indicated that the sensitivity of the nested PCR for detection of the translocation was between 1 cell in $10^5$ and 1 cell in $10^6$ cells.

Chemotherapy Enhances DNA Topoisomerase II Cleavage at MLL and AF-4 Genomic Translocation Breakpoints in all of Patient t-120

From prior sequencing the der(11) MLL breakpoint was position 6588 or 6589 in intron 8 and the der(11) AF-4 breakpoint was position 7130 or 7131 in intron 3. The der(4) AF-4 breakpoint was position 7108, 7109 or 7110 in intron 3 and the der(4) MLL breakpoint was position 6594, 6595 or 6596 in intron 8 (Raffini et al., 2002). Although 'A' nucleotides at the breakpoints in both genes at the der(11) breakpoint junction and 5'-CA-3' sequences at the breakpoints in both genes at the der(4) breakpoint junction precluded more precise breakpoint assignments, 4-7 bases and 19-22 bases, respectively, were deleted from MLL and AF-4 (Raffini et al., 2002).

These near-precise recombinations with few bases lost relative to the normal sequences indicated that the translocation breakpoints were in close proximity to the sites of damage. The first molecular detection of the translocation was after all 7 chemotherapy cycles, which included etoposide and doxorubicin as DNA topoisomerase II poisons. Therefore, DNA topoisomerase II in vitro cleavage assays were performed without drug or with etoposide, its catechol or quinone metabolites or doxorubicin on double stranded DNA substrates containing the normal homologues of the respective MLL (FIG. 2A, 2C) and AF-4 (FIG. 2B, 2D) translocation breakpoints to locate where the drugs to which the patient was exposed stimulated cleavage complexes. DNA topoisomerase II creates staggered nicks in duplex DNA with 4-base 5' overhangs (Fortune and Osheroff, 2000); cleavage site locations were defined by the base at the 5' side of cleavage (−1 position) on the sense strand of DNA. DNA topoisomerase II cleavage sites in MLL (FIG. 2A, 2C) and AF-4 (FIG. 2B, 2D) were identified at or proximal to the translocation breakpoints.

Because the der(11) and der(4) MLL breakpoints were at a hotspot for translocation breakpoints in treatment-related leukemia, cleavage assays of the relevant MLL substrate with all drugs at 20 µM final concentration had already been performed (Whitmarsh et al., 2003). In the present study, however, doxorubicin was studied over a range of concentrations (FIG. 2C) because of its dual effects of cleavage stimulation at low concentrations and DNA topoisomerase II catalytic inhibition due to intercalation at high concentrations (Capranico and Binaschi, 1998). MLL bcr position 6588 ranked $5^{th}$ of 8 cleavage sites detected without drug in the MLL substrate (Whitmarsh et al., 2003). Etoposide, etoposide catechol and etoposide quinone each at 20 µM, enhanced cleavage at this site 7.9-, 4.4- and 9.8-fold, respectively, over cleavage without drug (FIG. 2A). The especially strong cleavage detected at this position ranked $3^{rd}$ of cleavage sites in the substrate in the presence of etoposide quinone (FIG. 2A) (Whitmarsh et al., 2003). The enzyme-only cleavage and cleavage with etoposide or its metabolites at position 6588 remained detectable after heating, indicating resistance to relegation and stability of the cleavage complexes. Although position 6588 was one of only two cleavage sites detected with doxorubicin at 20 µM, the cleavage was weak compared to enzyme-only cleavage (0.4-fold), indicating catalytic inhibition at high concentration (FIG. 2A). At concentrations from 0.01 µM to 0.5 µM doxorubicin resulted in dose-dependent increases over enzyme-only cleavage at MLL bcr position 6588 consistent with poisoning effects, whereas the cleavage enhancement at this site began to decrease at 2.5 µM (FIG. 2C). Thus the intercalating agent doxorubicin has site-specific, concentration-dependent, mixed effects of a poison and a catalytic inhibitor of DNA topoisomerase II at this position in the MLL translocation breakpoint hotspot region. In contrast, at positions 6587 and 6589, only catalytic inhibition was observed at all concentrations tested (FIG. 2C).

Figure 2B:
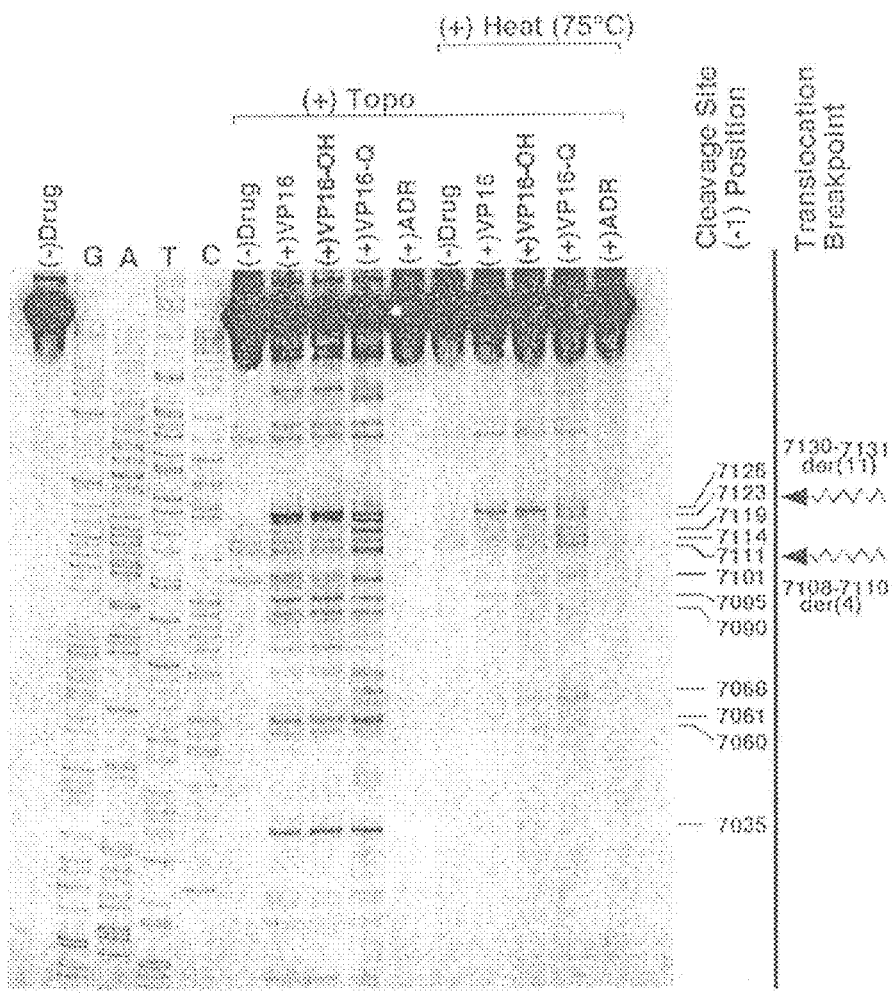
Figure 2C:
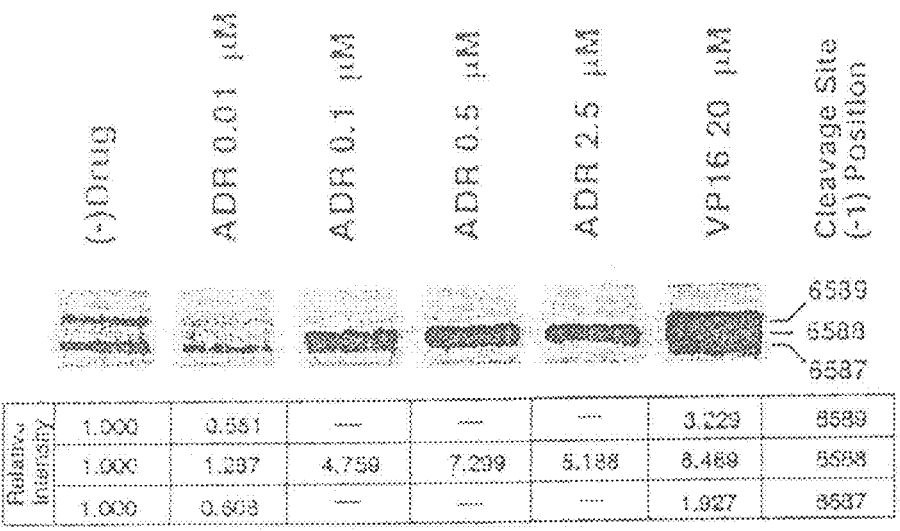
FIGS. 2C and 2D demonstrate the effects of doxorubicin over a range of concentrations on the cleavage of the MLL (FIG. 2C) and AF-4 (FIG. 2D) substrates.
Figure 2D:
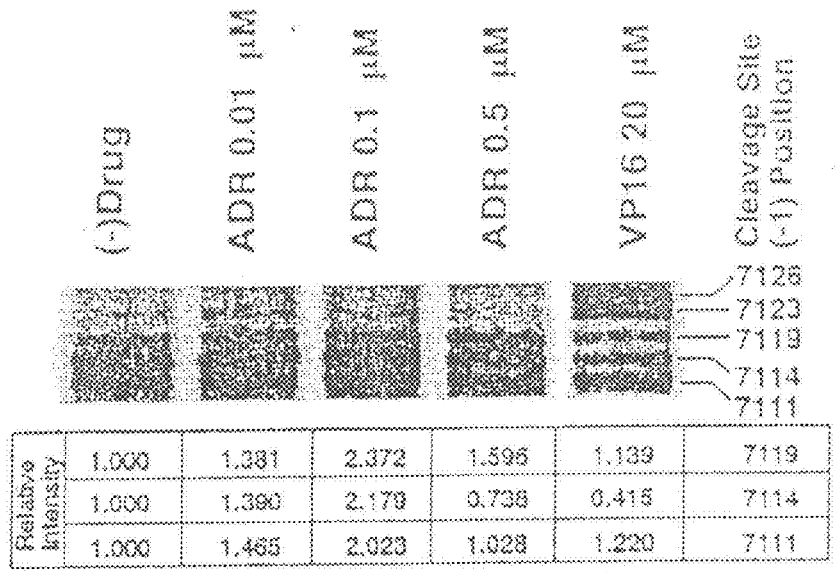

In the AF-4 intron 3 substrate spanning positions 6956 to 7239, there was no detectable cleavage at position 7126 without drug or with doxorubicin at 20 µM (FIG. 2B) or lower concentrations (FIG. 2D), but cleavage at this position ranked first in relative intensity among all cleavage sites with etoposide and etoposide catechol and $5^{th}$ among all cleavage sites with etoposide quinone (FIG. 2B). There was 3.2-, 5.9- and 3.4-fold cleavage at position 7126 in the presence of etoposide, etoposide catechol and etoposide quinone, respectively, relative to the strongest enzyme-only cleavage in the substrate, which occurred at position 7114. Cleavage at position 7126 in the presence of etoposide and both etoposide metabolites were not only especially strong, but also especially heat-stable. Examination of doxorubicin-associated cleavage over a range of concentrations with particular attention to the region of the breakpoints showed dose-dependent increases in cleavage stimulation over enzyme-only cleavage at AF-4 intron 3 positions 7111, 7114 and 7119, consistent with poisoning effects, while cleavage at these sites began to decrease at 0.5 µM, consistent with the mixed effect of catalytic inhibition (FIG. 2D).

Processing of DNA Topoisomerase II Cleavage Sites Enhanced by Etoposide or its Metabolites or Doxorubicin Forms Both Genomic Breakpoint Junctions in all of Patient t-120

Figure 3A:
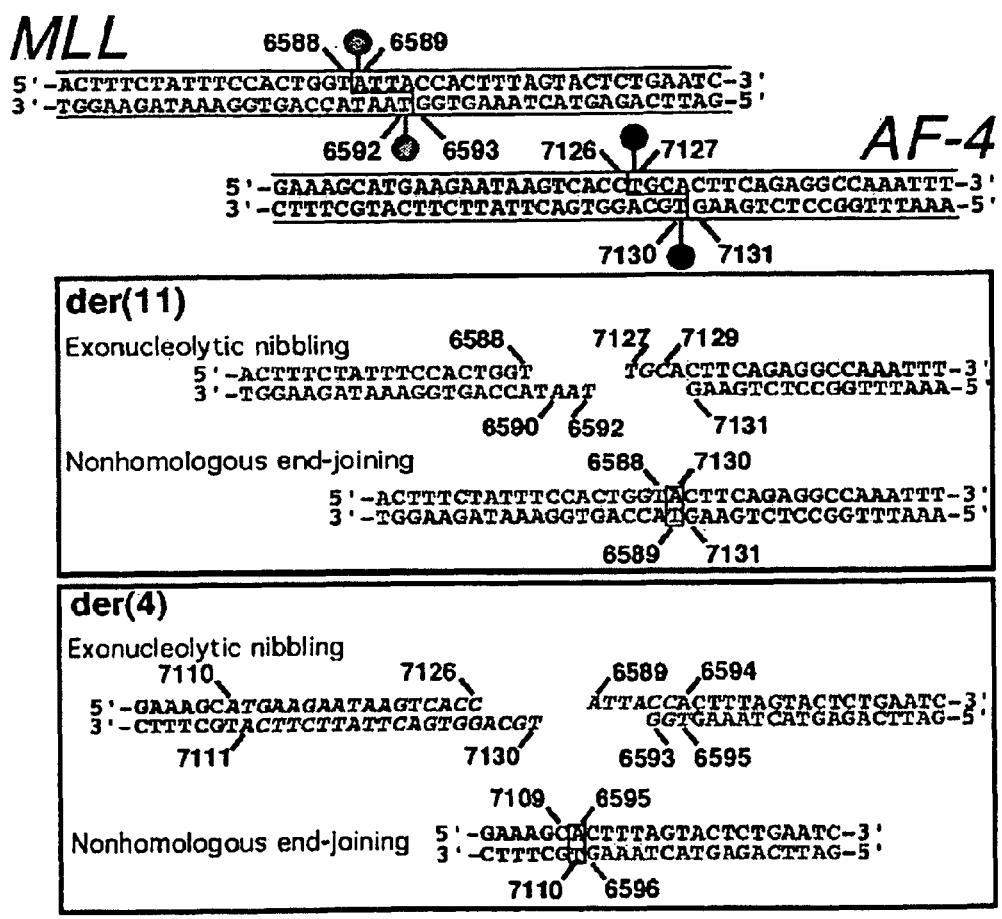
FIGS. 3A and 3B are schematic drawings of models for processing of cleavage sites to form der(11) and der(4) genomic breakpoint junctions in ALL of patient t-120.

The model shown in FIG. 3A for formation of the observed der(11) and der(4) genomic breakpoint junctions was derived from the cleavage sites at MLL bcr position 6588, which was enhanced by etoposide, both etoposide metabolites and doxorubicin, and AF-4 intron 3 position 7126, which was enhanced by etoposide and both etoposide metabolites but not doxorubicin. Processing of the 4-base 5' overhangs from DNA topoisomerase II cleavage at these sites would generate the der(11) and der(4) sequences observed in the leukemia. In the model shown, exonucleolytic nibbling creates single-base homologies and base-pairing promotes the formation of both breakpoint junctions by error-prone nonhomologous end joining (NHEJ). Consistent with the genomic sequencing and relative to the sense strands, 6 bases from MLL and 20 bases from AF-4 are lost during the processing, MLL bcr position 6588 and AF-4 intron 3 position 7130 are joined to form the der(11), and AF-4 intron 3 position 7109 and MLL bcr position 6595 are joined to form the der(4) (FIG. 3A).

Figure 3B:
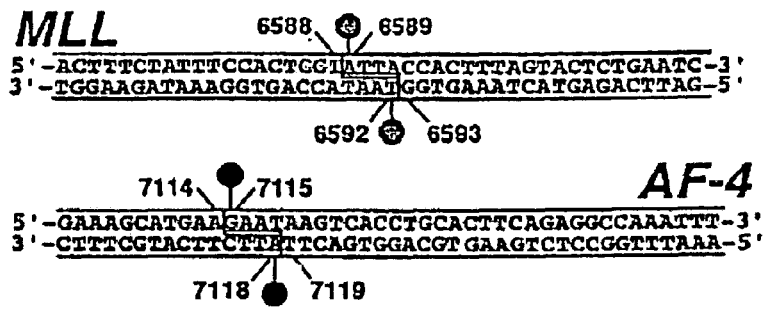
Figure 3B:
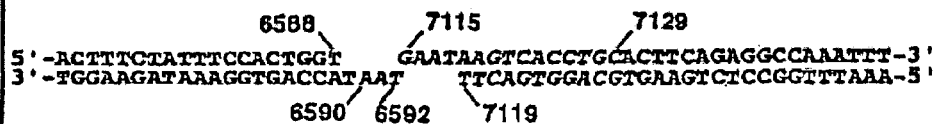
Figure 3B:
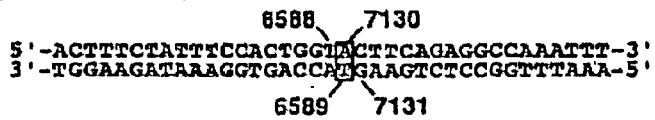
Figure 3B:
Figure 3B:
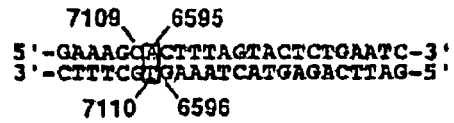

The especially strong doxorubicin-stabilized cleavage sites at MLL bcr position 6588 and AF-4 intron 3 position 7114 were used to develop the alternative model in FIG. 3B for formation of the observed der(11) and der(4) genomic breakpoint junctions by error-prone NHEJ. In this model, 6 bases from MLL and 20 bases from AF-4 relative to the sense strands again are lost during the processing (FIG. 3B), and the same bases in MLL bcr and AF-4 intron 3 as described above are joined to form both breakpoint junctions. These models demonstrate that interchromosomal recombination by repair of chemotherapy-stabilized DNA topoisomerase II cleavage could be the translocation mechanism in this ALL, although models using other DNA topoisomerase II cleavage sites proximal to the translocation breakpoints are possible as well (not shown). However, it cannot be determined in this case whether etoposide or its metabolites or doxorubicin led to the relevant damage resulting in the translocation in the leukemia in this patient since each compound stimulated strong DNA topoisomerase II cleavage complexes proximal to the breakpoints.

Therapy, Clinical Course and Molecular Detection of MLL-GAS7 Translocation in Sequential Bone Marrow Specimens of Patient t-39

Patient t-39 was a 13-year old boy with stage 4 neuroblastoma treated with 4 cycles of cyclophosphamide, doxorubicin and vincristine (CAV), 1 cycle of cyclophosphamide and doxorubicin in which vincristine was omitted for toxicity, 3 cycles of cisplatin and etoposide (PVP), surgical resection, local radiation, and 3F8 monoclonal antibody with GM-CSF (Megonigal et al., 2000). The clinical diagnosis of secondary AML and molecular analyses of sequential bone marrow samples relative to the neuroblastoma treatment have been described (Megonigal et al., 2000). The MLL translocation was not PCR-detectable at neuroblastoma diagnosis, but was detectable by clonotypic PCR analysis of the der(11) genomic breakpoint junction in all marrow specimens obtained at and after 6 weeks from the start of treatment, which was after two cycles of CAV (Megonigal et al., 2000). AML was diagnosed 15.5 months after the translocation was PCR-detectable (Megonigal et al., 2000).

MLL and GAS7 Genomic Translocation Breakpoints in AML of Patient t-39 are Proximal to Doxorubicin-Stabilized DNA Topoisomerase II Cleavage Sites From previously described genomic sequencing, the der (11) MLL breakpoint in the treatment-related AML was position 4662, 4663, or 4664 in intron 8 and the der(11) GAS7 breakpoint was position 1240, 1241 or 1242 upstream of exon 1 (Megonigal et al., 2000). MLL positions 4663-4664 and GAS7 positions 1240-1241 were 5'-AT-3', precluding more precise breakpoint assignments (Megonigal et al., 2000). The der(17) GAS7 breakpoint was position 1203 and the der(17) MLL breakpoint was position 4680 (Megonigal et al., 2000). 15-17 bp from MLL and 36-38 bp from GAS7 were deleted during this translocation (Megonigal et al., 2000). The involved region of MLL was more 5' in the bcr and was not the translocation breakpoint hotspot.

Figure 4A:
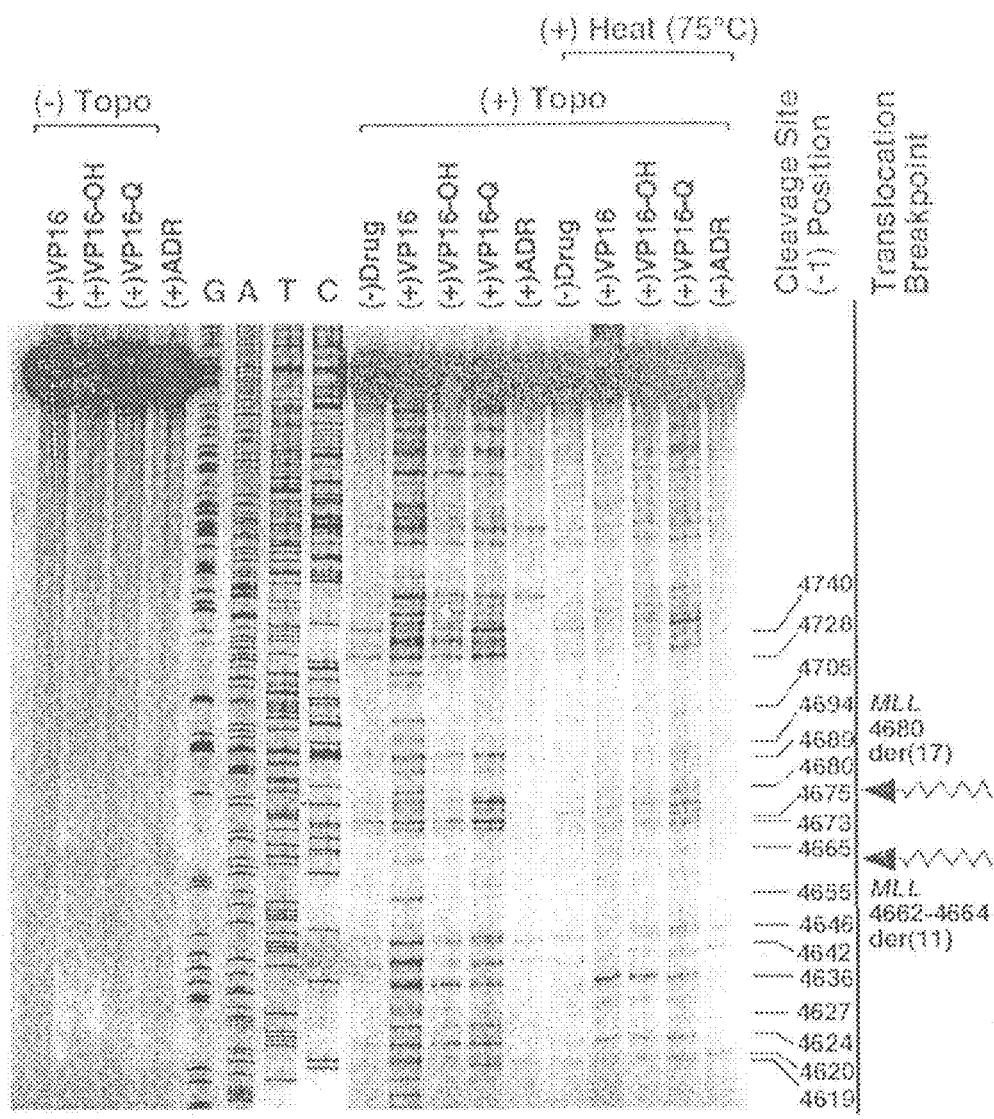
FIGS. 4A and 4B are images of autoradiographs of normal homologues of MLL (FIG. 4A) and GAS7 (FIG. 4B) genomic breakpoint sequences in acute myeloid leukemia (AML) of patient t-39 in DNA topoisomerase II in vitro cleavage assays. DNA topoisomerase II cleavage of MLL intron 8 coordinates 4589 to 4768 and GAS7 coordinates 1129 to 1440 upstream of exon 1.
Figure 4B:
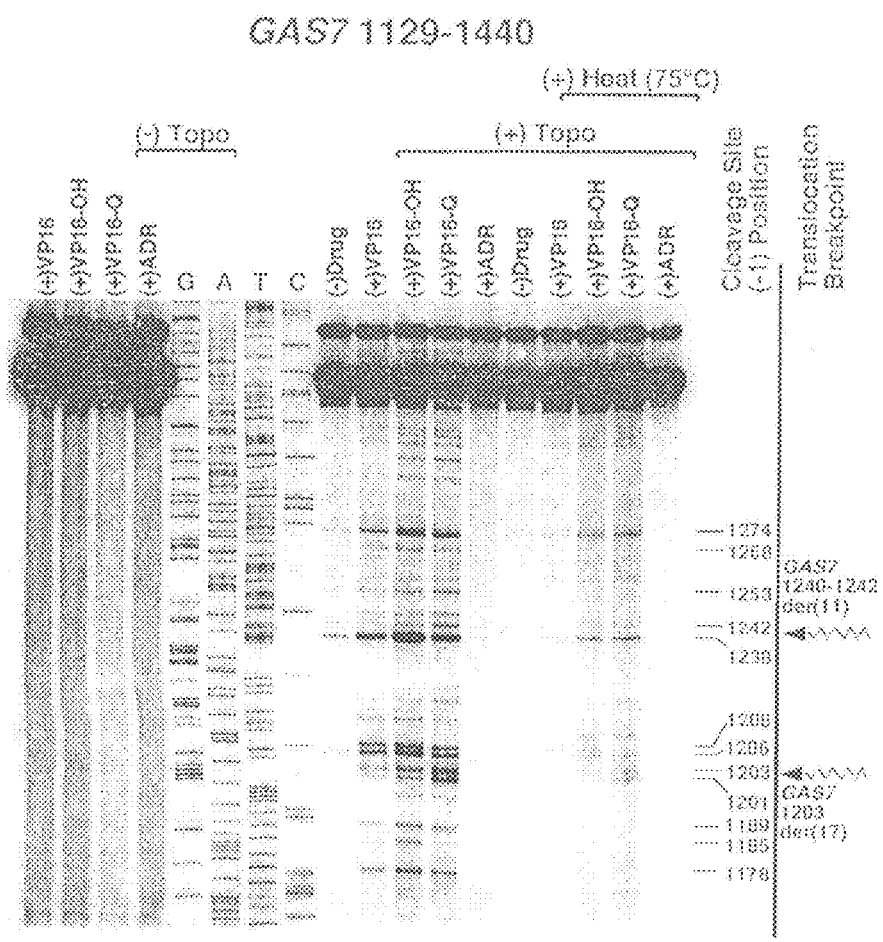
Figure 4C:
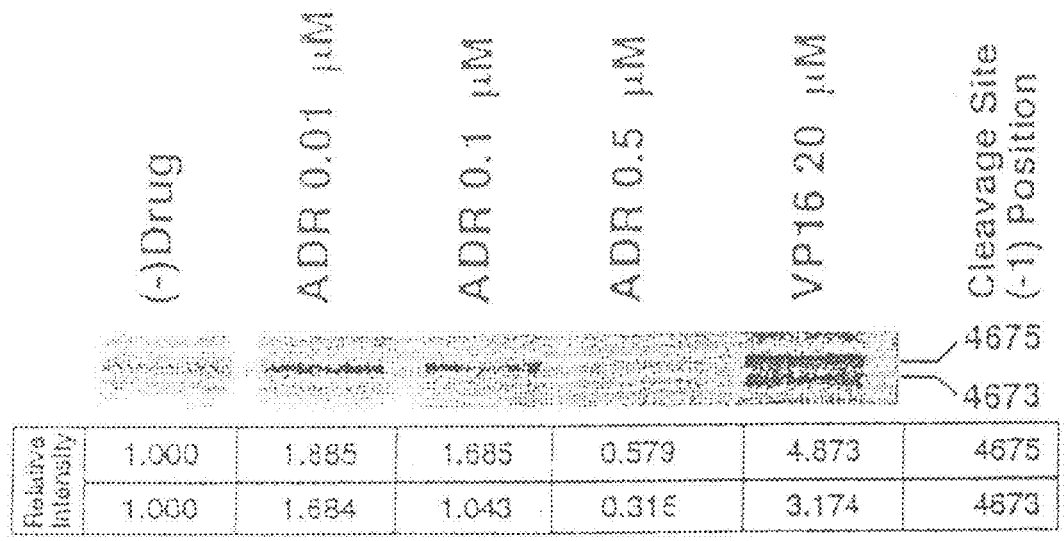
FIGS. 4C and 4D demonstrate the effects of doxorubicin over a range of concentrations on the cleavage of the MLL at position 4673 and 4675 (FIG. 4C) and GAS7 at position 1238 (FIG. 4D).
Figure 4D:
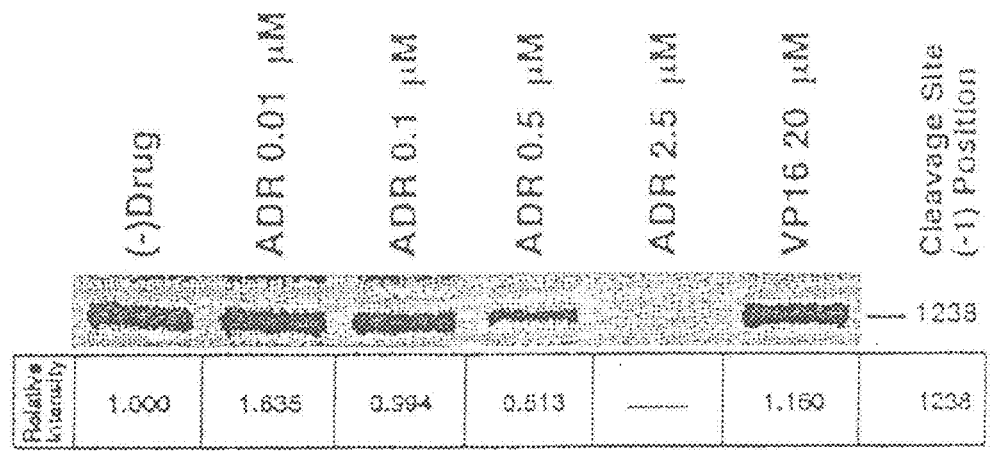

Although doxorubicin was the only DNA topoisomerase II poison to which the patient was exposed before molecular emergence of the translocation (Megonigal et al., 2000), DNA topoisomerase II in vitro cleavage assays were performed without drug, with doxorubicin or, as references for cleavage site intensities, with etoposide or its metabolites. The translocation breakpoints were near strong, enzyme-only cleavage sites at MLL bcr position 4675 (FIG. 4A) and GAS7 position 1238 (FIG. 4B) that were enhanced substantially by doxorubicin at low concentrations (FIG. 4C, 4D). In the MLL bcr substrate, the enzyme-only cleavage at position 4675 was 0.27-fold relative to cleavage with etoposide, and this position ranked $3^{rd}$ among all enzyme-only cleavage sites (FIG. 4A). GAS7 position 1238, where the enzyme-only cleavage was 0.44-fold relative to cleavage with etoposide, was the strongest enzyme-only cleavage site in the GAS7 substrate (FIG. 4B). The enzyme-only cleavage complexes at MLL bcr position 4675 and GAS7 position 1238 were highly heat-resistant (FIG. 4A, 4B), indicating these cleavage complexes were particularly stable. Consistent with behavior as a poison, doxorubicin at 0.01 µM was associated with quantifiably enhanced cleavage over the already very strong enzyme-only cleavage, not only at MLL bcr position 4675, but also at MLL bcr position 4673 (FIG. 4C) and GAS7 position 1238 (FIG. 4D). The site-specific enhancement of cleavage over enzyme-only cleavage at these sites in the presence of doxorubicin began to decrease at 0.1 µM (FIG. 4C, D) and there was complete diminution at 20 µM (FIG. 4A, 4B), indicating mixed effects of a poison and catalytic inhibitor of DNA topoisomerase II.

Processing of Doxorubicin-Stabilized DNA Topoisomerase II Cleavage Sites in MLL and GAS7 Generates Genomic Breakpoint Junctions in AML of Patient t-39

Figure 5:
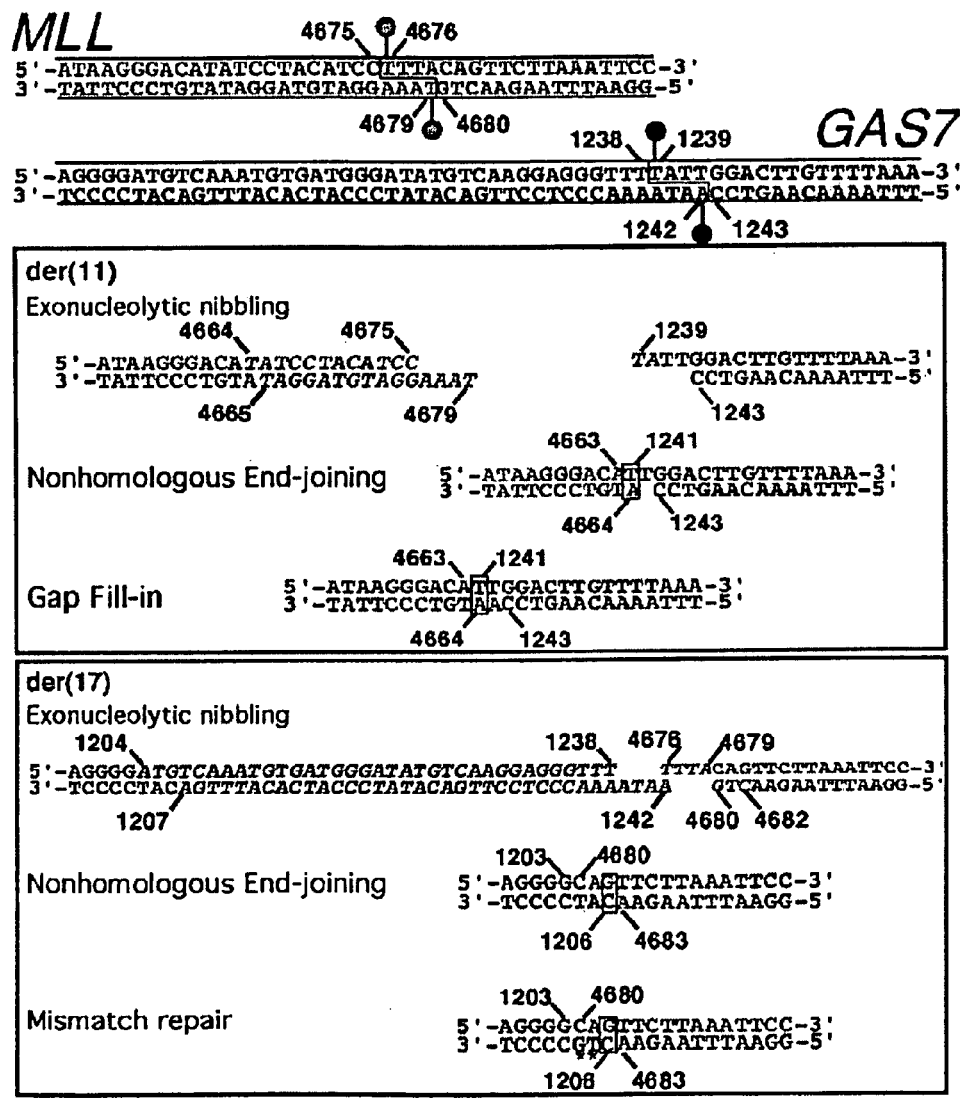
FIG. 5 is a schematic drawing of a model for processing of DNA topoisomerase II cleavage sites that were detected without drug and enhanced greatly with low concentration doxorubicin, (the only DNA topoisomerase II targeted drug to which the patient was exposed before molecular detection of the translocation) to form der(11) (top strand is SEQ ID NO: 264; bottom strand is SEQ ID NO: 270) and der(17) (top strand is SEQ ID NO: 265; bottom strand is SEQ ID NO: 271) genomic breakpoint junctions in AML of patient t-39. Both genomic breakpoint junctions are formed by resolution of doxorubicin-stimulated DNA topoisomerase II cleavage sites via error-prone nonhomologous end-joining (NHEJ). DNA topoisomerase II cleavage sites at MLL (fragment shown: top strand is SEQ ID NO: 262; bottom strand is SEQ ID NO: 272) intron 8 position 4675 and GAS7 (fragment shown; top strand is SEQ ID NO: 263; bottom strand is 273) position 1238 with 4-base 5' overhangs are shown at the top. In formation of the der(11) positions 4664 to 4675 on the sense strand of MLL, positions 4665 to 4679 on the antisense strand of MLL and positions 1239 to 1240 on the sense strand of GAS7 are lost by exonucleolytic nibbling (italic, middle) before NHEJ (box, middle) and gap fill-in (black, middle) ensue (under exonucleolytic nibbling, left fragment: top strand is nucleotides 1-22 of SEQ ID NO: 262 and bottom strand is nucleotides 16-41 of SEQ ID NO: 272; right fragment: top strand is nucleotides 41-57 of SEQ ID NO: 263 and bottom strand is nucleotides 1-13 of SEQ ID NO: 273; for nonhomologous end-joining, top strand is 264, bottom left strand is nucleotides 31-41 of SEQ ID NO: 272, bottom right strand is nucleotides 1-13 of SEQ ID NO: 273). Positions 1204 to 1238 on the sense strand of GAS7, positions 1207 to 1242 on the antisense strand of GAS7, positions 4676 to 4679 on the sense strand of MLL and positions 4680 to 4682 on the antisense strand of MLL are lost by exonucleolytic nibbling (italic, bottom) and the der(17) forms by NHEJ (box, bottom) and mismatch repair (asterisks, bottom; under exonucleolytic nibbling, left fragment: top strand is nucleotides 1-40 of SEQ ID NO: 263 and bottom strand is nucleotides 14-57 of SEQ ID NO: 273; right fragment: top strand is nucleotides 23-41 of SEQ ID NO: 262 and bottom strand is nucleotides 1-15 of SEQ ID NO: 272; for nonhomologous end-joining, top strand is 265, bottom strand is SEQ ID NO: 274).

A model for processing of the doxorubicin-stimulated cleavage sites at MLL intron 8 position 4675 and GAS7 position 1238 to form both genomic breakpoint junctions in the AML of patient t-39 is shown in FIG. 5. Exonucleolytic nibbling of the indicated bases (italic, middle) creates a single-base homology (box, middle), and NHEJ and gap fill-in ensue, resulting in the der(11) breakpoint junction. The processing to create the observed der(17) genomic breakpoint junction also includes exonucleolytic nibbling (italic, bottom) to form a single-base homology (box), followed by NHEJ and mismatch repair (bottom). Relative to the sense sequences, the exonucleolytic nibbling in the model results in loss of 16 bases from MLL and 37 bases from GAS7 during processing of the overhangs from the cleavage (FIG. 5). MLL bcr position 4663 and GAS7 position 1241 are joined to form the der(11), and GAS7 position 1203 and MLL bcr position 4680 are joined to form the der(17), which is consistent with prior genomic sequencing of the breakpoint junctions in the AML (Megonigal et al., 2000).

EXAMPLE II

Figure 6:
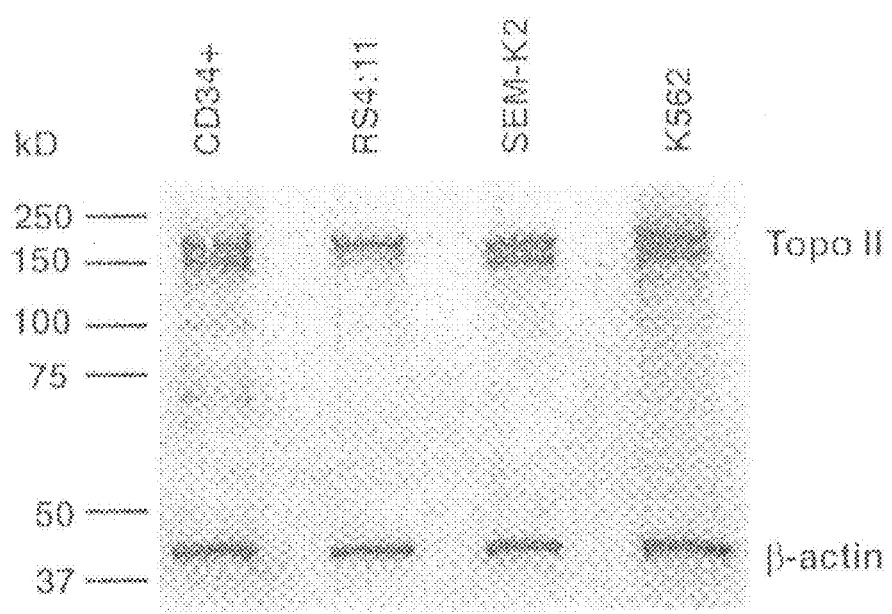
FIG. 6 is an image of a Western blot analysis of DNA topoisomerase IIα protein expression in ex vivo-expanded CD34+ cells and cultured hematopoietic cell lines. 3 µg of protein per lane were loaded on the gel. The filter was simultaneously hybridized to mouse anti-human DNA topoisomerase IIα (DAKO, Glostrup, Denmark) and mouse anti-human β-actin (Abcam, Cambridge, Mass.) antibodies.

Hematopoietic Progenitor Cells—a Model Cellular System for Analysis of Chromosomal Translocations Mediated by Elevated Expression of Topoisomerase II Characterization of Native DNA Topoisomerase IIα mRNA and Protein Expression in Human CD34+ Cells By quantitative real-time PCR analysis, DNA topoisomerase IIα mRNA expression in the cell lines RS4:11, SEM-K2 and K562 cells was 1.54(1.16±2.03)-fold, 1.55 (1.14–2.10)-fold and 2.75(2.53–2.99)-fold relative to ex vivo-expanded human CD34+ cells (Table 1), indicating that DNA topoisomerase IIα mRNA in proliferating bone marrow stem cells is in the range of that in hematopoietic cell lines. Western blot analysis suggested that DNA topoisomerase IIα protein expression in the ex vivo-expanded human CD34+ cells was also high and comparable to that in hematopoietic cell lines (FIG. 6).

TABLE 1

Relative DNA topoisomerase IIα mRNA expression in leukemia cell lines compared to CD34+ cells

| Cells | DNA topoisomerase IIα $C_T$ (Avg. ± S.D.) | GAPDH $C_T$ (Avg. ± S.D.) | $\Delta C_T$ (Avg. DNA topoisomerase IIα $C_T$ – Avg. GAPDH $C_T$) | $\Delta\Delta C_T$ (Avg. $\Delta C_T$ – Avg. $\Delta C_{T\ CD34+\ cells}$) | Normalized DNA topoisomerase IIα amount relative to CD34+ cells $2^{-\Delta\Delta C_T}$ |
|---|---|---|---|---|---|
| CD34+ cells | 25.69 ± 0.26 | 20.58 ± 0.06 | 5.11 ± 0.23 | 0 | 1 |
| RS4: 11 | 25.28 ± 0.38 | 20.79 ± 0.15 | 4.49 ± 0.40 | −0.62 ± 0.40 | 1.54 (1.16-2.03) |
| SEM-K2 | 24.50 ± 0.28 | 20.02 ± 0.18 | 4.48 ± 0.44 | −0.63 ± 0.44 | 1.55 (1.14-2.10) |
| K562 | 25.61 ± 0.23 | 21.96 ± 0.12 | 3.65 ± 0.12 | −1.46 ± 0.12 | 2.75 (2.53-2.99) |

EXAMPLE III

Figure 7A:
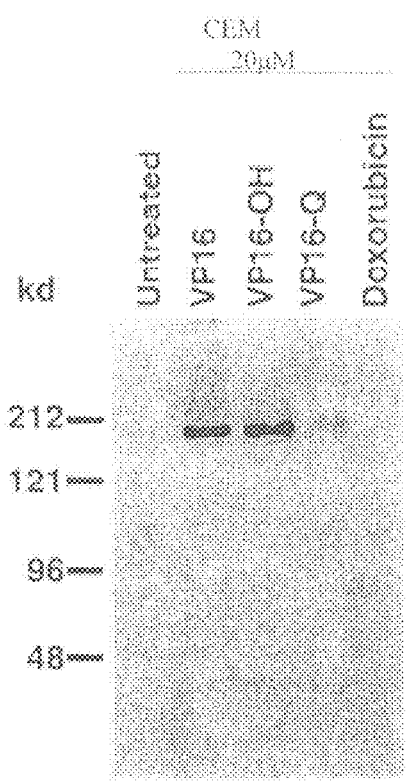
FIGS. 7A through 7D are images of Western blots demonstrating DNA topoisomerase II-DNA complex formations in the presence of various drugs at various concentrations in a modified ICE bioassay. The assays were performed on CEM cells (FIG. 7A), K562 cells (FIGS. 7B and 7C), and KG-1 cells (FIG. 7D). Etoposide (VP16), etoposide catechol (VP16-OH), etoposide quinone (VP16-Q), and doxorubicin were tested.
Figure 7B:
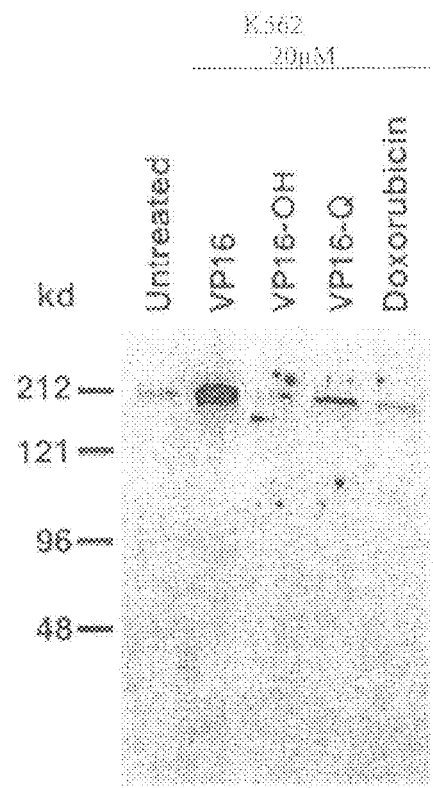
Figure 7C:
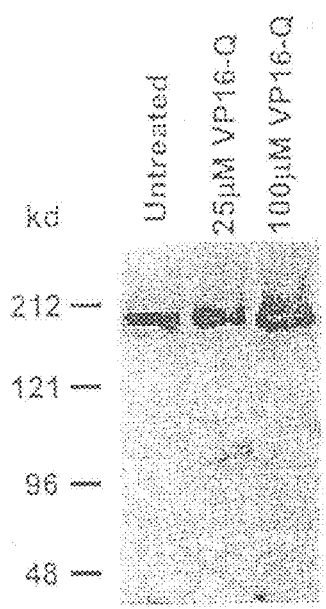
Figure 7D:
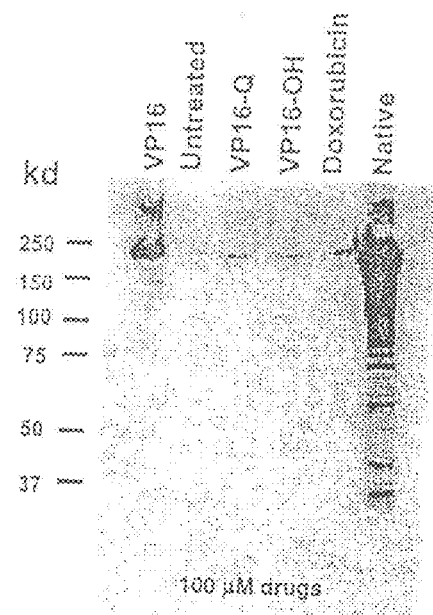

ICE Bioassay Detects Topoisomerase-DNA and Topoisomerase-DNA-Drug Covalent Complexes in Total Genomic DNA of Hematopoietic Cell Lines and CD34 Cells DNA Topoisomerase II Covalent Complexes are Detected in Hematopoietic Cell Lines Treated with Chemotherapy Although etoposide has been previously studied in ICE assays of, e.g., the hematopoietic cell line CEM, induction of DNA topoisomerase II cleavage complexes by etoposide metabolites had not been previously studied in a cellular context. A modified in vivo complex of enzyme (ICE) bioassay was employed to determine whether etoposide metabolites induce DNA topoisomerase II covalent complexes in the chromatin context of hematopoietic cell lines (11). The assay entails trapping the DNA covalently bound to DNA topoisomerase II by phosphotyrosine linkage using protein denaturants and detection on a Western blot. Isolation of the protein-bound DNA using a CsCl cushion, as elaborated by Topogene, streamlines the methodology compared to previous methods. In addition, the approach was changed further from use of the slot blot analysis to detect the cleavage complexes to detection of the complexes by Western blot analysis, which enables size separation of the DNA-protein complexes. ICE bioassays demonstrated significant induction of DNA topoisomerase II cleavage complexes in CEM cells after treatment for 2 hours with etoposide or its catechol or quinone metabolites at 20 μM (FIG. 7A). The cleavage complexes induced by etoposide catechol were comparable in amount to the parent drug. Induction of DNA cleavage complexes was also observed in K562 cells treated with 20 μM etoposide or etoposide quinone (FIG. 7B). Consistent with the presence of DNA bound to the enzyme, the DNA topoisomerase IIα protein ran higher than its known molecular weight of 170 kDa. Notably, no induction of DNA topoisomerase II cleavage complexes was detected in either CEM or K562 cells after treatment with doxorubicin at the same concentration within the sensitivity of the assay. However, doxorubicin is an intercalative DNA topoisomerase II poison that induces DNA topoisomerase II cleavage with different sequence site-selectivity (Capranico et al., 1990) and that also is associated with leukemia as a treatment complication, albeit less often (Sandoval et al., 1993). Its behavior as a site-specific poison of DNA topoisomerase II in in vitro assays of translocation breakpoints was established herein. Additional ICE assays in K562 cells showed a concentration dependent increase in the induction of DNA topoisomerase II cleavage complexes treated with etoposide quinone for 2 hours, consistent with its behavior as a DNA topoisomerase II poison (FIG. 7C). Unlike in CEM cells and K562 cells, in KG1 cells not only etoposide and its metabolites, but also doxorubicin at 100 μM induced DNA II covalent complexes (FIG. 7D).

Figure 8:
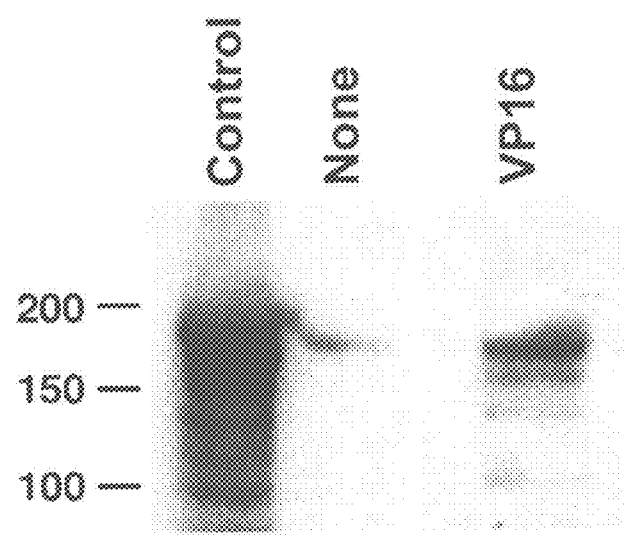
FIG. 8 is an image of a gel showing a modified in vivo complex of enzyme (ICE) assay of DNA topoisomerase II covalent complexes in ex-vivo expanded CD34+ cells. The cells were untreated or treated for 2 hours with etoposide at 100 µM final concentration. Total genomic DNA containing protein-bound DNA was isolated on a CsCl cushion and 5.6 µg per well was loaded on a 4-12% Bis-Tris gradient gel. An anti-human DNA topoisomerase IIα antibody (DAKO, Glostrup, Denmark) was used to detect DNA topoisomerase II covalent complexes. Recombinant human DNA topoisomerase IIα is in lane at the far left. The molecular weight of the topoisomerase II band is >170 kD, which is the molecular weight of topoisomerase II. This is consistent with DNA bound to the enzyme.

Native and Etoposide-Stabilized DNA Topoisomerase II Covalent Complexes are Detected in Ex Vivo Expanded Human CD34+ Cells ICE assays were performed on ex vivo expanded CD34+ cells from cadaveric human bone marrow that were either treated for 2 hours with etoposide or untreated. Cell viability assessed by Trypan blue exclusion was ~70% for both conditions. Results for the untreated cells and cells treated with etoposide at 100 μM final concentration are shown in FIG. 8. As predicted in proliferating cells (6), native DNA topoisomerase II covalent complexes were detected in the untreated cells. Etoposide treatment resulted in increased formation of DNA topoisomerase II covalent complexes. The DNA topoisomerase IIα protein ran higher than its known molecular weight of 170 kDa, which is consistent with the presence of DNA bound to the enzyme. Etoposide catechol treatment also showed increased formation of topoisomerase-DNA cleavage complexes in CD34+ cells.

EXAMPLE IV

Real-Time PCR with MLL Specific Primers Detects Topoisomerase-DNA and Topoisomerase-DNA-Drug Covalent Complexes with Specific Sequences in MLL Gene in Total Genomic DNA of Hematopoietic Cell Lines and CD34 Cells after Immunoaffinity Purification and DOP Amplification DNA Topoisomerase II Covalent Complexes with MLL bcr are Detected in Untreated and Etoposide-Treated Ex Vivo-Expanded CD34+ Cells A real-time PCR approach was developed to detect DNA topoisomerase II covalent complexes at the sequence level with the MLL breakpoint cluster region (bcr) in CD34+ cells. Total genomic DNA samples, including protein bound DNA from untreated or etoposide-treated, ex-vivo expanded human CD34+ cells, were prepared on CsCl cushions according to the ICE assay protocol. DNA-DNA topoisomerase IIα covalent complexes in the total genomic DNA were purified on an immuno-affinity column consisting of Protein A-Sepharose beads covalently coupled to a mouse anti-human DNA topoisomerase IIα antibody. The eluted material from the column was subjected to degenerative oligonucleotide PCR in order to generate template DNAs in sufficient quantity for real-time PCR. MLL bcr primers for real-time PCR were designed to amplify MLL bcr positions 6784 to 6851 at the junction of intron 8-exon 9 near the translocation breakpoint, which is in proximity to the hotspot region for translocation breakpoints occurring in cases of leukemia in patients exposed to DNA topoisomerase II poisons (Whitmarsh 2003) and, in at least one patient after chemotherapy without such agents (Langer 2003).

Figure 9A:
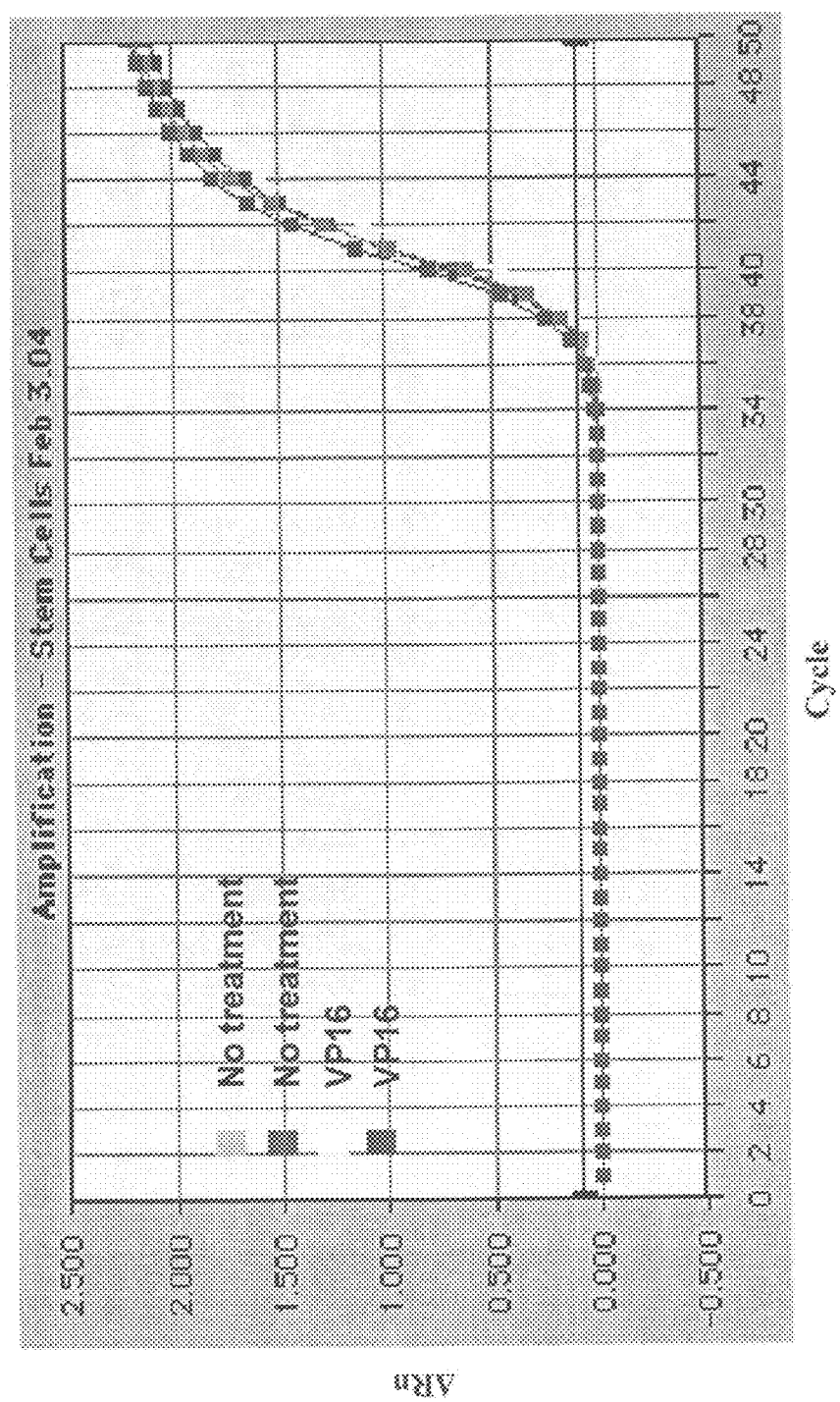
FIGS. 9A, 9B, 9C, and 9D are plots from the real-time PCR analysis of DNA topoisomerase II covalent complexes with MLL and other sequences. CD34+ cells were untreated or treated for 2 hours with etoposide at a 100 µM final concentration. Total genomic DNA containing protein-bound DNA was isolated on a CsCl cushion, and DNA topoisomerase IIα-bound DNA was purified on an immunoaffinity column and then amplified by degenerative oligonucleotide PCR (DOP). 50 ng of DOP products ranging from 500 bp to 1 kb in size served as a template for amplification in real-time PCR with primers specific for MLL intron 8-exon 9 (FIG. 9A), GAPDH (FIG. 9B), MLL exon 25 (FIG. 9C), or MLL intron7-exon 8 (FIG. 9D). Products were not detectable in duplicate reagent-control reactions for these amplicons. ΔRn (measure of reporter signal) v. cycles are shown in the plots.
Figure 9B:
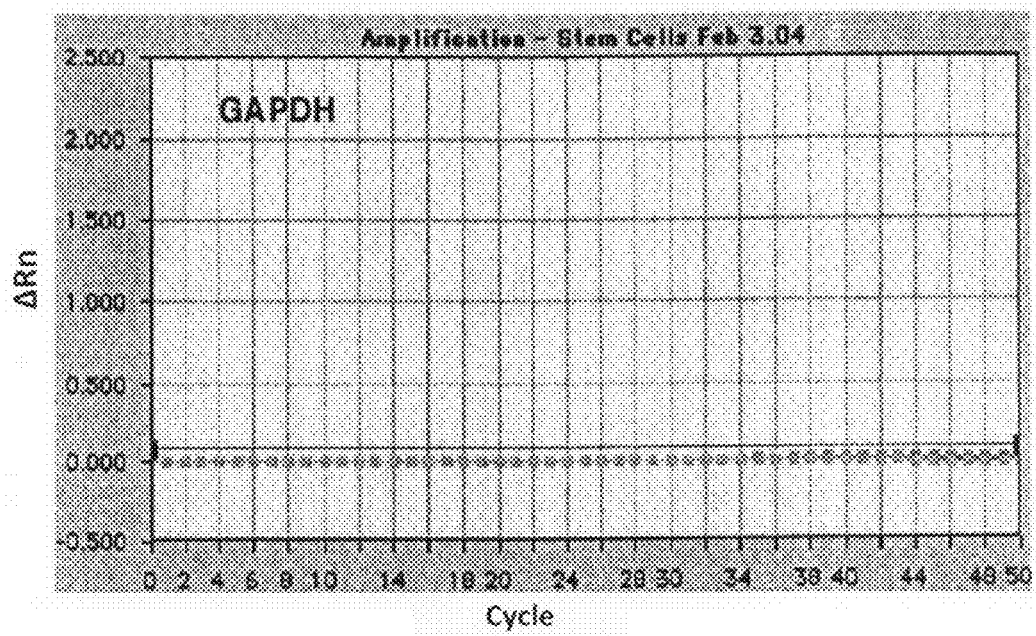
Figure 9C:
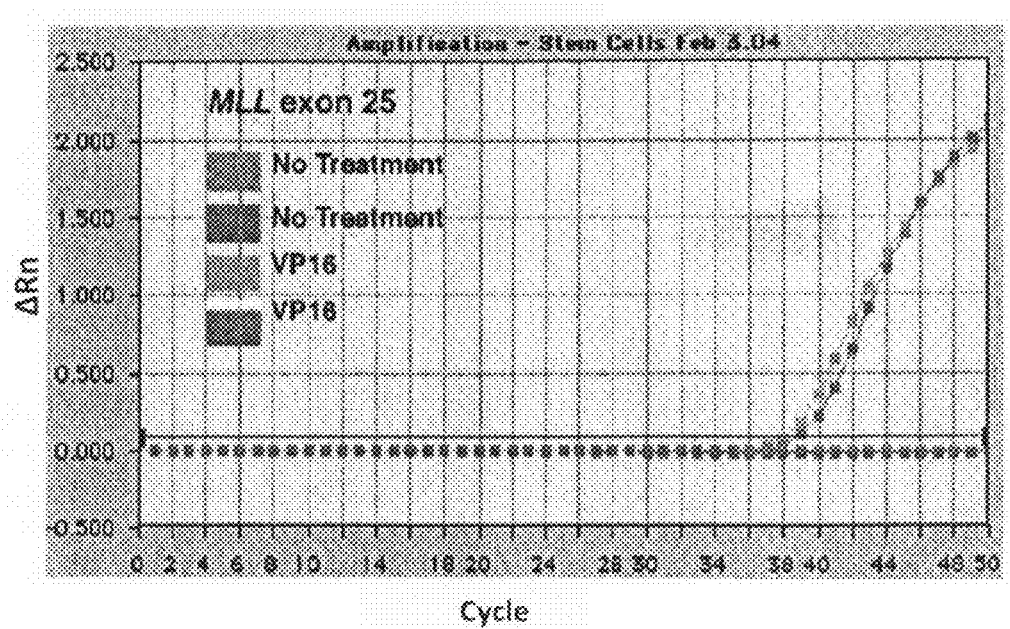

Real-time PCR products were detected with the primer pair for the junction of MLL intron 8-exon 9 in the DOP-amplified immunoaffinity-purified DNA topoisomerase IIα-bound DNA from untreated and etoposide-treated CD34+ cells (FIG. 9A). The DOP template DNA used for real-time PCR was 500 bp to 1 kb. Since DNA templates containing double-strand breaks from DNA topoisomerase II cleavage would not be amplified by PCR, these data indicate the presence of DNA-DNA topoisomerase II covalent complexes proximal to the amplicon (MLL bcr positions 6784 to 6851) where products were detected with resolution at the size of the DOP template. No products were detected in reactions assaying the GAPDH gene (FIG. 9B), which is not involved in MLL translocations. Although no product was detected in untreated CD34+ cells, etoposide induced DNA-DNA topoisomerase II covalent complexes proximal to the MLL exon 25 amplicon (FIG. 9C), indicating that the formation of DNA topoisomerase II cleavage complexes in MLL is not limited to the bcr.

Figure 9D:
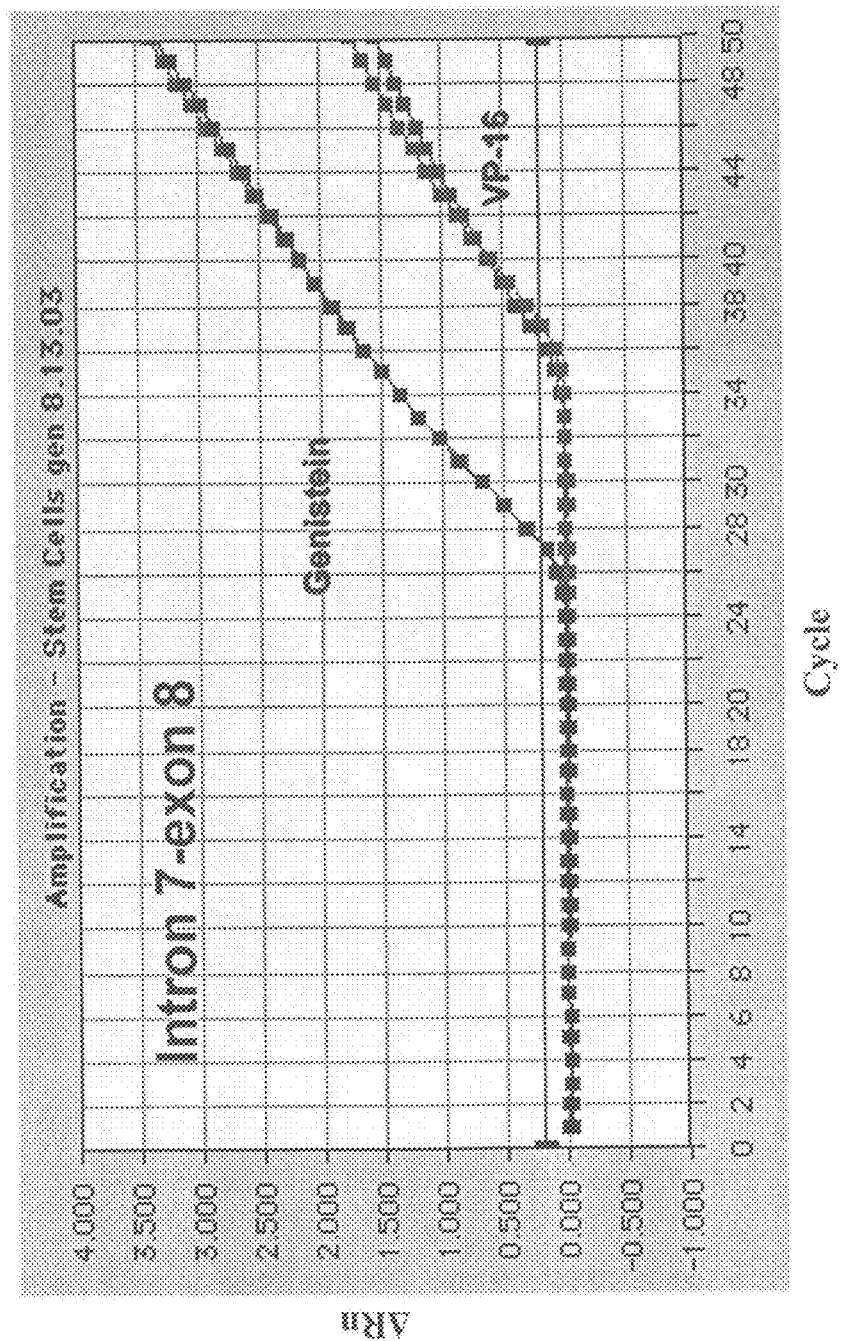

DNA Topoisomerase II Covalent Complexes with MLL bcr are Detected in Etoposide-Treated and Genistein-Treated Ex Vivo-Expanded CD34+ Cells In cases of leukemia in infants, the MLL translocation breakpoints are distributed heterogeneously in the bcr (Felix, 1998.) Genistein is one example of a naturally-occurring DNA topoisomerase II poison that can stimulate formation of cleavage complexes with DNA and to which the fetus can be exposed in utero via the maternal diet. FIG. 9D shows real-time PCR products that were detected with primers at the junction of MLL intron 7-exon 8 in the DOP-amplified immunoaffinity-purified DNA topoisomerase IIα-bound DNA after treatment of CD34+ cells with either etoposide or genistein.

Discussion

The temporal emergence of MLL translocations has been characterized herein with respect to the timing of administration of specific anti-cancer drugs and mechanistic studies of DNA topoisomerase II cleavage were performed in order to link specific DNA damage to the genesis of MLL translocations in two cases of treatment-related leukemia. There was variability in molecular emergence of the translocations; after all 4 cycles of CAV and 3 cycles of PVP in one case, but after only 2 cycles of CAV in the other (Megonigal et al., 2000). In both cases the translocation was absent at neuroblastoma diagnosis, suggesting that the treatment caused and did not select for a pre-existing translocation. These results are consistent with other observations on a patient diagnosed with primary ALL and MLL-rearranged treatment-related AML where the MLL translocation was found to emerge during the course of treatment (Blanco et al., 2001). Absence of the MLL translocation at neuroblastoma diagnosis and the short latency in the secondary cases under study here also relate to the time of acquisition of the translocation in MLL-rearranged de novo cases. In MLL-rearranged infant leukemias the translocation is a somatic, in utero event and the latency is short: specifically from some time in pregnancy to the time of leukemia diagnosis in the infant host (Ford et al., 1993; Gale et al., 1997; Megonigal et al., 1998). However, MLL-rearranged leukemias in older children generally are not traceable to birth (Maia et al., 2004). Factors that determine latency from acquisition of the translocation to emergence of leukemia are unknown but the variable latencies in the present study, 5 months and 15.5 months in the respective cases where the partner genes were AF-4 and GAS7, may indicate differences in sufficiency of the varied MLL gene fusions. Latency also may be a function of the subsequent primary cancer treatment, which would not only contribute to secondary alterations but also affect selection and survival of the preleukemia clone.

Patient t-120 was managed with autologous marrow rescue after monoclonal antibody 3F8-targeted $^{131}$I-radioimmunotherapy. The ALL was diagnosed 11 months after neuroblastoma diagnosis, only 2 weeks after transplant. It has been suggested that autologous stem-cell collection following etoposide is associated with an increased risk of leukemia with characteristic balanced translocations (Krishnan et al., 2000). However, by a sensitive PCR-based assay the t(4; 11) was not detectable in the unpurged or the purged marrow autograft harvested after the second cycle of etoposide-containing PVP, and did not emerge until after all chemotherapy cycles were complete. The t(4; 11) occurred before the local radiation and radioimmunotherapy during the intensive N7 neuroblastoma regimen. The MLL-GAS7 translocation also was present before any radiation (Megonigal et al., 2000), indicating that the chemotherapy but not radiation contributed to the damage that caused these translocations.

The DNA topoisomerase II inhibitor exposures before molecular emergence of the t(4; 11) in the case of patient t-120 were doxorubicin and etoposide, and there were etoposide-, etoposide metabolite- and doxorubicin-stimulated DNA topoisomerase II in vitro cleavage sites proximal to the translocation breakpoints that could be repaired to form both breakpoint junctions. The alternative models for formation of the der(11) and der(4) genomic breakpoint junctions were based on cleavage sites at MLL bcr position 6588, which was enhanced by all of the drug exposures, and either the cleavage site at AF-4 intron 3 position 7126 enhanced only by etoposide and its metabolites (FIG. 3A) or AF-4 intron 3 position 7114 enhanced only by doxorubicin (FIG. 3B). Since this was a later-occurring translocation during the treatment and emerged only after exposure to both DNA topoisomerase II poisons in the regimen, it is possible that etoposide or its metabolites or doxorubicin caused the relevant damage. Nonetheless, in the ALL of patient t-120, the processing of functional drug-stabilized DNA topoisomerase II cleavage sites in MLL and AF-4 generated the observed genomic breakpoint junctions.

These results differ from the findings in the second case where the translocation first became detectable when doxorubicin was the only DNA topoisomerase II poison to which the patient was exposed. The translocation breakpoints in MLL and GAS7 were proximal to strong doxorubicin-stimulated DNA topoisomerase II in vitro cleavage sites at MLL bcr position 4675 and GAS7 position 1238 that could be resolved to form both breakpoint junctions. This is the first functional demonstration of relevance of doxorubicin-stimulated DNA topoisomerase II covalent complexes with MLL and with its partner gene in the genesis of MLL translocations in treatment-related AML.

Another consideration was that anthracyclines are known to exhibit both cleavage stimulation characteristic of DNA topoisomerase II poisons at low concentrations but, at high concentrations, catalytic inhibition of DNA topoisomerase II function due to intercalation (Capranico and Binaschi, 1998). Analysis of DNA topoisomerase II cleavage with doxorubicin over a range of concentrations unmasked doxorubicin-stimulated cleavage sites proximal to the translocation breakpoints in MLL, AF-4 and GAS7 that were not detected at higher concentrations. The balance of dose-dependent dual effects of doxorubicin as a poison and a catalytic inhibitor of DNA topoisomerase II function has substantial implications for its role in the genesis of translocations in a cellular context because the model for formation of the translocations is based on poisoning effects. The site selectivity of the doxorubicin-stimulated in vitro cleavage sites proximal to the breakpoints also is of interest. Different patterns of cleavage stimulation by various DNA topoisomerase II poisons at preferred sites in any given substrate has suggested that local base sequences enable formation of ternary drug-DNA-enzyme complexes (Capranico and Binaschi, 1998). The previously reported site selectivity of doxorubicin was A at position −1 and T at position −2 relative to the cleavage (Capranico and Binaschi, 1998). Here, however, only 2 of the 7 cleavage sites in MLL, AF-4 and GAS7 (shown in FIGS. 2C, 2D, 4C, and 4D) where doxorubicin behaved as a poison (specifically, MLL bcr position 4673 and AF-4 intron 3 position 7119), fulfilled these sequence preferences on either the sense strand or the antisense strand of the DNA. Thus the sequence preferences for poisoning effects of doxorubicin may be less stringent than previously thought.

Non-homologous end joining (NHEJ) repair events, which have been implicated in the resolution of DNA damage in the MLL translocation process (Lovett et al., 2001), are often imprecise and ensue after small deletions or insertions at the site of damage (Liang et al., 1998). The models in FIGS. 3A, 3B, and 5 invoked small deletions at the DNA topoisomerase II cleavage sites in MLL and its partner genes to create homologous overhangs that formed characteristic breakpoint junctions. Single-base homologies, as would be present after exonucleolytic nibbling at these staggered nicks, are sufficient for error-prone NHEJ (Liang et al., 1998).

The formation of drug-stabilized and native DNA topoisomerase II cleavage complexes in ex vivo-expanded human CD34+ cells was also investigated as a cellular model for analysis of MLL translocations. It was important to devise a cellular model to further study the role of DNA topoisomerase II cleavage in the genesis of MLL translocations because cleavage sites in the cellular context should be more restricted than in vitro (Capranico et al., 1990). In a murine retroviral transplant model it recently was shown that leukemias with MLL translocations can arise either in self-renewing stem cells or in committed myeloid progenitor cell populations (Cozzio et al., 2003), corroborating relevance of the human CD34+ cell model system. The analyses of DNA topoisomerase IIα mRNA (Table 1) and protein (FIG. 6) expression indicate that in human CD34+ cells grown in short-term culture DNA topoisomerase IIα is highly expressed at levels comparable to human hematopoietic cell lines. Human CD34+ cells had not been previously studied in the ICE bioassay, which detects any DNA in total genomic DNA bound to DNA topoisomerase IIα by the covalent phosphotyrosine linkage formed between this enzyme and DNA (Whitmarsh et al., 2003). Both native and etoposide-stabilized DNA topoisomerase IIα cleavage complexes were demonstrable in the CD34+ cells.

In addition, a new approach was devised for detecting DNA topoisomerase IIα covalently bound specifically to the MLL bcr in untreated or etoposide-treated CD34+ cells. This assay, which is similar to a ChIP assay (Boyd et al., 1998) without cross-linking, was accomplished by immuno-affinity purification of DNA topoisomerase II covalent complexes from the total genomic DNA of the CD34+ cells followed by DOP and then real-time PCR using primers proximal to the hotspot for MLL translocation breakpoints (Whitmarsh et al., 2003) in intron 8 3' in the bcr. Native as well as etoposide-stabilized DNA topoisomerase II covalent complexes with the MLL bcr were detectable in the immuno-affinity purified DNA topoisomerase II covalent complexes, demonstrating that DNA topoisomerase II forms covalent complexes with MLL at sites of translocation breakpoints in human CD34+ cells. That MLL exon 25 is distal to the bcr and not involved in leukemia-associated translocations, yet etoposide induced DNA topoisomerase II cleavage complexes proximal to the MLL exon 25 amplicon, may suggest that translocations resulting from repair of DNA topoisomerase II-mediated damage in MLL exon 25 would not provide a selective or proliferative advantage for leukemogenesis. Detection of DNA topoisomerase II covalent complexes at the hotspot for MLL translocation breakpoints in intron 8 3' in the bcr in the presence of etoposide establishes that drug-stabilized DNA topoisomerase II cleavage is a mechanism to damage MLL at a relevant site and in a relevant cellular model system.

In addition, formation of DNA topoisomerase IIα covalent complexes at the hotspot for MLL translocation breakpoints by the native enzyme is especially important. Translocations of the MLL gene are the hallmark aberrations in leukemias that follow chemotherapy with DNA topoisomerase II poisons (Rowley and Olney, 2002) and several treatment-related leukemias occurring after DNA topoisomerase II poisons have translocation breakpoints at this hotspot region (reviewed in (Whitmarsh et al., 2003)). However, not all MLL-rearranged treatment-related leukemias occur after exposure to these agents. For example, a case of secondary AML with t(9; 11) and der(11) and der(9) MLL breakpoints in this hotspot region has been reported after chemotherapy for primary Hodgkin's disease without DNA topoisomerase II poisons (Langer et al., 2003). Formation of DNA topoisomerase IIα covalent complexes in this genomic region by the native enzyme may be the cause of the breakage in such cases. Furthermore, native DNA topoisomerase II cleavage also should be active during the bone marrow repopulation and recovery after cytotoxic chemotherapy in general because DNA topoisomerase IIα expression is cell cycle-dependent and highest in proliferating cells (Isaacs et al., 1998).

The results of the present study imply two mechanisms for DNA topoisomerase II involvement in the DNA damage that results in MLL translocations. The first mechanism implicates direct poisoning effects of drug-stabilized DNA topoisomerase II cleavage complexes at the translocation breakpoint sites as the damage mechanism. In the second mechanism, native DNA topoisomerase II mediates cleavage at the translocation breakpoints. This second mechanism is relevant to the cases where prior cytotoxic chemotherapy without DNA topoisomerase II poisons was administered. Ternary DNA topoisomerase II cleavage complexes with MLL sequences involved in translocations can be stimulated by poisons of the enzyme, but the native enzyme alone forms cleavage complexes with the MLL translocation breakpoint hotspot; either can be important in the DNA damage that leads to translocations.

Another example was shown of real-time PCR detection of DNA topoisomerase II complexes in proximity to the MLL intron 7-exon 8 junction in CD34+ cells that were treated either with etoposide or genistein, indicating that the naturally-occurring compound that is found in diet also is associated with formation of functional DNA topoisomerase cleavage complexes proximal to this amplicon in the MLL bcr.

EXAMPLE V

Microarrays

One goal of these assays is the global identification of DNA topoisomerase II mediated damage from etoposide and its metabolites in the MLL bcr and in the genome in general. Such damage can be studied in ex vivo-expanded human bone marrow progenitor cells as representative targets for translocations. A direct interaction of DNA topoisomerase II with specific MLL bcr sequences has not been investigated in a cellular context except in the real-time PCR assays described herein. The generation of a custom MLL bcr-specific oligonucleotide array would further streamline and improve upon the present detection method.

Employing XEOCHIP™ technology (Xeotron, Houston, Tex.), a first generation MLL bcr oligonucleotide array containing replicate slots of each of 162 probes was created. The 162 probes included 73 probes for the non-repetitive MLL bcr sequences, 8 probes for the Alu region between nucleotide positions 663-1779 in the MLL bcr, 57 probes for MLL exon 25 which is unaffected by the translocations, and 24 probes for 9 bacterial control genes (see Tables 2 and 3; Tables 4 and 5 provide another example of a series of oligonucleotides that can be employed in a microarray). The 8.3 kb MLL bcr is represented by replicates of each of the 73 50 mers at average intervals of 115 bases to span the bcr. Because it has been well documented in the literature that the printing, general hybridization conditions, and scanning of microarrays introduce systemic effects that are related to the position on the chip, replicates of each of the probes in the array have been spaced throughout the chip.

MLL-specific probes without homology to each other or to Alu sequences were designed to be 50 mer sense-strand sequences in accordance with Xeotron parameters. A BLAST search of the probes against the human genome sequence confirmed that the probes were MLL-specific. Special probe design was utilized for the Alu-rich region from MLL bcr positions 663-1779 where no consideration for cross-homology was possible. Bacterial control gene sequences were BLAST searched against the human genome sequence database. Probes were not designed to regions where BLAST hits were found and then designed to be sense-strand 50 mer sequences using the Xeotron parameters. Except in the instance of the Alu-rich region probes, this probe design, under stringent hybridization and washing conditions, should enable distinguishing between distinct sequences where the overall homology is <80% (i.e. 10 mismatches out of 50 bases) and where there are no stretches of >25 bases of homology.

Figure 10:
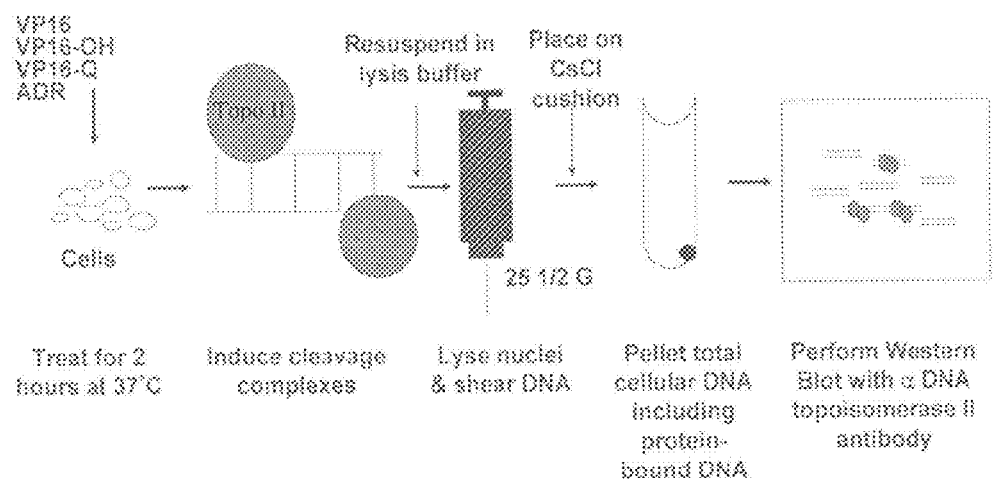
FIG. 10 is a schematic drawing of the methods of an in vivo complex of enzyme bioassay allowing for the detection of DNA-DNA topoisomerase II complexes.
Figure 11:
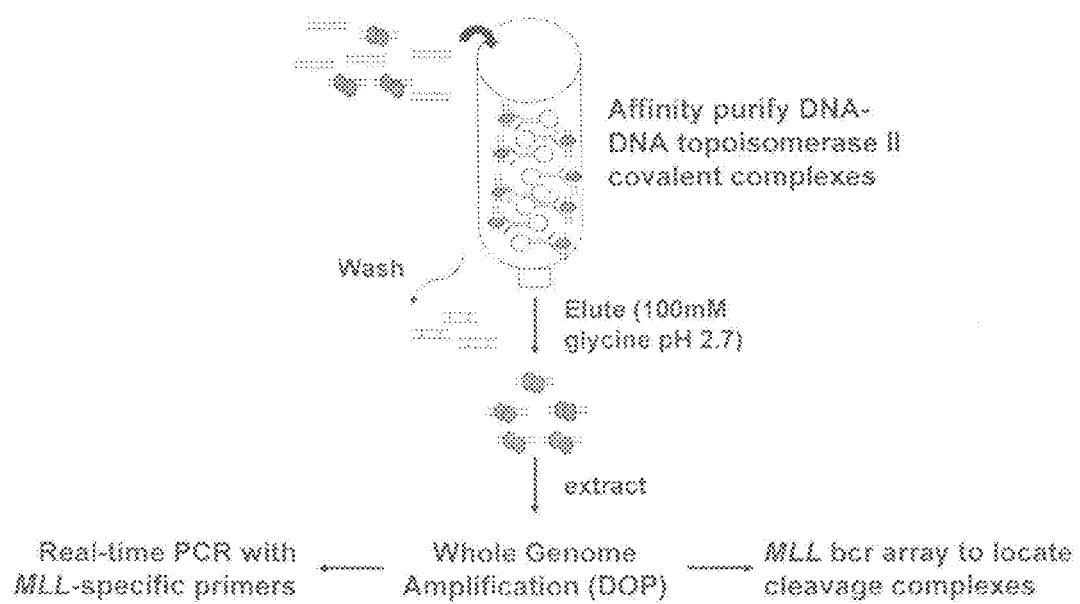
FIG. 11 is a schematic drawing of the methods for the isolation of DNA-DNA topoisomerase II complexes.

Primary CD34+ selected human bone marrow cells were obtained through the NHLBI or purchased commercially. The cells were expanded ex vivo using conditions optimized to promote minimal differentiation in order to increase cell numbers as required to generate a useful model system. Briefly, the general strategy is: 1) ex vivo-expand CD34+ cells or other relevant cells to be treated with etoposide or different test compound, 2) treat the cells with etoposide or reserve as untreated, 3) lyse the cells, 4) shear the DNA, 5) isolate total genomic DNA including any protein-bound DNA as for ICE bioassays (see FIG. 10), 6) isolate DNA-DNA topoisomerase II covalent complexes with an immunoaffinity column according to the scheme summarized in FIG. 11 and elute DNA-DNA topoisomerase II covalent complexes from the column, 7) perform whole genome amplification by degenerative oligonucleotide PCR or another suitable technique, 8) quantify DOP products by measuring the OD260, 9) measure fragment sizes of DOP products in an agarose gel, and 10) analyze the DOP products from the experimental sample (which can either be untreated cells or cells treated with specific agent) and the calibrated standard sample (i.e. plasmid containing genomic sequence of the MLL bcr) labeled with a detectable label such as ALEXA FLUOR® dyes (Molecular Probes, Eugene, Oreg.), heat-denatured, and hybridized in different channels to a pre-hybridized MLL bcr XEOCHIP™.

Components of the experimental design, including statistical and computational tools to use MLL bcr DNA oligonucleotide arrays to study human CD34+ cells treated with etoposide and compare treated with untreated cells, also were developed. A degenerative oligonucleotide PCR- (DOP-) amplified plasmid DNA template containing an 8.3 kb genomic DNA insert of the entire MLL bcr in PBSK II+ is employed for use as a labeled reference sample calibrated against every probe in the array in order to enable better accuracy in spot intensity information and control for any unequal labeling of specific regions in the bcr in the DOP-amplified experimental samples. By 1) serial dilutions of ALEXA FLUOR® dye-labeled DOP products of the reference sample, 2) acquisition of MLL bcr XEOCHIP™ images with the Cy-3 and Cy-5 channels of a GENEPIX® (Axon Instruments, Foster City, Calif.) laser scanner, and 3) analysis using the GENEPIX® program, it has been established that hybridization of 0.02 µg of the reference sample gives a non-saturating hybridization signal (FIG. 12).

In additional experiments, CD34+ cells were expanded in culture, treated or untreated for 2 hours with etoposide at 100 µM final concentration. The total cellular DNA was harvested including any protein-bound DNA on CsCl cushions, and then immunoaffinity column purification of DNA covalently bound to DNA topoisomerase IIα was performed in etoposide-treated or untreated samples according to the schematics summarized in FIG. 10 and FIG. 11. DOP of the immunoaffinity-purified DNA topoisomerase II cleavage complexes from the treated and untreated cells was performed exactly as was done with the reference sample. In one such experiment the samples from untreated cells or cells treated with 100 µM etoposide were labeled with ALEXA FLUOR® 546 (equivalent of Cy-3; green) and the MLL bcr reference sample was labeled with ALEXA FLUOR® 647 (equivalent of Cy-5; red). Dye-swap experiments were also performed. MLL bcr XEOCHIP™ hybridizations were then performed with 0.02 µg of ALEXA FLUOR® dye-labeled DOP products of etoposide-treated or untreated samples in one channel of the chip and the reference sample labeled with the reverse ALEXA FLUOR® dye in the other channel.

GeneSpring (Silicon Genetics, Redwood City, Calif.) was employed as a computational tool to visualize and analyze the data from MLL bcr XEOCHIPS™ with either treated or untreated samples in one channel and the reference sample in the other. Non-parametric statistical regression tools can also be applied in order to identify hybridization hotspots that suggest effects of treatment. The preliminary data analysis suggests that the MLL XEOCHIPS™ microarray is useful for detecting hotspots and coldspots for DNA topoisomerase II complex formation with the MLL bcr.

Figure 12A:
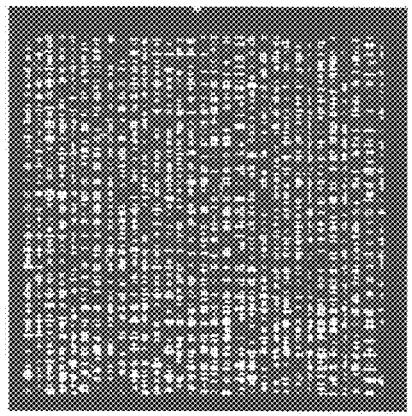
FIG. 12A is an image of XEOCHIPS™ containing different amounts of products from DOP amplification of MLL bcr plasmid that were labeled with ALEXA FLUOR® 546 or ALEXA FLUOR® 647 in order to establish conditions for calibrated standard.
Figure 12A:
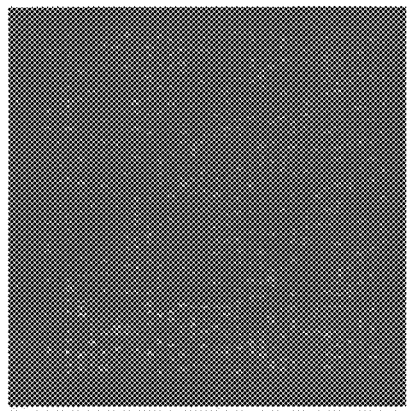
Figure 12B:
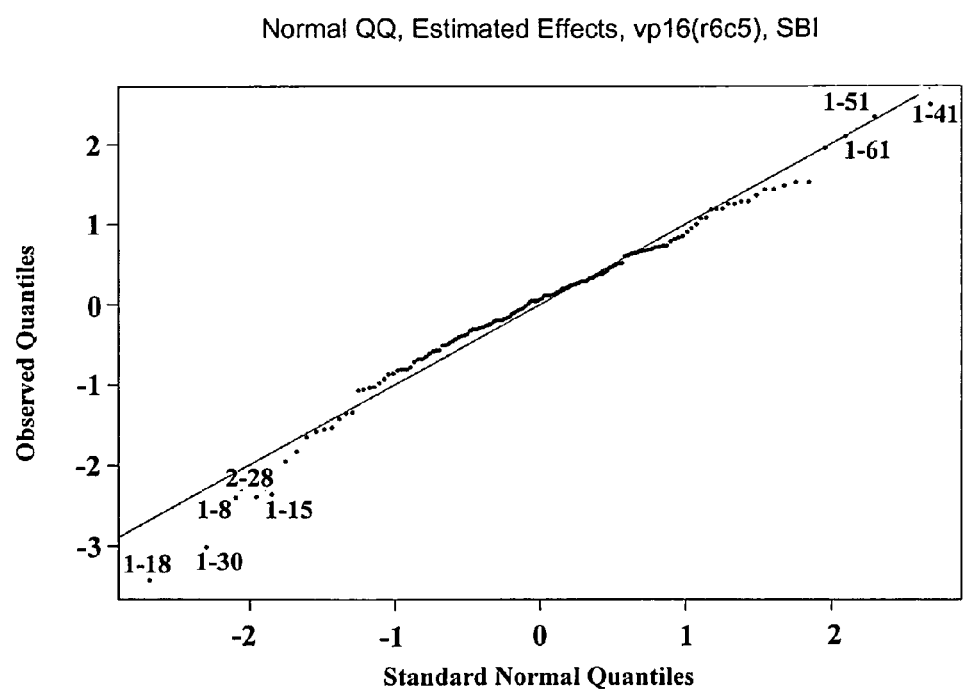
FIGS. 12B and 12C are Quantile-Quantile plots standardized by intensity comparing etoposide-treated and untreated cells and genistein-treated and untreated cells, respectively, when the test sample (treated or untreated) was labeled with ALEXA FLUOR® 546 and the MLL bcr calibrated reference sample was labeled with ALEXA FLUOR® 647. The points that deviate from the linear relationship suggests coldspots or hotspots for formation DNA topoisomerase II cleavage complexes in the treated compared to untreated cells.

A Quantile-Quantile (Q-Q) plot (44, 45) standardized by intensity was employed to compare etoposide-treated and untreated cells (FIG. 12B). DOP-amplified DNA from the DNA topoisomerase II cleavage complexes in treated or untreated cells on separate chips was labeled with ALEXA FLUOR® 546. The MLL bcr reference sample was labeled with ALEXA FLUOR® 647. The null hypothesis represented by the straight line is that there is no effect at any probe, whereas upward departure points are potential hotspots and downward departure points are potential coldspots. As seen in FIG. 12B, probes 1-41 and 1-51, for example, appear as hotspots and probes 2-28, 1-30, 1-18, and 1-15, for example, appears as a cold spot.

Figure 12C:
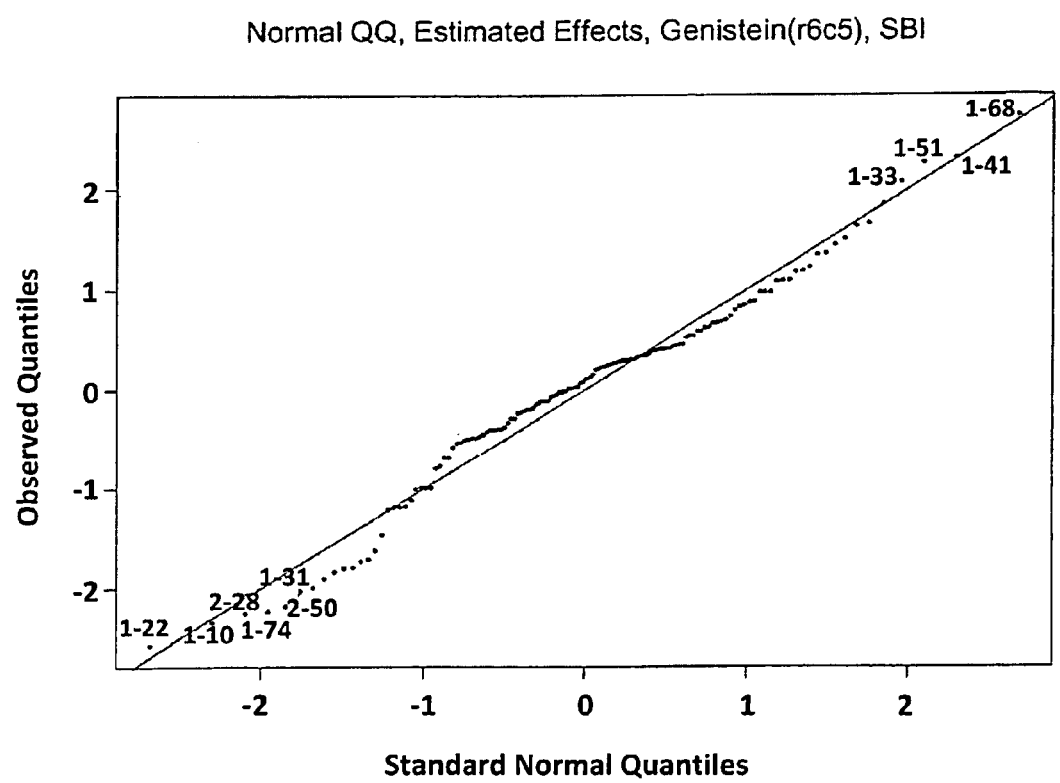

A similar Q-Q plot was performed on untreated cells and cells treated with 100 μM genistein (FIG. 12C). Probes 1-68 (SEQ ID NO: 157), 1-41 (SEQ ID NO: 49), 1-51 (SEQ ID NO: 141), and 1-33 (SEQ ID NO: 132) were identified as potential hotspots and probes 1-31 (SEQ ID NO: 27), 2-50 (SEQ ID NO: 162), 1-74 (SEQ ID NO: 62), 2-28 (SEQ ID NO: 34), 1-10 (SEQ ID NO: 83), and 1-22 (SEQ ID NO: 71) were identified as potential coldspots. Notably, probes 1-41 (SEQ ID NO: 49) and 1-51 (SEQ ID NO: 141) were identified as hotspots in both etopside and genistein treated cells while probe 2-28 (SEQ ID NO: 34) was identified as a coldspot. It is also noteworthy that probes 1-68 (SEQ ID NO: 157) and 1-33 (SEQ ID NO: 132) correspond to nearby oligonucleotides. Additionally, these results mirror in vitro cleavage studies with etoposide and genistein as there is some overlap in cleavage sites induced by the different agents as well as differences in site selectivity.

TABLE 2

| Random Sorter | Original Sorter | Probe ID | Ranked order of preference | Sequence Description | Sequence Length | Probe Position within sequence |
|---|---|---|---|---|---|---|
| 1 | 93 | 0002-12 | 12 | MLL Exon 25 | 4249 | 2662 |
| 2 | 66 | 0001-66 | 24 | MLL Exon-intron 5 to 11 | 8342 | 3682 |
| 3 | 113 | 0002-32 | 32 | MLL Exon 25 | 4249 | 2450 |
| 4 | 24 | 0001-24 | 24 | MLL Exon-intron 5 to 11 | 8342 | 5309 |
| 5 | 32 | 0001-32 | 32 | MLL Exon-intron 5 to 11 | 8342 | 5938 |
| 6 | 106 | 0002-25 | 25 | MLL Exon 25 | 4249 | 436 |
| 7 | 54 | 0001-54 | 12 | MLL Exon-intron 5 to 11 | 8342 | 4395 |
| 8 | 161 | LysX-M | 1 | LysX-M | 270 | 132 |
| 9 | 118 | 0002-37 | 37 | MLL Exon 25 | 4249 | 2748 |
| 10 | 112 | 0002-31 | 31 | MLL Exon 25 | 4249 | 334 |
| 11 | 110 | 0002-29 | 29 | MLL Exon 25 | 4249 | 2829 |
| 12 | 157 | TrpnX-3 | 1 | TrpnX-3 | 579 | 128 |
| 13 | 86 | 0002-5 | 5 | MLL Exon 25 | 4249 | 3476 |
| 14 | 160 | BioB-3 | 1 | BioB-3 | 298 | 61 |
| 15 | 30 | 0001-30 | 30 | MLL Exon-intron 5 to 11 | 8342 | 2460 |
| 16 | 61 | 0001-61 | 19 | MLL Exon-intron 5 to 11 | 8342 | 3149 |
| 17 | 39 | 0001-39 | 39 | MLL Exon-intron 5 to 11 | 8342 | 3214 |
| 18 | 81 | 0001-81 | 8 | >MLL Exon-intron 5 to 11 | 8342 | 1578 |
| 19 | 12 | 0001-12 | 12 | MLL Exon-intron 5 to 11 | 8342 | 4666 |
| 20 | 2 | 0001-2 | 2 | MLL Exon-intron 5 to 11 | 8342 | 7974 |
| 21 | 73 | 0001-73 | 31 | MLL Exon-intron 5 to 11 | 8342 | 1875 |
| 22 | 130 | 0002-49 | 12 | MLL Exon 25 | 4249 | 160 |
| 23 | 85 | 0002-4 | 4 | MLL Exon 25 | 4249 | 4048 |
| 24 | 103 | 0002-22 | 22 | MLL Exon 25 | 4249 | 1285 |
| 25 | 46 | 0001-46 | 4 | MLL Exon-intron 5 to 11 | 8342 | 314 |
| 26 | 57 | 0001-57 | 15 | MLL Exon-intron 5 to 11 | 8342 | 3349 |
| 27 | 31 | 0001-31 | 31 | MLL Exon-intron 5 to 11 | 8342 | 88 |
| 28 | 139 | BioB-5 | 1 | BioB-5 | 274 | 83 |
| 29 | 52 | 0001-52 | 10 | MLL Exon-intron 5 to 11 | 8342 | 5089 |
| 30 | 72 | 0001-72 | 30 | MLL Exon-intron 5 to 11 | 8342 | 4585 |
| 31 | 20 | 0001-20 | 20 | MLL Exon-intron 5 to 11 | 8342 | 7877 |
| 32 | 13 | 0001-13 | 13 | MLL Exon-intron 5 to 11 | 8342 | 5549 |
| 33 | 155 | ThrX-5 | 1 | ThrX-5 | 645 | 391 |
| 34 | 109 | 0002-28 | 28 | MLL Exon 25 | 4249 | 2314 |
| 35 | 21 | 0001-21 | 21 | MLL Exon-intron 5 to 11 | 8342 | 7776 |
| 36 | 45 | 0001-45 | 3 | MLL Exon-intron 5 to 11 | 8342 | 4501 |
| 37 | 65 | 0001-65 | 23 | MLL Exon-intron 5 to 11 | 8342 | 5347 |
| 38 | 34 | 0001-34 | 34 | MLL Exon-intron 5 to 11 | 8342 | 4361 |
| 39 | 15 | 0001-15 | 15 | MLL Exon-intron 5 to 11 | 8342 | 1779 |
| 40 | 119 | 0002-38 | 1 | MLL Exon 25 | 4249 | 3435 |
| 41 | 35 | 0001-35 | 35 | MLL Exon-intron 5 to 11 | 8342 | 6403 |
| 42 | 18 | 0001-18 | 18 | MLL Exon-intron 5 to 11 | 8342 | 6578 |
| 43 | 99 | 0002-18 | 18 | MLL Exon 25 | 4249 | 3937 |
| 44 | 126 | 0002-45 | 8 | MLL Exon 25 | 4249 | 857 |
| 45 | 94 | 0002-13 | 13 | MLL Exon 25 | 4249 | 181 |
| 46 | 7 | 0001-7 | 7 | MLL Exon-intron 5 to 11 | 8342 | 7 |
| 47 | 105 | 0002-24 | 24 | MLL Exon 25 | 4249 | 3395 |
| 48 | 100 | 0002-19 | 19 | MLL Exon 25 | 4249 | 1182 |
| 49 | 41 | 0001-41 | 41 | MLL Exon-intron 5 to 11 | 8342 | 343 |
| 50 | 116 | 0002-35 | 35 | MLL Exon 25 | 4249 | 1984 |
| 51 | 117 | 0002-36 | 36 | MLL Exon 25 | 4249 | 523 |
| 52 | 149 | DapX-M | 1 | DapX-M | 561 | 367 |
| 53 | 150 | LysX-3 | 1 | LysX-3 | 283 | 171 |
| 54 | 5 | 0001-5 | 5 | MLL Exon-intron 5 to 11 | 8342 | 2361 |
| 55 | 162 | LysX-5 | 1 | LysX-5 | 273 | 12 |
| 56 | 67 | 0001-67 | 25 | MLL Exon-intron 5 to 11 | 8342 | 3471 |
| 57 | 53 | 0001-53 | 11 | MLL Exon-intron 5 to 11 | 8342 | 7636 |
| 58 | 88 | 0002-7 | 7 | MLL Exon 25 | 4249 | 3557 |
| 59 | 27 | 0001-27 | 27 | MLL Exon-intron 5 to 11 | 8342 | 3584 |
| 60 | 153 | PheX-M | 1 | PheX-M | 392 | 238 |
| 61 | 152 | PheX-5 | 1 | PheX-5 | 348 | 86 |
| 62 | 74 | 0001-74 | 1 | >MLL Exon-intron 5 to 11 | 8342 | 779 |
| 63 | 83 | 0002-2 | 2 | MLL Exon 25 | 4249 | 3839 |

TABLE 2-continued

| Random Sorter | Original Sorter | Probe ID | Ranked order of preference | Sequence Description | Sequence Length | Probe Position within sequence |
|---|---|---|---|---|---|---|
| 64 | 75 | 0001-75 | 2 | >MLL Exon-intron 5 to 11 | 8342 | 870 |
| 65 | 158 | TrpnX-5 | 1 | TrpnX-5 | 531 | 218 |
| 66 | 101 | 0002-20 | 20 | MLL Exon 25 | 4249 | 2956 |
| 67 | 44 | 0001-44 | 2 | MLL Exon-intron 5 to 11 | 8342 | 516 |
| 68 | 76 | 0001-76 | 3 | >MLL Exon-intron 5 to 11 | 8342 | 991 |
| 69 | 114 | 0002-33 | 33 | MLL Exon 25 | 4249 | 3303 |
| 70 | 19 | 0001-19 | 19 | MLL Exon-intron 5 to 11 | 8342 | 7541 |
| 71 | 22 | 0001-22 | 22 | MLL Exon-intron 5 to 11 | 8342 | 3022 |
| 72 | 135 | 0002-54 | 17 | MLL Exon 25 | 4249 | 2457 |
| 73 | 90 | 0002-9 | 9 | MLL Exon 25 | 4249 | 70 |
| 74 | 47 | 0001-47 | 5 | MLL Exon-intron 5 to 11 | 8342 | 6398 |
| 75 | 144 | BioDn-5 | 1 | BioDn-5 | 277 | 221 |
| 76 | 123 | 0002-42 | 5 | MLL Exon 25 | 4249 | 1264 |
| 77 | 79 | 0001-79 | 6 | >MLL Exon-intron 5 to 11 | 8342 | 1343 |
| 78 | 122 | 0002-41 | 4 | MLL Exon 25 | 4249 | 1556 |
| 79 | 111 | 0002-30 | 30 | MLL Exon 25 | 4249 | 909 |
| 80 | 120 | 0002-39 | 2 | MLL Exon 25 | 4249 | 2280 |
| 81 | 50 | 0001-50 | 8 | MLL Exon-intron 5 to 11 | 8342 | 680 |
| 82 | 56 | 0001-56 | 14 | MLL Exon-intron 5 to 11 | 8342 | 5466 |
| 83 | 10 | 0001-10 | 10 | MLL Exon-intron 5 to 11 | 8342 | 2611 |
| 84 | 91 | 0002-10 | 10 | MLL Exon 25 | 4249 | 604 |
| 85 | 124 | 0002-43 | 6 | MLL Exon 25 | 4249 | 2016 |
| 86 | 37 | 0001-37 | 37 | MLL Exon-intron 5 to 11 | 8342 | 6683 |
| 87 | 8 | 0001-8 | 8 | MLL Exon-intron 5 to 11 | 8342 | 169 |
| 88 | 107 | 0002-26 | 26 | MLL Exon 25 | 4249 | 1656 |
| 89 | 25 | 0001-25 | 25 | MLL Exon-intron 5 to 11 | 8342 | 663 |
| 90 | 140 | BioB-M | 1 | BioB-M | 258 | 80 |
| 91 | 38 | 0001-38 | 38 | MLL Exon-intron 5 to 11 | 8342 | 4480 |
| 92 | 26 | 0001-26 | 26 | MLL Exon-intron 5 to 11 | 8342 | 3921 |
| 93 | 98 | 0002-17 | 17 | MLL Exon 25 | 4249 | 2540 |
| 94 | 142 | BioC-5 | 1 | BioC-5 | 349 | 193 |
| 95 | 97 | 0002-16 | 16 | MLL Exon 25 | 4249 | 1575 |
| 96 | 102 | 0002-21 | 21 | MLL Exon 25 | 4249 | 3753 |
| 97 | 14 | 0001-14 | 14 | MLL Exon-intron 5 to 11 | 8342 | 2699 |
| 98 | 16 | 0001-16 | 16 | MLL Exon-intron 5 to 11 | 8342 | 6769 |
| 99 | 151 | PheX-3 | 1 | PheX-3 | 442 | 353 |
| 100 | 42 | 0001-42 | 42 | MLL Exon-intron 5 to 11 | 8342 | 4574 |
| 101 | 55 | 0001-55 | 13 | MLL Exon-intron 5 to 11 | 8342 | 2829 |
| 102 | 64 | 0001-64 | 22 | MLL Exon-intron 5 to 11 | 8342 | 2515 |
| 103 | 127 | 0002-46 | 9 | MLL Exon 25 | 4249 | 2636 |
| 104 | 134 | 0002-53 | 16 | MLL Exon 25 | 4249 | 1392 |
| 105 | 84 | 0002-3 | 3 | MLL Exon 25 | 4249 | 3101 |
| 106 | 108 | 0002-27 | 27 | MLL Exon 25 | 4249 | 705 |
| 107 | 78 | 0001-78 | 5 | >MLL Exon-intron 5 to 11 | 8342 | 1256 |
| 108 | 63 | 0001-63 | 21 | MLL Exon-intron 5 to 11 | 8342 | 2940 |
| 109 | 138 | 0002-57 | 20 | MLL Exon 25 | 4249 | 3351 |
| 110 | 141 | BioC-3 | 1 | BioC-3 | 253 | 5 |
| 111 | 4 | 0001-4 | 4 | MLL Exon-intron 5 to 11 | 8342 | 6963 |
| 112 | 49 | 0001-49 | 7 | MLL Exon-intron 5 to 11 | 8342 | 5675 |
| 113 | 77 | 0001-77 | 4 | >MLL Exon-intron 5 to 11 | 8342 | 1153 |
| 114 | 28 | 0001-28 | 28 | MLL Exon-intron 5 to 11 | 8342 | 5669 |
| 115 | 136 | 0002-55 | 18 | MLL Exon 25 | 4249 | 278 |
| 116 | 92 | 0002-11 | 11 | MLL Exon 25 | 4249 | 1437 |
| 117 | 89 | 0002-8 | 8 | MLL Exon 25 | 4249 | 4165 |
| 118 | 128 | 0002-47 | 10 | MLL Exon 25 | 4249 | 3269 |
| 119 | 3 | 0001-3 | 3 | MLL Exon-intron 5 to 11 | 8342 | 250 |
| 120 | 11 | 0001-11 | 11 | MLL Exon-intron 5 to 11 | 8342 | 517 |
| 121 | 62 | 0001-62 | 20 | MLL Exon-intron 5 to 11 | 8342 | 3913 |
| 122 | 58 | 0001-58 | 16 | MLL Exon-intron 5 to 11 | 8342 | 2299 |
| 123 | 125 | 0002-44 | 7 | MLL Exon 25 | 4249 | 2118 |
| 124 | 148 | DapX-5 | 1 | DapX-5 | 499 | 2 |
| 125 | 146 | CreX-5 | 1 | CreX-5 | 535 | 229 |
| 126 | 95 | 0002-14 | 14 | MLL Exon 25 | 4249 | 2206 |
| 127 | 147 | DapX-3 | 1 | DapX-3 | 447 | 85 |
| 128 | 132 | 0002-51 | 14 | MLL Exon 25 | 4249 | 3757 |
| 129 | 137 | 0002-56 | 19 | MLL Exon 25 | 4249 | 3037 |
| 130 | 71 | 0001-71 | 29 | MLL Exon-intron 5 to 11 | 8342 | 5171 |
| 131 | 48 | 0001-48 | 6 | MLL Exon-intron 5 to 11 | 8342 | 5258 |
| 132 | 33 | 0001-33 | 33 | MLL Exon-intron 5 to 11 | 8342 | 2827 |
| 133 | 145 | CreX-3 | 1 | CreX-3 | 407 | 220 |
| 134 | 82 | 0002-1 | 1 | MLL Exon 25 | 4249 | 1890 |
| 135 | 43 | 0001-43 | 1 | MLL Exon-intron 5 to 11 | 8342 | 6966 |
| 136 | 23 | 0001-23 | 23 | MLL Exon-intron 5 to 11 | 8342 | 7450 |
| 137 | 17 | 0001-17 | 17 | MLL Exon-intron 5 to 11 | 8342 | 6493 |
| 138 | 115 | 0002-34 | 34 | MLL Exon 25 | 4249 | 1775 |

TABLE 2-continued

| Random Sorter | Original Sorter | Probe ID | Ranked order of preference | Sequence Description | Sequence Length | Probe Position within sequence |
|---|---|---|---|---|---|---|
| 139 | 129 | 0002-48 | 11 | MLL Exon 25 | 4249 | 3568 |
| 140 | 6 | 0001-6 | 6 | MLL Exon-intron 5 to 11 | 8342 | 3104 |
| 141 | 51 | 0001-51 | 9 | MLL Exon-intron 5 to 11 | 8342 | 8087 |
| 142 | 121 | 0002-40 | 3 | MLL Exon 25 | 4249 | 641 |
| 143 | 159 | TrpnX-M | 1 | TrpnX-M | 489 | 165 |
| 144 | 143 | BioDn-3 | 1 | BioDn-3 | 286 | 73 |
| 145 | 60 | 0001-60 | 18 | MLL Exon-intron 5 to 11 | 8342 | 8175 |
| 146 | 133 | 0002-52 | 15 | MLL Exon 25 | 4249 | 1748 |
| 147 | 80 | 0001-80 | 7 | >MLL Exon-intron 5 to 11 | 8342 | 1493 |
| 148 | 70 | 0001-70 | 28 | MLL Exon-intron 5 to 11 | 8342 | 5791 |
| 149 | 1 | 0001-1 | 1 | MLL Exon-intron 5 to 11 | 8342 | 6881 |
| 150 | 87 | 0002-6 | 6 | MLL Exon 25 | 4249 | 1033 |
| 151 | 9 | 0001-9 | 9 | MLL Exon-intron 5 to 11 | 8342 | 5126 |
| 152 | 40 | 0001-40 | 40 | MLL Exon-intron 5 to 11 | 8342 | 2278 |
| 153 | 156 | ThrX-M | 1 | ThrX-M | 571 | 485 |
| 154 | 104 | 0002-23 | 23 | MLL Exon 25 | 4249 | 3201 |
| 155 | 96 | 0002-15 | 15 | MLL Exon 25 | 4249 | 2073 |
| 156 | 154 | ThrX-3 | 1 | ThrX-3 | 463 | 135 |
| 157 | 68 | 0001-68 | 26 | MLL Exon-intron 5 to 11 | 8342 | 3257 |
| 158 | 69 | 0001-69 | 27 | MLL Exon-intron 5 to 11 | 8342 | 435 |
| 159 | 59 | 0001-59 | 17 | MLL Exon-intron 5 to 11 | 8342 | 3818 |
| 160 | 36 | 0001-36 | 36 | MLL Exon-intron 5 to 11 | 8342 | 8055 |
| 161 | 29 | 0001-29 | 29 | MLL Exon-intron 5 to 11 | 8342 | 8293 |
| 162 | 131 | 0002-50 | 13 | MLL Exon 25 | 4249 | 3121 |

TABLE 3

| Probe ID | SEQ ID NO | Probe Sequence |
|---|---|---|
| 0002-12 | 1 | GTCCTGGCCCGTCTCAGATTTCCAATGCAGCTGTCCAGACCACTCCACCC |
| 0001-66 | 2 | AAAGAATCCTGAATAAATGGGACTTTCTGTTGGTGGAAAGAAATATAGA |
| 0002-32 | 3 | TCCAACTCCTGAAGGCCACATGACTCCTGATCATTTTATCCAAGGACACA |
| 0001-24 | 4 | ATTCAGTCTACAAGTGCCAGGGGTCTACTGTATCCTCTTTTCCGTCTTAA |
| 0001-32 | 5 | AGGCCTTATTTAGGTTTGACCAATTGTCCCAATAATTCCTTTATGGCAAA |
| 0002-25 | 6 | TGAGTTCCAAGAGCTCAGAGGGATCTGCACATAATGTGGCTTACCCTGGA |
| 0001-54 | 7 | AGAGCAGGTTACAAGATAATATATAAAGCACAATCCCATCTTAGTTTGGA |
| LysX-M | 8 | CGCATACGCATGACTACATTACAACGGGCCAGGAAGATTCAAAGTTTGGT |
| 0002-37 | 9 | AACCAGAACATGCAGCCACTTTATGTTCTCCAAACTCTTCCAAATGGAGT |
| 0002-31 | 10 | ACAGTCACTTGGATGGATCTTCATCTTCAGAAATGAAGCAGTCCAGTGCT |
| 0002-29 | 11 | AGTTCTACACCCAGTGTGATGGAGACAAATACTTCAGTATTGGGACCCAT |
| TrpnX-3 | 12 | AAATATTGCGGTATTCGGTCACTAAAGGATTTGCAGCTTGCGGCGGAATC |
| 0002-5 | 13 | CCACCTCACATCAGGGTCTGTGTCTGGCTTGGCATCCAGTTCCTCTGTCT |
| BioB-3 | 14 | GAACGAACAGACTCAGGCGATGTGCTTTATGGCAGGCGCAAACTCGATTT |
| 0001-30 | 15 | CCACAGGATCAGAGTGGACTTTAAGGTAAAGGTGTTCAGTGATCATAAAG |
| 0001-61 | 16 | AGGCATCCTGCTTCTTTGTACCCCAGGAAGTACATAAATGATTGATCTGG |
| 0001-39 | 17 | AGTCTGTTTTGTTGGTATTTAGCAGGTACTATTCCCTGTTTAAACCAGCT |
| 0001-81 | 18 | CCTGTAGTCCCAGCTACTCAGGAGAGTGAGCCAGGAGAATGGCGTGAACC |
| 0001-12 | 19 | TCCTACATCCTTTACAGTTCTTAAATTCCTGGCAGATACCTCTTTGGCTT |
| 0001-2 | 20 | TGGAGTGTAATAAGTGCCGAAACAGCTATCACCCTGAGTGCCTGGGACCA |
| 0001-73 | 21 | AAATCACCCTTCCCTGTATTCACTATTTTTATTTATTATGGATAAAGAGA |

TABLE 3-continued

| Probe ID | SEQ ID NO | Probe Sequence |
|---|---|---|
| 0002-49 | 22 | ACTCTAGGAATAATGTTTCCTCAGTCTCCACCACCGGGACCGCTACTGAT |
| 0002-4 | 23 | CTCCATCCTCTCCATCTTCTGGACAGCGGTCAGCAAGCCCTTCAGTGCCG |
| 0002-22 | 24 | AGGACAGAAACCTAATGCTTCCAGATGGCCCCAAACCTCAGGAGGATGGC |
| 0001-46 | 25 | AAGCACTGATGTCTCAAACAGCATTTGAAAGCAGGAAATGTATGATTTGA |
| 0001-57 | 26 | AATCCCATCTCTCTTAAATTCAGTCTTTATTAGAGTTCTGATCTTTCTGT |
| 0001-31 | 27 | TGGGCCTGAATCCAAACAGGCCACCACTCCAGCTTCCAGGAAGTCAAGCA |
| BioB-5 | 28 | TTCGATCCTCGTCAGGTGCAGGTCAGCACGTTGCTGTCGATTAAGACCGG |
| 0001-52 | 29 | AGAAAATCCAAGCTAGGTTGAAATCTGAATGTTGAGCAGTCAGTGAGACA |
| 0001-72 | 30 | TGTACCACCTTTACAATGAGGAAGGAAAAAGTAGCACAATTTTAAATAGG |
| 0001-20 | 31 | TGCCAGTAAATGTGAAATGGGGTACTAAGTAATAGGTGTTGGGTGAAGGT |
| 0001-13 | 32 | ACTGCACTCCTAAAGCATGACCAGTGCTTGATAAACTCTCCTCCATGCGA |
| ThrX-5 | 33 | AGAAATCACCGATTGCCCTTGTCAACTCAGTCAACCCTTACCGCATTGAA |
| 0002-28 | 34 | GGAGTCCCACTGTCCCCAGCCAGAATCCCAGTAGACTAGCTGTTATCTCA |
| 0001-21 | 35 | ACTGAGTGCCTTTGGCAGGAAATAAATCTATCTCAATGCGTTAATTGGGA |
| 0001-45 | 36 | ATTAAGAGTGTGGTTGGATTATGGGTGACCTTTATTTGTTTCTCTGGTTT |
| 0001-65 | 37 | TTTCCGTCTTAATACAGTGCTTTGCACCCATATATATGCCACCCACAGGA |
| 0001-34 | 38 | TGGAAAGATGTCCATGACATATCACTGAGTGAAAAGAGCAGGTTACAAGA |
| 0001-15 | 39 | CCCACATGTTCTAGCCTAGGAATCTGCTTATTCTAAAGGCCATTTGGCGT |
| 0002-38 | 40 | GCCACAGCGGCAGGCACATCAACAATAAGCCAGGATACTAGCCACCTCAC |
| 0001-35 | 41 | TGGAAAGGACAAACCAGACCTTACAACTGTTTCGTATATTACAGAAAACG |
| 0001-18 | 42 | TTTCCACTGGTATTACCACTTTAGTACTCTGAATCTCCCGCAATGTCCAA |
| 0002-18 | 43 | CCCAGGTATCCAACTTTACCCAGACGGTAGACGCTCCTAATAGCATGGGA |
| 0002-45 | 44 | GGTGACAACTGGTGAGGAAGGAAACTTGAAGCCAGAGTTTATGGATGAGG |
| 0002-13 | 45 | CAGTCTCCACCACCGGGACCGCTACTGATCTTGAATCAAGTGCCAAAGTA |
| 0001-7 | 46 | TGCCCCAAAGAAAAGCAGTAGTGAGCCTCCTCCACGAAAGCCCGTCGAGG |
| 0002-24 | 47 | ACCGGCACCCCTGTTACCACAGAGTGTGGGAGGAACTGCTGCCACAGCGG |
| 0002-19 | 48 | TCAGCCTCTGAAAATCCAGGAGATGGTCCAGTGGCCCAACCAAGCCCCAA |
| 0001-41 | 49 | AGCAGGAAATGTATGATTTGAAGTCTTCAGTTCAAGAAAATCAGCTCTCT |
| 0002-35 | 50 | AGCTCCTGAAATCAGATTCAGACAATAACAACAGTGATGACTGTGGGAAT |
| 0002-36 | 51 | CTAGAGAACTGAATGTTAGTAAAATCGGCTCCTTTGCTGAACCCTCTTCA |
| DapX-M | 52 | TGTCTCGGCATTAATCCGTTTATGTGATGTGTATTCCATTCCGCTCGCCA |
| LysX-3 | 53 | GATCGAACCGGGCCGTTCTCTCGTGGGAGACGCAGGCACAACTCTTTATA |
| 0001-5 | 54 | ACCTCCGGTCAATAAGCAGGAGAATGCAGGCACTTTGAACATCCTCAGCA |
| LysX-5 | 55 | CAACATGGTCATTTAGAAATCGGAGGTGTGGATGCTCTCTATTTAGCGGA |
| 0001-67 | 56 | TGTATATCAAAGCCTCTTCATCTATAAGGAGCTCTTACCAATTAATAAGA |
| 0001-53 | 57 | TTTACTTAGTCTGTCTTTAGCATTTAATTGGGTGTAATCAGTTGCCTATT |
| 0002-7 | 58 | CCCTACAAGTAGTGCGTCAGTTCCAGGACACGTCACCTTAACCAACCCAA |
| 0001-27 | 59 | GAAATAAATACATGTTGGGTGGCAGGGGGAGGTGAAGGGAGGGTGTCTGT |
| PheX-M | 60 | TTTAATACATGAACAGCCTTTGCCAATCGTGGGTGAAATGACGTTGCCGA |

TABLE 3-continued

| Probe ID | SEQ ID NO | Probe Sequence |
|---|---|---|
| PheX-5 | 61 | GCAGATTCAGTAGCAGATGCCGTTCAAAAGGTCGATTTAAGTAGAAGTGC |
| 0001-74 | 62 | AACTTCAAGTTTAGGCTTTTAGCTGGGCACGGTGGCTCACGCTGGTAATC |
| 0002-2 | 63 | AGCAGACGAACACTATCAGCTTCAGCATGTGAACCAGCTCCTTGCCAGCA |
| 0001-75 | 64 | CAGCAGTTCAAGACCAGCCTGGGCAACATAGCAAGACCCTGTCTTTATTT |
| TrpnX-5 | 65 | AAACCCTTACTGCCGGTGAGGCTGAAACGCTGATGAATATGATGATGGCA |
| 0002-20 | 66 | AAGGATTGCTACCCATGTCTCATCACCAGCACTTACATTCCTTCCCTGCA |
| 0001-44 | 67 | GCCCTTTCTTCACAGGTCAGTCAGTACTAAAGTAGTCGTTGCCAGCATCT |
| 0001-76 | 68 | TCAGGAGGCTGAGATAGAAGGATTGTCTTGAGCCCAGGAATTCAAGGCTG |
| 0002-33 | 69 | AGTCTGTTAGATTTGGGGTCACTTAATACTTCATCTCACCGAACTGTCCC |
| 0001-19 | 70 | GGAAACCAAGGATGACTGTGCTTAGAGTATTGCTTTCTTTCTTGATTTGT |
| 0001-22 | 71 | CTCTCCACAGGAGGATTGTGAAGCAGAAAATGTGTGGGAGATGGGAGGCT |
| 0002-54 | 72 | CCTGAAGGCCACATGACTCCTGATCATTTTATCCAAGGACACATGGATGC |
| 0002-9 | 73 | GCATTGGCTCCAGGCGTCACAGTACCTCTTCCTTATCACCCCAGCGGTCC |
| 0001-47 | 74 | ACAAATGGAAAGGACAAACCAGACCTTACAACTGTTTCGTATATTACAGA |
| BioDn-5 | 75 | CGCAAGAGGGCAGACCGATAGAATCATTGGTAATGAGCGCCGGATTACGC |
| 0002-42 | 76 | ACTATCAGAATCTTCCAGTACAGGACAGAAACCTAATGCTTCCAGATGGC |
| 0001-79 | 77 | GCAGTGAGCCGAGATTGCATCATTGCACTCTAGCCTGGACAACAGAGCTA |
| 0002-41 | 78 | CACTAGAACAGTGATTTCTTCAGGTGGAGAGGAACGACTGGCATCCCATA |
| 0002-30 | 79 | TTGACTCCTGAGTATATGGGCCAACGACCATGTAACAATGTTTCTTCTGA |
| 0002-39 | 80 | GAGCTACCATCTGATCTGTCTGTCTTGACCACCCGGAGTCCCACTGTCCC |
| 0001-50 | 81 | TGTTTCTCTGCCATTTCTCAGGGATGTATTCTATTTTGTAGGGAAAAGCC |
| 0001-56 | 82 | TTCTGATCTAAATTCTTTATAGTTGTACATAGCAATCTCACAGGGTTCCT |
| 0001-10 | 83 | AGCAGGTGGGTTTAGCGCTGGGAGAGCTTTGGACAGTGTTGTTAGGTCAC |
| 0002-10 | 84 | TCCCACACCTCCATTTGAGAGGGCAAAGGAATGATCGAGACCAACACACA |
| 0002-43 | 85 | ACTGATGACTGTGGGAATATCCTGCCTTCAGACATTATGGACTTTGTACT |
| 0001-37 | 86 | TGCCAGTGGACTACTAAAACCCAAAGTATATAAGAAGGGTATGGTTGATT |
| 0001-8 | 87 | GCCTCAGCCACCTACTACAGGACCGCCAAGAAAAGAAGTTCCCAAAACCA |
| 0002-26 | 88 | GATGGTGTTGATGATGGGACAGAGAGTGATACTAGTGTCACAGCCACAAC |
| 0001-25 | 89 | AAAGGTGAGGAGAGATTTGTTTCTCTGCCATTTCTCAGGGATGTATTCTA |
| BioB-M | 90 | GGGATCAAAGTCTGTTCTGGCGGCATTGTGGGCTTAGGCGAAACGGTAAA |
| 0001-38 | 91 | TGGAAGGATTCACACCAAAATATTAAGAGTGTGGTTGGATTATGGGTGAC |
| 0001-26 | 92 | ACCCGAAAGTCCATCTATAGGGAGCATGGGTTAAAATAAGCATAGGGCAT |
| 0002-17 | 93 | AGAGCAAGGTCATGGCAACAATCAGGATTTAACTAGGAACAGTAGCACCC |
| BioC-5 | 94 | CGCCAATGCTTGTTCAGGCACGCCAGAAGGATGCCGCAGACCATTATCTG |
| 0002-16 | 95 | TCAGGTGGAGAGGAACGACTGGCATCCCATAATTTATTTCGGGAGGAGGA |
| 0002-21 | 96 | ACTGCTGCAATAACAGCGGCATCTAGCATCTGTGTGCTCCCCTCCACTCA |
| 0001-14 | 97 | TTCCTATCCATCCTGAGGAGTATCAGAGGAAGTAATTCCTTCACATGGAA |
| 0001-16 | 98 | TCCCATGTTCTTACTATAGTTTGTGTATTGCCAAGTCTGTTGTGAGCCCT |

TABLE 3-continued

| Probe ID | SEQ ID NO | Probe Sequence |
|---|---|---|
| PheX-3 | 99 | CGTTTGATGATGTATTGATTCCAGGGGCCATGCAGGAGCTTGAAGCACTC |
| 0001-42 | 100 | TTTTTGGAGTATGTACCACCTTTACAATGAGGAAGGAAAAAGTAGCACAA |
| 0001-55 | 101 | CTATGAATTGAACAACTAGGTGAGCCTTTTAATAGTCCGTGTCTGAGATT |
| 0001-64 | 102 | TGAGTGTCAAAGACTTTAAATAAAGAAAATGCTACTACCAAAGGTGTTGA |
| 0002-46 | 103 | GAAGTATGTGCCCAATTCTACTGATAGTCCTGGCCCGTCTCAGATTTCCA |
| 0002-53 | 104 | GGGCTTACCCCACTCTATGGAGTAAGATCCTATGGTGAAGAAGACATTCC |
| 0002-3 | 105 | AGAATCCAGCCAGAGGACAGACCTCAGTACCACAGTAGCCACTCCATCCT |
| 0002-27 | 106 | ACCTTGAAGCTATCTGGAATGAGCAACAGATCATCCATTATCAACGAACA |
| 0001-78 | 107 | CCGGTTGTGGTAGTGGGTGCTTGGTAATCCTAGCTACTTGGGAGGCTGAG |
| 0001-63 | 108 | ATGTCACACTAATTTTATGCTTTTCATCCTTATTTTCCATCCAAAGTTGT |
| 0002-57 | 109 | CCCAACATCATAAAAAGATCTAAATCTAGCATCATGTATTTTGAACCGGC |
| BioC-3 | 110 | CGAACGTCATCAGGCGTGGCAGGCGGTGGACGAGCGTCCGCATGCTAATC |
| 0001-4 | 111 | TGGGCCTCTGTATCAGTGGGTTCTGTATCCCTGGACTCAACCAACCTTGG |
| 0001-49 | 112 | CCCTCACCCAAATTCCCTAAGTGTTAATATGTTTCTCTGTGTGTATATAT |
| 0001-77 | 113 | CACTTTGGGAAGCCGAAGCAGGCAGATCACTTGAGGTCAGGAGTTGGAGA |
| 0001-28 | 114 | AAGTACCCCTCACCCAAATTCCCTAAGTGTTAATATGTTTCTCTGTGTGT |
| 0002-55 | 115 | AAACACTTCCACCTCTTCAAATTTGCAAAGGACAGTGGTTACTGTAGGCA |
| 0002-11 | 116 | ATTCCATTCTACAGCAGCTCAACTGGGAAGAAGCGAGGCAAGAGATCAGC |
| 0002-8 | 117 | AGCACAAAGTTTCCCATTTGCGGACCAGTTCTTCTGAAGCACACATTCCA |
| 0002-47 | 118 | TAACTTCACACCCTCCCAGCTTCCTAATCATCCAAGTCTGTTAGATTTGG |
| 0001-3 | 119 | ACCACCAGAATCAGGTGAGTGAGGAGGGCAAGAAGGAATTGCTGACCCAC |
| 0001-11 | 120 | CCCTTTCTTCACAGGTCAGTCAGTACTAAAGTAGTCGTTGCCAGCATCTG |
| 0001-62 | 121 | TGGAAACAACCCGAAAGTCCATCTATAGGGAGCATGGGTTAAAATAAGCA |
| 0001-58 | 122 | TGTGAAGGCAAATAGGGTGTGATTTTGTTCTATATTCATCTTTTGTCTCC |
| 0002-44 | 123 | TCAGAACTCCTGAATCTTGGTGAAGGATTGGGTCTTGACAGTAATCGTGA |
| DapX-5 | 124 | GGCAGAACGAACACCACATTTTGACCTTGTAGGGGCCATAGACCATACAT |
| CreX-5 | 125 | AAACTATCCAGCAACATTTGGGCCAGCTAAACATGCTTCATCGTCGGTCC |
| 0002-14 | 126 | TGCCTACAACAGAACCTGTGGATAGTAGTGTCTCTTCCTCTATCTCAGCA |
| DapX-3 | 127 | TGATCAGGCAATTCGGTCAATTGTCACTGTCATCAGAATCTGTCGGCCAA |
| 0002-51 | 128 | CTGCAATAACAGCGGCATCTAGCATCTGTGTGCTCCCCTCCACTCAGACT |
| 0002-56 | 129 | GCAATCCTCCTTCAGGCCTGCTTATTGGGGTTCAGCCTCCTCCGGATCCC |
| 0001-71 | 130 | TGCCATTTGAAGTTATTACTAGCAAAATTACAAATTATTGCCTACTATTC |
| 0001-48 | 131 | ACAACTTATTGTTCTAAGTGCAGAAGTTCAGATATCATTGAGACTGAGAA |
| 0001-33 | 132 | CACTATGAATTGAACAACTAGGTGAGCCTTTTAATAGTCCGTGTCTGAGA |
| CreX-3 | 133 | CTAAGGATGACTCTGGTCAGAGATACCTGGCCTGGTCTGGACACAGTGCC |
| 0002-1 | 134 | TCCTTGGAAGCTCAGCTCAGCTCATTGGAGTCAAGCCGCAGAGTCCACAC |
| 0001-43 | 135 | GCCTCTGTATCAGTGGGTTCTGTATCCCTGGACTCAACCAACCTTGGATT |
| 0001-23 | 136 | TGTTATATGCAAATGCTGCACCATTTTGTCTAGGGACTTGGGCATCCATG |
| 0001-17 | 137 | TCCCATAGCTCTTTGTTTATACCACTCTTAGGTCACTTAGCATGTTCTGT |

TABLE 3-continued

| Probe ID | SEQ ID NO | Probe Sequence |
|---|---|---|
| 0002-34 | 138 | ACCTGAAGATGCTGGGGAGAAAGAACATGTCACTAAGAGTTCTGTTGGCC |
| 0002-48 | 139 | GTGCGTCAGTTCCAGGACACGTCACCTTAACCAACCCAAGGTTGCTTGGT |
| 0001-6 | 140 | AGGGTGGTTTGCTTTCTCTGTGCCAGTAGTGGGCATGTAGAGGTAAGGCA |
| 0001-51 | 141 | TTATAGAGAACCACCATGTGACTATTGGACTTATGTAACTTGTATTACAA |
| 0002-40 | 142 | AGACCAACACACAGATTCTACCCAATCAGCAAACTCCTCTCCAGATGAAG |
| TrpnX-M | 143 | CTCACTGAAGGAAGGAACGGAGCTGGCGTTAGAGACGATTACAAGCGGAG |
| BioDn-3 | 144 | CCGGTGATACTGGTAGTTGGTGTGAAACTCGGCTGTATTAATCACGCGAT |
| 0001-60 | 145 | CCCTCATTACTAGGAAATCATCTCAGGAGAGAAATTAAATCTATAAATGG |
| 0002-52 | 146 | TGGAACAGAGAACTTAAAGATTGATAGACCTGAAGATGCTGGGGAGAAAG |
| 0001-80 | 147 | AGGAGATCGAGACCATCCTGGCTAACACGGTGAAACCCTGTCTCTACTAA |
| 0001-70 | 148 | TGAGAACAAGTTGGAGACATAAACCATTTTACCTCTAAATATTTTAGTGT |
| 0001-1 | 149 | TGTCGTCGCTGCAAATTCTGTCACGTTTGTGGAGGGCAACATCAGGCTAC |
| 0002-6 | 150 | AGGAATTACAGGCACCACGGAAACGCACAGTCAAAGTGACACTGACACCT |
| 0001-9 | 151 | AGTCAGTGAGACACAAACTAGCTAAGAAAGTCAACCCTGCCCACTTGCCA |
| 0001-40 | 152 | TGCATTATTATCTGTTGCAAATGTGAAGGCAAATAGGGTGTGATTTTGTT |
| ThrX-M | 153 | TACAGATAACCTGATCTACCAAGTGGCTAAACGGACCGCAGATTTGTACG |
| 0002-23 | 154 | AAACTTGCTCCCTCTAGTACCCCTTCAAACATTGCCCCTTCTGATGTGGT |
| 0002-15 | 155 | ACTCCATCCATGCAGGCTTTGGGTGAGAGCCCAGAGTCATCTTCATCAGA |
| ThrX-3 | 156 | AAGTGCTGACAAGAGACGCGAGAGACGTGCTTCCGAAGGAGTTTCCATAT |
| 0001-68 | 157 | ACCAGCTAAAGAAATGTTTTGAAGTATTTTAGAGATTTTAGGAAGGAATC |
| 0001-69 | 158 | AAACAGTTAAATTGGAGGTATTGTTTTAATTTCCTGTTCGAAGCCTAGAG |
| 0001-59 | 159 | GCACTTCAAACACTTATGGATATAATTAGATAAATTGGCAAATCTGTAGA |
| 0001-36 | 160 | AAGTCTGGGTGAGTTATACACATGATGCTCTTTTATAGAGAACCACCATG |
| 0001-29 | 161 | TTCTTTTCTAGATCTGTACCAAGTGTGTTCGCTGTAAGAGCTGTGGATCC |
| 0002-50 | 162 | ACCTCAGTACCACAGTAGCCACTCCATCCTCTGGACTCAAGAAAAGACCC |

TABLE 4

| SEQ ID NO | Sequence |
|---|---|
| 163 | CACTTTGCACTGGAACTTACAACACCCGAGCAAGGACGCGACTCTCCCGA |
| 164 | GACACTTCCCCGCCGCTGCCAGGACCCGCTTCTCTGAAAGGCTCTCCTTG |
| 165 | CCAGCCAGCGGTCCGCAACCCTTGCCGCATCCACGAAACTTTGCCCATAG |
| 166 | CTTTGCACTGGAACTTACAACACCCGAGCAAGGAC |
| 167 | CAACCCTTGCCGCATCCACGAAACTTTGCCCATAG |
| 168 | CTCAACGTTAGCTTCACCAACAGGAACTATGACCTCGACTACGACTCGGT |
| 169 | TTAGCTTCACCAACAGGAACTATGACCTCGACTACGACTC |
| 170 | CGAGACCTTCATCAAAAACATCATCATCCAGGACTGTATG |
| 171 | GTATTTCTACTGCGACGAGGAGGAGAACTTCTACCAGCAG |
| 172 | CGTTTATAGCAGTTACACAGAATTTCAATCCTAGTATATAGTACCTAGTA |

TABLE 4-continued

| SEQ ID NO | Sequence |
|---|---|
| 173 | GAGACTGAAAGATTTAGCCATAATGTAAACTGCCTCAAATTGGACTTTGG |
| 174 | CCTTCTAACAGAAATGTCCTGAGCAATCACCTATGAACTTGTTTCAAATG |
| 175 | TTACACAATGTTTCTCTGTAAATATTGCCATTAAATGTAAATAACTTTAA |
| 176 | CATCTCCGTATTGAGTGCGAAGGGAGGTGCCCCTATTATTATTTGACACC |
| 177 | GCCACTCCAGCCGGCGAGAGAAAGAAGAAAAGCTGGCAAAAGGAGTGTTG |
| 178 | GTATTGAGTGCGAAGGGAGGTGCCCCTATTATTATTTG |
| 179 | CTTGTATTTATGGAGGGGTGTTAAAGCCCGCGGCTGAG |
| 180 | AAAACTTTGTGCCTTGGATTTTGGCAAATTGTTTTCCTCACCGCCACCTC |
| 181 | GAGATAGCAGGGGACTGTCCAAAGGGGGTGAAAGGGTGCTCCCTTTATTC |
| 182 | AAAACTTTGTGCCTTGGATTTTGGCAAATTGTTTTCCTC |
| 183 | GGAATGGTTTTTAAGACTACCCTTTCGAGATTTCTGCCTTATGAATATAT |
| 184 | TTTTATCACTTTAATGCTGAGATGAGTCGAATGCCTAAATAGGGTGTCTT |
| 185 | CTCCCATTCCTGCGCTATTGACACTTTTCTCAGAGTAGTTATGGTAACTG |
| 186 | TTATCTTACAACTCAATCCACTTCTTCTTACCTCCCGTTAACATTTTAAT |
| 187 | GATCTTCTCAGCCTATTTTGAACACTGAAAAGCAAATCCTTGCCAAAGTT |
| 188 | TTTCATTGGCAGCTTATTTAACGGGCCACTCTTATTAGGAAGGAGAGATA |
| 189 | CATTAAGTCTTAGGTAAGAATTGGCATCAATGTCCTATCCTGGGAAGTTG |
| 190 | CATTTCCAGTAAAATAGGGAGTTGCTAAAGTCATACCAAGCAATTTGCAG |
| 191 | ATCATTTGCAACACCTGAAGTGTTCTTGGTAAAGTCCCTCAAAAATAGGA |
| 192 | AATCTGGTAATTGATTATTTTAATGTAACCTTGCTAAAGGAGTGATTTCT |
| 193 | GATAATTTTGTCCAGAGACCTTTCTAACGTATTCATGCCTTGTATTTGTA |
| 194 | GTCTAGAAAAACCTGCCAAATATGATGACATCAAGAAGGTGGTGAAGCAG |
| 195 | TACACTGAGCACCAGGTGGTCTCCTCTGACTTCAACAGCGACACCCACTC |
| 196 | CTGGGGCTGGCATTGCCCTCAACGACCACTTTGTCAAGCTCATTTCCTGG |
| 197 | CACTGCCAACGTGTCAGTGGTGGACCTGACCTGCCGTCTAGAAAAACCTG |
| 198 | AAATATGATGACATCAAGAAGGTGGTGAAGCAGGCGTCGGAGGGCCCCCT |
| 199 | CATTGCCCTCAACGACCACTTTGTCAAGCTCATTTCCTG |
| 200 | CTACACTGAGCACCAGGTGGTCTCCTCTGACTTCAACAG |
| 201 | TGATGCTTTTCCTAGATTATTCTCTGGTAAATCAAAGAAGTGGGTTTATG |
| 202 | CTGTCCAGTTAATTTCTGACCTTTACTCCTGCCCTTTGAGTTTGATGATG |
| 203 | TATTCTCTGGTAAATCAAAGAAGTGGGTTTATGGAGGTCCTCTTGTGTCC |
| 204 | GATTTCTGGAAAAGAGCTAGGAAGGACAGGCAACTTGGCAAATCAAAGCC |
| 205 | CACCGCACCCTGGTCTGAGGTTAAATATAGCTGCTGACCTTTCTGTAGCT |
| 206 | GAGAAGCTGAGTCATGGGTAGTTGGAAAAGGACATTTCCACCGCAAAATG |
| 207 | ATTATTCTCTGGTAAATCAAAGAAGTGGGTTTATGGAGGTCC |
| 208 | CTGTCCAGTTAATTTCTGACCTTTACTCCTGCCCTTTGAG |
| 209 | CCTGGTCTGAGGTTAAATATAGCTGCTGACCTTTCTGTAG |
| 210 | GAAAAGAGCTAGGAAGGACAGGCAACTTGGCAAATCAAAG |
| 211 | GGGAGAAGCTGAGTCATGGGTAGTTGGAAAAGGACATTTC |

TABLE 4-continued

| SEQ ID NO | Sequence |
|---|---|
| 212 | GAAAGACAAGGAAGGAACACCTCCACTTACAAAAGAAGATAAGACAGTTG |
| 213 | CAAAGTATGCCAAAGAAGGTCTTATTCGCAAACCAATATTTGATAATTTC |
| 214 | AAATAACACATGGAAAGGACATTTCAGAGTTACCAAAGGGAAACAAAGAA |
| 215 | GCTGTCAAAACCAAATACTTATAAAGAAAGGGAGAGGAAATCTGGAAAA |
| 216 | CTCACTCTAGAATATTTGAGTCTGTAACCTTGCCTAGTAATCGAACTTCT |
| 217 | GTTTATAGAGGATGAGGATTATGACCCTCCAATTAAAATTGCCCGATTAG |
| 218 | AAATGAGAGTAATGATAGGAGAAGCAGAAGGTATTCAGTGTCGGAGAGAA |
| 219 | GACACATTACATAAACTAGGAGAACTTAAGACTACGAACAGAATATTTGG |
| 220 | TGTGTATGAATTCCTTCTTTCAAGTGAACTGATACTAGATTTATTTAAGA |
| 221 | CTTAATTATAAAGTTGGATGTCATTTGAGAAACTCTGGGAATTGGAAGTA |
| 222 | TAAATAAATTCTTATTCAGCTCCTCGAAGCAATAATTACTTTCCAGTAGG |
| 223 | TTAAACCGAAATCAGGAGTAGTTGTGTAAAGAACTTATTGGTAATGATGG |
| 224 | TGCTTGTGGATACATTGTAACAAATGCTTATAAATCATTTCCAAACTAAT |
| 225 | CCAAGGAAAACAGTAGGTGTGGTATCAATATAGGAAACAAATAAGTATTT |
| 226 | TAATCATTAAGAAATACTAATTTAAGTATGGCAAAGGAAAGCACAGGTGC |
| 227 | TTTCTAGCCTATTCAAATCAATCTGGTCATTTATGGTACTTTCCTATTAG |
| 228 | CAATAACAGCATACATTTCTTGACTGGTTGAATTTCATTAACTATTTGGC |
| 229 | GCATTTGTGTTTCTTAGGTGACAGTTGCTAGGTAGAATTGAATTAAATAT |
| 230 | TTAACATTTCTCAATATCAGGCAGAGATCATATTTAAACAGTTTCAATCT |
| 231 | CTGTGTATTTGACTGTGCTTGGGTATATTATACTTTTCTTACTGATTGAG |
| 232 | AAACTGACTTTATGGAGAGATAACCCTGTTTACCTTTAGAAAGAAGGAAG |
| 233 | AAAATAAACCCTGTGATTGTGATGCTTAACTTAATTTTCTACAGTGAATC |
| 234 | GAATAATTTGGGACATTGCCAGGAATCAGAATAGTTTACTATCTGAAGTA |
| 235 | ATGAAATTGAGGGATAGATACAGTAAGTGAGTTGTCTAAGATTACATAGT |
| 236 | GCTTTCCAAGTGATTTCACATAAATTATTTATTCCTTACAGTGCTCAAAT |
| 237 | ATTGTGATAAGATTTTATATTAATTGTGCTGTTAGGAGTTTTGGCTGTTT |
| 238 | TTTCATGAGAAGTCATTCAGTATCATTAAGTATGCTGATTTGTCTCCTTT |
| 239 | AGAAATTTATTTGGGGTTCAGATTCACATGTTGTAGGTTAGTTATATACT |
| 240 | GGATCTCAAATGTACAGAAATCACATCTAAATGTCAATTCCTGAGTTAAG |
| 241 | CTGTATGTTTCTGCCATTATACTTATTTGCTTACCTGATTTAAAGTTGTC |
| 242 | TATTAATCAGTTTGTTTAAATAGACCATCTTTCTTGAGAACTTGTGCAAA |
| 243 | GTATCTATAGTTTGAAATTAGGACTATCCTCTGTGTACTATGCACCAAAG |
| 244 | TCTGTAATAAAGCTGTATGGCTGGGTCCATTTATTTCAATATTAGTTATT |
| 245 | CCAACTATAACTGAAAATAGGATGCTTCCCTAAGTTTTAGTAAAGGATTT |
| 246 | GTCTTTGAAGAGGAGAATTTCAGCCTTTTCTTAAATAGTCCAATACTTTA |

TABLE 5

| SEQ ID NO | Name | Sequence Length | Probe Position within fragment | Probe position within gene sequence |
|---|---|---|---|---|
| 163 | CMYC_Exon1_NT008046.14[1_to_366]_1 | 366 | 195 | 195 |
| 164 | CMYC_Exon1_NT008046.14[1_to_366]_2 | 366 | 273 | 273 |
| 165 | CMYC_Exon1_NT008046.14[1_to_366]_3 | 366 | 134 | 134 |
| 166 | CMYC_Exon1_NT008046.14[1_to_366]_short_1 | 366 | 197 | 197 |
| 167 | CMYC_Exon1_NT008046.14[1_to_366]_short_2 | 366 | 149 | 149 |
| 168 | CMYC_Exon2_NT008046.14[1991_to_2762]_1 | 772 | 22 | 2012 |
| 169 | CMYC_Exon2_NT008046.14[1991_to_2762]_short_1 | 772 | 29 | 2019 |
| 170 | CMYC_Exon2_NT008046.14[1991_to_2762]_short_2 | 772 | 378 | 2368 |
| 171 | CMYC_Exon2_NT008046.14[1991_to_2762]_short_3 | 772 | 78 | 2068 |
| 172 | CMYC_Exon3_NT008046.14[4141_to_5168]_1 | 1028 | 863 | 5003 |
| 173 | CMYC_Exon3_NT008046.14[4141_to_5168]_2 | 1028 | 671 | 4811 |
| 174 | CMYC_Exon3_NT008046.14[4141_to_5168]_3 | 1028 | 583 | 4723 |
| 175 | CMYC_Exon3_NT008046.14[4141_to_5168]_4 | 1028 | 808 | 4948 |
| 176 | CMYC_Intron1_NT008046.14[1110_to_1410]_1 | 301 | 158 | 1267 |
| 177 | CMYC_Intron1_NT008046.14[1110_to_1410]_2 | 301 | 252 | 1361 |
| 178 | CMYC_Intron1_NT008046.14[1110_to_1410]_short_1 | 301 | 165 | 1274 |
| 179 | CMYC_Intron1_NT008046.14[1110_to_1410]_short_3 | 301 | 211 | 1320 |
| 180 | CMYC_Intron1_NT008046.14[1551_to_1880]_1 | 330 | 54 | 1604 |
| 181 | CMYC_Intron1_NT008046.14[1551_to_1880]_2 | 330 | 243 | 1793 |
| 182 | CMYC_Intron1_NT008046.14[1551_to_1880]_short_1 | 330 | 54 | 1604 |
| 183 | CMYC_Intron1_NT008046.14[367_to_1110]_1 | 744 | 222 | 588 |
| 184 | CMYC_Intron1_NT008046.14[367_to_1110]_2 | 744 | 37 | 403 |
| 185 | CMYC_Intron1_NT008046.14[367_to_1110]_4 | 744 | 89 | 455 |
| 186 | CMYC_Intron2_NT008046.14[2763_to_3400]_1 | 637 | 262 | 3024 |
| 187 | CMYC_Intron2_NT008046.14[2763_to_3400]_4 | 637 | 527 | 3289 |
| 188 | CMYC_Intron2_NT008046.14[2763_to_3400]_5 | 637 | 55 | 2817 |
| 189 | CMYC_Intron2_NT008046.14[3419_to_3709]_1 | 291 | 145 | 3563 |
| 190 | CMYC_Intron2_NT008046.14[3419_to_3709]_2 | 291 | 1 | 3419 |
| 191 | CMYC_Intron2_NT008046.14[3419_to_3709]_3 | 291 | 53 | 3471 |
| 192 | CMYC_Intron2_NT008046.14[3996_to_4140]_1 | 145 | 78 | 4073 |
| 193 | CMYC_Intron2_NT008046.14[3996_to_4140]_2 | 145 | 21 | 4016 |
| 194 | GAPDH_Exon8_NT009759.15[3050_to_3462]_1 | 413 | 217 | 3266 |
| 195 | GAPDH_Exon8_NT009759.15[3050_to_3462]_2 | 413 | 300 | 3349 |
| 196 | GAPDH_Exon8_NT009759.15[3050_to_3462]_3 | 413 | 364 | 3413 |
| 197 | GAPDH_Exon8_NT009759.15[3050_to_3462]_4 | 413 | 182 | 3231 |
| 198 | GAPDH_Exon8_NT009759.15[3050_to_3462]_5 | 413 | 234 | 3283 |
| 199 | GAPDH_Exon8_NT009759.15[3050_to_3462]_short_2 | 413 | 374 | 3423 |
| 200 | GAPDH_Exon8_NT009759.15[3050_to_3462]_short_3 | 413 | 299 | 3348 |
| 201 | GAPDH_Intron2_NT009759.15[328_to_1959]_1 | 1632 | 582 | 909 |
| 202 | GAPDH_Intron2_NT009759.15[328_to_1959]_2 | 1632 | 1196 | 1523 |
| 203 | GAPDH_Intron2_NT009759.15[328_to_1959]_3 | 1632 | 599 | 926 |
| 204 | GAPDH_Intron2_NT009759.15[328_to_1959]_5 | 1632 | 1049 | 1376 |
| 205 | GAPDH_Intron2_NT009759.15[328_to_1959]_6 | 1632 | 928 | 1255 |
| 206 | GAPDH_Intron2_NT009759.15[328_to_1959]_7 | 1632 | 693 | 1020 |
| 207 | GAPDH_Intron2_NT009759.15[328_to_1959]_short_1 | 1632 | 597 | 924 |
| 208 | GAPDH_Intron2_NT009759.15[328_to_1959]_short_2 | 1632 | 1196 | 1523 |
| 209 | GAPDH_Intron2_NT009759.15[328_to_1959]_short_3 | 1632 | 936 | 1263 |
| 210 | GAPDH_Intron2_NT009759.15[328_to_1959]_short_4 | 1632 | 1057 | 1384 |
| 211 | GAPDH_Intron2_NT009759.15[328_to_1959]_short_5 | 1632 | 691 | 1018 |
| 212 | MLL_Exon3_AP001267.4[1_to_2654]_10 | 2654 | 491 | 491 |
| 213 | MLL_Exon3_AP001267.4[1_to_2654]_2 | 2654 | 1402 | 1402 |
| 214 | MLL_Exon3_AP001267.4[1_to_2654]_3 | 2654 | 199 | 199 |
| 215 | MLL_Exon3_AP001267.4[1_to_2654]_4 | 2654 | 2361 | 2361 |
| 216 | MLL_Exon3_AP001267.4[1_to_2654]_5 | 2654 | 1618 | 1618 |
| 217 | MLL_Exon3_AP001267.4[1_to_2654]_6 | 2654 | 779 | 779 |
| 218 | MLL_Exon3_AP001267.4[1_to_2654]_7 | 2654 | 1058 | 1058 |
| 219 | MLL_Intron1_AP001267.4[10100_to_12332]_1 | 2233 | 339 | 10438 |
| 220 | MLL_Intron1_AP001267.4[10100_to_12332]_10 | 2233 | 1609 | 11708 |
| 221 | MLL_Intron1_AP001267.4[10100_to_12332]_2 | 2233 | 1809 | 11908 |
| 222 | MLL_Intron1_AP001267.4[10100_to_12332]_3 | 2233 | 988 | 11087 |
| 223 | MLL_Intron1_AP001267.4[10100_to_12332]_4 | 2233 | 803 | 10902 |
| 224 | MLL_Intron1_AP001267.4[10100_to_12332]_6 | 2233 | 1270 | 11369 |
| 225 | MLL_Intron1_AP001267.4[10100_to_12332]_7 | 2233 | 1147 | 11246 |
| 226 | MLL_Intron1_AP001267.4[10100_to_12332]_8 | 2233 | 391 | 10490 |
| 227 | MLL_Intron1_AP001267.4[12670_to_14434]_1 | 1765 | 401 | 13070 |
| 228 | MLL_Intron1_AP001267.4[12670_to_14434]_2 | 1765 | 1204 | 13873 |
| 229 | MLL_Intron1_AP001267.4[12670_to_14434]_3 | 1765 | 876 | 13545 |
| 230 | MLL_Intron1_AP001267.4[12670_to_14434]_4 | 1765 | 1036 | 13705 |
| 231 | MLL_Intron1_AP001267.4[12670_to_14434]_6 | 1765 | 1277 | 13946 |
| 232 | MLL_Intron1_AP001267.4[12670_to_14434]_7 | 1765 | 89 | 12758 |
| 233 | MLL_Intron1_AP001267.4[12670_to_14434]_8 | 1765 | 454 | 13123 |
| 234 | MLL_Intron1_AP001267.4[12670_to_14434]_9 | 1765 | 625 | 13294 |
| 235 | MLL_Intron1_AP001267.4[27613_to_29591]_1 | 1979 | 994 | 28606 |
| 236 | MLL_Intron1_AP001267.4[27613_to_29591]_2 | 1979 | 939 | 28551 |
| 237 | MLL_Intron1_AP001267.4[27613_to_29591]_3 | 1979 | 1304 | 28916 |
| 238 | MLL_Intron1_AP001267.4[27613_to_29591]_7 | 1979 | 478 | 28090 |

TABLE 5-continued

| SEQ ID NO | Name | Sequence Length | Probe Position within fragment | Probe position within gene sequence |
|---|---|---|---|---|
| 239 | MLL__Intron1__AP001267.4[27613__to__29591]_9 | 1979 | 1417 | 29029 |
| 240 | MLL__Intron1__AP001267.4[30450__to__31832]_10 | 1383 | 844 | 31293 |
| 241 | MLL__Intron1__AP001267.4[30450__to__31832]_2 | 1383 | 1027 | 31476 |
| 242 | MLL__Intron1__AP001267.4[30450__to__31832]_3 | 1383 | 550 | 30999 |
| 243 | MLL__Intron1__AP001267.4[30450__to__31832]_6 | 1383 | 1095 | 31544 |
| 244 | MLL__Intron1__AP001267.4[30450__to__31832]_7 | 1383 | 1190 | 31639 |
| 245 | MLL__Intron1__AP001267.4[30450__to__31832]_8 | 1383 | 680 | 31129 |
| 246 | MLL__Intron1__AP001267.4[30450__to__31832]_9 | 1383 | 21 | 30470 |

TABLE 6

| | Chromosomal Location | Structure/Function | Occurrence | Reference |
|---|---|---|---|---|
| Nuclear transcripttion factors | | | | |
| LAF-4 | 2q11 | transcription factor | ALL | GenBank Accession No. AF422798 (Huret, 2001) |
| AF4 (MLLT2, FEL) | 4q21 | transcription factor | ALL t-ALL AML | (Nakamura, 1993) (Raffini, 2002) |
| AF5α | 5q12 | | | (Taki, 1996) |
| AF5q31 | 5q31 | | | |
| AF6q21 (FKHRL1) | 6q21 | forkhead transcription factor | t-AML | (Hillion, 1997) |
| AF9 (MLLT3) | 9p22 | transcriptional activator | AML ALL t-AML | (Nakamura, 1993) (Langer, 2003) (Whitmarsh, 2003) |
| AF10 | 10p12 | leucine zipper protein 2 α-helical domains | t-AML | (Megonigal, 2000) |
| MLL | 11q23 | | de novo AML t-AML | |
| AF17 | 17q21 | | | |
| ENL (MLLT1, LTG19) | 19p13.3 | transcriptional activator | ALL AML T-cell ALL t-AML | (Tkachuk, 1992) (Yamamoto, 1993) (Iida, 1993) (Chervinsky, 1995) (Rubnitz, 1996) (Moorman, 1998) (LoNigro, 2002) |
| AFX | Xq13 | forkhead transcription factor | | (Corral, 1993) |
| Proteins involved in transcripttional regulation | | | | |
| CBP | 16p13 | transcriptional adaptor/ co-activator; histone acetyl transferase | MDS (RAEB-T) t-MDS (RAEB-T) t-CMML t-AML t-ALL (B-lineage) T-cell ALL | (Taki, 1997) (Satake, 1997) (Sobulo, 1997) (Rowley, 1997) (Hayashi, 2000) (Sugita, 2000) |
| ELL (MEN) | 19p13.1 | RNA polymerase II elongation factor | AML t-AML | (Thirman, 1994) (Mitani, 1995) (Rubnitz, 1996) (Shilatifard, 1996) (Johnstone, 2001) (Maki, 1999) (Moorman, 1998) (LoNigro, 2002) (Megonigal, 2000) |
| p300 | 22q13 | transcriptional co-activator | | |
| Nuclear proteins of unknown | | | | |

TABLE 6-continued

| | Chromosomal Location | Structure/Function | Occurrence | Reference |
|---|---|---|---|---|
| function | | | | |
| AF3p21 | 3p21 | SH3 domain, bipartite nuclear localization signal, proline rich domain, homo-oligomerization domain | t-AML | (Sano, 2001) (Hayakawa, 2001) |
| LCX (TET1) | 10q22 | CXXC domain, nuclear localization signals, coiled-coil motif | de novo AML | (Ono, 2002) (Lorsbach, 2003) |
| AF15q14 | | | | (Hayette, 2000) |
| Cytoplasmic proteins | | | | |
| AF1p (eps15) | 1p32 | EGFR pathway tyrosine kinase substrate | AUL (M0) CMML ALL | (Bernard, 1994) (Wong, 1994) (Rogaia, 1997) |
| AF1q | 1q21 | mRNA destabilizing consensus sequences cytokine-like features | AML | (Tse, 1995) (So, 2000) (Busson-Le Coniat, 1999) |
| GMPS | 3q24 | amidotransferease | t-AML | (Pegram, 2000) |
| LPP | 3q28 | | | |
| GRAF | 5q31 | | | |
| AF6 | 6q27 | Ras binding protein | AML t-AML T-cell ALL B-lineage ALL | (Prasad, 1993) (Taki, 1996) (Martineau, 1998) (Joh, 1997) (Mitterbauer, 2000) (Akao, 2000) |
| CDK6 | 7q21 | kinase | | |
| FBP17 | 9q34 | | | |
| ABI-1 | 10p11.2 | | | |
| CBL | 11q23.3 | proline-rich domain, ubiquitin-associated domain, leucine zipper domain, zinc finger domain, tyrosine kinase binding domain, linker region, ring finger domain | de novo AML | (Fu, 2003) |
| MPFYVE | 15q14 | FYVE domain phosphotidyl-inositol-3 phosphate (PtdIns(3)P binding protein | de novo AML | (Chinwalla, 2003) |
| GAS7 | 17p13 | | | (Megonigal, 2000) |
| LASP1 | 17q21 | LIM and SH3 domains | AML | (Strehl, 2003) |
| MSF | 17q25 | septin GTP-binding domain lacks coiled-coil domain in C-terminus | | (McIlhatton, 2001) |
| EEN | 19p13 | Src homology 3 (SH3) protein | AML | (So, 1997) |
| hCDCrel | 22q11 | | | (Megonigal, 1998) |
| SEPTIN6 | Xq23 | | | (Slater, 2002) |
| Cell membrane proteins | | | | |
| CALM | 11q14-q21 | clathrin assembly protein | AML | (Wechsler, 2003) |
| LARG | 11q23 | | | |
| GPHN | 14q23.3 | | | |
| MYO1F | 19p13.2-19p13.3 | head domain with conserved ATP- and actin-binding sites, neck domain with IQ motif, tail domain | AML | (LoNigro, 2002) |
| Golgi/Endo-plasmic reticulum | | | | |
| ALKALINE | 19p13 | | | (LoNigro, 2002) |

TABLE 6-continued

| | Chromosomal Location | Structure/Function | Occurrence | Reference |
|---|---|---|---|---|
| CERAMIDASE Ribosomal protein | | | | |
| RPS3 | 11q13.3-11q13.5 | | AML | (LoNigro, 2003) |
| MIFL | | | | U.S. Provisional Application No. 60/599,385 |
| MAM L2 | 11q21 | Mastermind-Like transcriptional coactivator for mammalian Notch receptors (GenBank No. AY040322) | | MLL exon 7 to position 1799 of MAML2 |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

REFERENCES

1. Fortune, J. M. & Osheroff, N. (2000) *Prog Nucleic Acid Res and Molecular Biology* 64, 221-53.
2. Felix, C. A. (2001) *Med Pediatr Oncol* 36, 525-535.
3. Rowley, J. D. & Olney, H. J. (2002) *Genes Chromosomes Cancer* 33, 331-45.
4. Knudson, A. G. (1992) *Sem Cancer Biol* 3, 99-106.
5. Woessner, R. D., Mattern, M. R., Mirabelli, C. K., Johnson, R. K. & F. H., D. (1991) *Cell Growth Differ* 2, 209-14.
6. Isaacs, R. J., Davies, S. L., Sandri, M. I., Redwood, C., Wells, N. J. & Hickson, I. D. (1998) *Biochim Biophys Acta* 1400, 121-37.
7. Megonigal, M. D., Cheung, N. K., Rappaport, E. F., Nowell, P. C., Wilson, R. B., Jones, D. H., Addya, K., Leonard, D. G., Kushner, B. H., Williams, T. M., Lange, B. J. & Felix, C. A. (2000) *Proc Natl Acad Sci USA* 97, 2814-9.
8. Raffini, L. J., Slater, D. J., Rappaport, E. F., Lo Nigro, L., Cheung, N.-K. V., Biegel, J. A., Nowell, P. C., Lange, B. J. & Felix, C. A. (2002) *Proc Natl Acad Sci USA* 99, 4568-4573.
9. Kushner, B. H., Cheung, N. K., Kramer, K., Heller, G. & Jhanwar, S. C. (1998) *J Clin Oncol* 16, 3880-3889.
10. Lovett, B. D., Lo Nigro, L., Rappaport, E. F., Blair, I. A., Osheroff, N., Zheng, N., Megonigal, M. D., Williams, W. R., Nowell, P. C. & Felix, C. A. (2001) *Proc Natl Acad Sci USA* 98, 9802-9807.
11. Whitmarsh, R., Saginario, C., Zhuo, Y., Hilgenfeld, E., Rappaport, E. F., Megonigal, M. D., Carroll, M., Liu, M., Osheroff, N., Cheung, N.-K. V., Slater, D. J., Ried, T., Knutsen, T., Blair, I. A. & Felix, C. A. (2003) *Oncogene* 22, 8448-8459.
12. Bromberg, K. D. & Osheroff, N. (2001) *Biochem* 40, 8410-8418.
13. Ueda, T., Tsuji, K., Yoshino, H., Ebihara, Y., Yagasaki, H., Hisakawa, H., Mitsui, T., Manabe, A., Tanaka, R., Kimio, K., Ito, M., Yasukawa, K. & Nakahata, T. (2000) *J Clin Invest* 105, 1013-1021.
14. Stong, R., Korsmeyer, S., Parkin, J., Arthur, D. & Kersey, J. (1985) *Blood* 65, 21-31.
15. Pocock, C. F., Malone, M., Booth, M., Evans, M., Morgan, G., Greil, J. & Cotter, F. E. (1995) *Br J Haematol* 90, 855-67.
16. Lozzio, B. B., Lozzio, C. B., Bamberger, E. G. & Feliu, A. S. (1981) *Proc Soc Exp Biol Med* 166, 546-50.
17. Livak, K. J. & Schmittgen, T. D. (2001) *Methods* 25, 402-408.
18. Harlow, E. & Lane, D. (1999) *Using Antibodies: A Laboratory Manual* (Cold Spring Harbor Laboratory).
19. Cheung, V. G. & Nelson, S. F. (1996) *Proc Natl Acad Sci USA* 93, 14676-14679.
20. Gelmini, S., Orlando, C., Sestini, R., Vona, G., Pinzani, P., Ruocco, L. & Pazzagli, M. (1997) *Clin Chem* 43, 752-8.
21. Heid, C. A., Stevens, J., Livak, K. J. & Williams, P. M. (1996) *Genome Res* 6, 986-94.
22. Holland, P. M., Abramson, R. D., Watson, R. & Gelfand, D. H. (1991) *Proc Natl Acad Sci USA* 88, 7276-80.
23. Pongers-Willemse, M. J., Verhagen, O. J., Tibbe, G. J., Wijkhuijs, A. J., de Haas, V., Roovers, E., van der Schoot, C. E. & van Dongen, J. J. (1998) *Leukemia* 12, 2006-14.
24. Lovett, B. D., Strumberg, D., Blair, I. A., Pang, S., Burden, D. A., Megonigal, M. D., Rappaport, E. F., Rebbeck, T. R., Osheroff, N., Pommier, Y. G. & Felix, C. A. (2001) *Biochemistry* 40, 1159-70.
25. Blanco, J. G., Dervieux, T., Edick, M. J., Mehta, P. K., Rubnitz, J. E., Shurtleff, S. A., Raimondi, S. C., Behm, F. G., Pui, C.-H. & Relling, M. V. (2001) *Proc Natl Acad Sci USA* 98, 10338-43.
26. Ford, A. M., Ridge, S. A., Cabrera, M. E., Mahmoud, H., Steel, C. M., Chan, L. C. & Greaves, M. (1993) *Nature* 363, 358-360.
27. Gale, K., Ford, A., Repp, R., Borkhardt, A., Keller, C., Eden, O. & Greaves, M. (1997) *Proc Natl Acad Sci USA* 94, 13950-13954.
28. Megonigal, M. D., Rappaport, E. F., Jones, D. H., Williams, T. M., Lovett, B. D., Kelly, K. M., Lerou, P. H., Moulton, T., Budarf, M. L. & Felix, C. A. (1998) *Proc Natl Acad Sci USA* 95, 6413-6418.
29. Maia, A. T., Koechling, J., Corbett, R., Metzler, M., Wiemels, J. L. & Greaves, M. (2004) *Genes, Chromosomes & Cancer* 39, 335-340.
30. Krishnan, A., Bhatia, S., Slovak, M. L., Arber, D. A., Niland, J. C., Nademanee, A., Fung, H., Bhatia, R., Kashyap, A., Molina, A., O'Donnell, M. R., Parker, P. A., Sniecinski, I. & Snyder, D. S. (2000) *Blood* 95, 1588-1593.
31. Liang, F., Han, M., Romanienko, P. J. & Jasin, M. (1998) *Proc Natl Acad Sci USA* 95, 5172-5177.

32. Capranico, G., Jaxel, C., Roberge, M., Kohn, K. W. & Pommier, Y. (1990) *Nucleic Acids Res* 18, 4553-4559.
33. Cozzio, A., Passegue, E., Ayton, P. M., Karsunky, H., Cleary, M. L. & Weissman, I. L. (2003) *Genes Dev* 17, 3029-35.
34. Boyd, K. E., Wells, J., Gutman, J., Bartley, S. M. & Farnham, P. J. (1998) *Proc Natl Acad Sci USA* 95, 13887-92.
35. Langer, T., Metzler, M., Reinhardt, D., Viehmann, S., Borkhardt, A., Reichel, M., Stanulla, M., Schrappe, M., Creutzig, U., Ritter, J., Leis, T., Jacobs, U., Harbott, J., Beck, J. D., Rascher, W. & Repp, R. (2003) *Genes Chromosomes Cancer* 36, 393-401.
36. Felix, C. A., Hosler, M. R., Slater, D. J., et al. (1998) *J. Pediatr. Hematol/Oncol* 20:299-308.
37. Felix, C. A., Jones, D. H. (1998) *Leukemia* 12:976-981.
38. Slater, D. J., Hilgenfeld, E., Rappaport, E. F. et al. (2002) *Oncogene* 21:4706-4714.
39. Megonigal, M. D. Rappaport E. F., Wilson, R. B., et al. (2000) *PNAS* 97:9597-9602.
40. Pegram, L. D., Megonigal, M. D., Lange, B. J., et al. (2000) *Blood* 96:4360-4362.
41. Felix, C. A., Kim, C. S., Megonigal, M. D., et al. (1997) *Blood* 90:4679-4686.
42. Lo Nigro, L., Rappaport E., Slater, D., et al. (1999) *Proc ASCO* 18:565a.
43. Lo Nigro, L., Slater, D. J., Rappaport, E. F., et al. (2002) *Blood* 100(Suppl 1):531a.
44. Dudoit, S. and Yang, Y. H. (2002) Bioconductor R packages for exploratory analysis and normalization of cDNA microarray data. In: The analysis of Gene Expression Data: Methods and Software; Parmigiani, et al. (Ed) pp. 73-101; New York: Springer.
45. Dudoit, S., Speed, T. P., Callow, M. J. (2002) *Statistica Sinica* 12:111-139.
46. Huret J L, et al. (2001) Leukemia, 15(6):987-9.
47. Nakamura T, et al. (1993) Proc Natl Acad Sci USA. 15; 90(10):4631-5.
48. Taki T, et al. (1996) Oncogene. 13(10):2121-30.
49. Hillion J, et al. (1997) Blood. 90(9):3714-9.
50. Moorman A V, et al. (1998) Leukemia. 12(5):805-10.
51. Rubnitz J E, et al. (1996) Blood. 87(11):4804-8.
52. Chervinsky D S, et al. (1995) Genes Chromosomes Cancer. 14(1):76-84.
53. Yamamoto K, et al. (1993) Oncogene. 8(10):2617-25.
54. Iida S, et al. (1993) Oncogene. 8(11):3085-92.
55. Tkachuk D C, et al. (1992) Cell. 71(4):691-700.
56. Corral J, et al. (1993) Proc Natl Acad Sci USA. 90(18): 8538-42.
57. Taki T, et al. (1997) Blood. 89(11):3945-50.
58. Satake N, et al. (1997) Genes Chromosomes Cancer. 20(1):60-3.
59. Sobulo O M, et al. (1997) Proc Natl Acad Sci USA. 94(16):8732-7.
60. Rowley J D, et al. (1997) Blood. 90(2):535-41.
61. Hayashi Y, et al. (2000) Cancer Res. 60(4):1139-45.
62. Sugita K, et al. (2000) Genes Chromosomes Cancer. 27(3):264-9.
63. Thirman M J, et al. (1994) Proc Natl Acad Sci USA. 91(25):12110-4.
64. Shilatifard A, et al. (1996) Science. 271(5257):1873-6.
65. Maki K, et al. (1999) Blood. 93(10):3216-24.
66. Mitani K, et al. (1995) Blood. 85(8):2017-24.
67. Sano K. (2001) Leuk Lymphoma. 42(4):595-602.
68. Hayakawa A, et al. (2001) Genes Chromosomes Cancer. 30(4):364-74.
69. Ono R, et al. (2002) Cancer Res. 62(14):4075-80.
70. Lorsbach R B, et al. (2003) Leukemia. 17(3):637-41.
71. Hayette S, et al. (2000) Oncogene. 19(38):4446-50.
72. Bernard O A, et al. (1994) Oncogene. 9(4):1039-45.
73. Wong W T, et al. (1994) Oncogene. 9(6):1591-7.
74. Rogaia D, et al. (1997) Cancer Res. 57(5):799-802.
75. Tse W, et al. (1995) Blood. 85(3):650-6.
76. So C W, et al. (2000) Leukemia. 14(4):594-601.
77. Busson-Le Coniat M, et al. (1999) Leukemia. 13(2):302-6.
78. Pegram L D, et al. (2000) Blood. 96(13):4360-2.
79. Prasad R, et al. (1993) Cancer Res. 53(23):5624-8.
80. Taki T, et al. (1996) Oncogene. 13(10):2121-30.
81. Martineau M, et al. (1998) Leukemia. 12(5):788-91.
82. Joh T, et al. (1997) Oncogene. 15(14):1681-7.
83. Mitterbauer G, et al. (2000) Br J. Haematol. 109(3):622-8.
84. Akao Y, et al. (2000) Genes Chromosomes Cancer. 27(4): 412-7.
85. Fu J F, et al. (2003) Genes Chromosomes Cancer. 37(2): 214-9.
86. Chinwalla V, et al. (2003) Oncogene. 22(9):1400-10.
87. Strehl S, et al. (2003) Oncogene. 22(1):157-60.
88. McIlhatton M A, et al. (2001) Oncogene. 20(41):5930-9.
89. So C W, et al. (1997) Proc Natl Acad Sci USA. 94(6): 2563-8.
90. Wechsler D S, et al. (2003) Genes Chromosomes Cancer. 36(1):26-36.
91. Lo Nigro L, et al. (2003) Blood. 102:184-185b.

What is claimed is:

1. A method for identifying DNA sequences present in topoisomerase II-DNA complexes in cells, comprising:

a) isolating topoisomerase II-DNA complexes from the cell by lysing said cells and immunoprecipitating said topoisomerase II-DNA complexes with topoisomerase II antibodies;
b) amplifying the DNA present in said isolated topoisomerase II-DNA complexes via polymerase chain reaction; and
c) identifying the sequences present in said amplified DNA, thereby identifying the sequences present in said topoisomerase II-DNA complexes.

2. The method of claim 1, wherein the DNA in said topoisomerase II-DNA complexes is genomic DNA.

3. The method of claim 1, wherein the identification of the DNA sequences in step c) comprises further amplifying the amplified DNA from step b) with gene specific primers.

4. The method of claim 1, wherein the identification of the sequences in step c) comprises further amplifying the amplified DNA from step b) by real-time PCR.

5. The method of claim 1, wherein the identification of the sequences in step c) comprises hybridizing the amplified DNA from step b) with a microarray.

6. The method of claim 5, wherein said microarray comprises myeloid lymphoid leukemia (MLL) breakpoint cluster region (bcr) oligonucleotide sequences.

7. The method of claim 6, wherein said MLL bcr oligonucleotide sequences hybridize to non-repetitive MLL bcr sequences.

8. The method of claim 6, wherein said microarray further comprises oligonucleotide sequences from the Alu region between nucleotide positions 663-1779 in the MLL bcr.

9. The method of claim 6, wherein said microarray further comprises control sequences which are not involved in MLL translocations.

10. The method of claim 6, wherein said microarray further comprises oligonucleotide sequences from MLL partner genes.

11. The method of claim 6, wherein said MLL bcr oligonucleotide sequences specifically hybridize to the MLL bcr under very high stringency conditions and wherein said bcr of the MLL gene is 8.3 kilobases between exons 5-11 of the MLL gene at chromosome band 11q23.

12. The method of claim 5, wherein said microarray comprises oligonucleotide sequences from myeloid lymphoid leukemia (MLL) partner genes.

13. The method of claim 1, wherein said cells are CD34+ cells.

14. The method of claim 1, wherein said amplified DNA of step b) comprises sequences from the myeloid lymphoid leukemia (MLL) gene.

15. The method of claim 1, wherein said cells are exposed to an agent suspected of modulating formation of topoisomerase cleavage complexes.

16. The method of claim 1, wherein said cells are obtained from a human.

17. The method of claim 1, wherein the identification of MLL sequences in the topoisomerase II-DNA complexes indicates the potential to develop MLL translocations.

18. The method of claim 1, wherein said polymerase chain reaction of step b) is degenerative oligonucleotide polymerase chain reaction.

19. The method of claim 1, wherein said immunoprecipitation is performed without crosslinking.

* * * * *

SEQUENCE LISTING

<160> NUMBER OF SEQ ID NOS: 274

<210> SEQ ID NO 1
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 1
gtcctggccc gtctcagatt tccaatgcag ctgtccagac cactccaccc          50

<210> SEQ ID NO 2
<211> LENGTH: 50
<212> TYPE: DNA

```
<213> ORGANISM: Artificial Sequence
<220> FEATURE:
<223> OTHER INFORMATION: Synthetic Sequence

<400> SEQUENCE: 2
aaagaatcct gaataaatgg ggactttctg ttggtggaaa gaaatataga                50

<210> SEQ ID NO 3
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 3
tccaactcct gaaggccaca tgactcctga tcattttatc caaggacaca                50

<210> SEQ ID NO 4
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 4
attcagtcta caagtgccag gggtctactg tatcctcttt tccgtcttaa                50

<210> SEQ ID NO 5
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 5
aggccttatt taggtttgac caattgtccc aataattcct ttatggcaaa                50

<210> SEQ ID NO 6
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 6
tgagttccaa gagctcagag ggatctgcac ataatgtggc ttaccctgga                50

<210> SEQ ID NO 7
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 7
agagcaggtt acaagataat atataaagca caatcccatc ttagtttgga                50

<210> SEQ ID NO 8
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 8
cgcatacgca tgactacatt acaacgggcc aggaagattc aaagtttggt                50
```

<210> SEQ ID NO 9
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 9
aaccagaaca tgcagccact ttatgttctc caaactcttc caaatggagt          50

<210> SEQ ID NO 10
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 10
acagtcactt ggatggatct tcatcttcag aaatgaagca gtccagtgct          50

<210> SEQ ID NO 11
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 11
agttctacac ccagtgtgat ggagacaaat acttcagtat tgggacccat          50

<210> SEQ ID NO 12
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 12
aaatattgcg gtattcggtc actaaaggat ttgcagcttg cggcggaatc          50

<210> SEQ ID NO 13
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 13
ccacctcaca tcagggtctg tgtctggctt ggcatccagt tcctctgtct          50

<210> SEQ ID NO 14
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 14
gaacgaacag actcaggcga tgtgctttat ggcaggcgca aactcgattt          50

<210> SEQ ID NO 15
<211> LENGTH: 50
<212> TYPE: DNA
<213> ORGANISM: Artificial Sequence
<220> FEATURE:
<223> OTHER INFORMATION: Synthetic Sequence

```
<400> SEQUENCE: 15
ccacaggatc agagtggact ttaaggtaaa ggtgttcagt gatcataaag              50

<210> SEQ ID NO 16
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 16
aggcatcctg cttctttgta ccccaggaag tacataaatg attgatctgg              50

<210> SEQ ID NO 17
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 17
agtctgtttt gttggtattt agcaggtact attccctgtt taaaccagct              50

<210> SEQ ID NO 18
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 18
cctgtagtcc cagctactca ggagagtgag ccaggagaat ggcgtgaacc              50

<210> SEQ ID NO 19
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 19
tcctacatcc tttacagttc ttaaattcct ggcagatacc tctttggctt              50

<210> SEQ ID NO 20
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 20
tggagtgtaa taagtgccga aacagctatc accctgagtg cctgggacca              50

<210> SEQ ID NO 21
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 21
aaatcaccct tccctgtatt cactattttt atttattatg gataaagaga              50

<210> SEQ ID NO 22
<211> LENGTH: 50
<212> TYPE: DNA
```

```
<213> ORGANISM: Artificial Sequence
<220> FEATURE:
<223> OTHER INFORMATION: Synthetic Sequence

<400> SEQUENCE: 22
actctaggaa taatgtttcc tcagtctcca ccaccgggac cgctactgat            50

<210> SEQ ID NO 23
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 23
ctccatcctc tccatcttct ggacagcggt cagcaagccc ttcagtgccg            50

<210> SEQ ID NO 24
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 24
aggacagaaa cctaatgctt ccagatggcc ccaaacctca ggaggatggc            50

<210> SEQ ID NO 25
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 25
aagcactgat gtctcaaaca gcatttgaaa gcaggaaatg tatgatttga            50

<210> SEQ ID NO 26
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 26
aatcccatct ctcttaaatt cagtctttat tagagttctg atctttctgt            50

<210> SEQ ID NO 27
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 27
tgggcctgaa tccaaacagg ccaccactcc agcttccagg aagtcaagca            50

<210> SEQ ID NO 28
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 28
ttcgatcctc gtcaggtgca ggtcagcacg ttgctgtcga ttaagaccgg            50
```

<210> SEQ ID NO 29
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 29
agaaaatcca agctaggttg aaatctgaat gttgagcagt cagtgagaca        50

<210> SEQ ID NO 30
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 30
tgtaccacct ttacaatgag gaaggaaaaa gtagcacaat tttaaatagg        50

<210> SEQ ID NO 31
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 31
tgccagtaaa tgtgaaatgg ggtactaagt aataggtgtt gggtgaaggt        50

<210> SEQ ID NO 32
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 32
actgcactcc taaagcatga ccagtgcttg ataaactctc ctccatgcga        50

<210> SEQ ID NO 33
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 33
agaaatcacc gattgccctt gtcaactcag tcaaccctta ccgcattgaa        50

<210> SEQ ID NO 34
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 34
ggagtcccac tgtccccagc cagaatccca gtagactagc tgttatctca        50

<210> SEQ ID NO 35
<211> LENGTH: 50
<212> TYPE: DNA
<213> ORGANISM: Artificial Sequence
<220> FEATURE:
<223> OTHER INFORMATION: Synthetic Sequence

```
<400> SEQUENCE: 35
actgagtgcc tttggcagga aataaatcta tctcaatgcg ttaattggga        50

<210> SEQ ID NO 36
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 36
attaagagtg tggttggatt atgggtgacc tttatttgtt tctctggttt        50

<210> SEQ ID NO 37
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 37
tttccgtctt aatacagtgc tttgcaccca tatatatgcc acccacagga        50

<210> SEQ ID NO 38
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 38
tggaaagatg tccatgacat atcactgagt gaaagagca ggttacaaga         50

<210> SEQ ID NO 39
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 39
cccacatgtt ctagcctagg aatctgctta ttctaaaggc catttggcgt        50

<210> SEQ ID NO 40
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 40
gccacagcgg caggcacatc aacaataagc caggatacta gccacctcac        50

<210> SEQ ID NO 41
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 41
tggaaaggac aaaccagacc ttacaactgt ttcgtatatt acagaaaacg        50

<210> SEQ ID NO 42
<211> LENGTH: 50
<212> TYPE: DNA
```

-continued

<213> ORGANISM: Artificial Sequence
<220> FEATURE:
<223> OTHER INFORMATION: Synthetic Sequence

<400> SEQUENCE: 42
tttccactgg tattaccact ttagtactct gaatctcccg caatgtccaa            50

<210> SEQ ID NO 43
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 43
cccaggtatc caactttacc cagacggtag acgctcctaa tagcatggga            50

<210> SEQ ID NO 44
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 44
ggtgacaact ggtgaggaag gaaacttgaa gccagagttt atggatgagg            50

<210> SEQ ID NO 45
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 45
cagtctccac caccgggacc gctactgatc ttgaatcaag tgccaaagta            50

<210> SEQ ID NO 46
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 46
tgccccaaag aaaagcagta gtgagcctcc tccacgaaag cccgtcgagg            50

<210> SEQ ID NO 47
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 47
accggcaccc ctgttaccac agagtgtggg aggaactgct gccacagcgg            50

<210> SEQ ID NO 48
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 48
tcagcctctg aaaatccagg agatggtcca gtggcccaac caagccccaa            50

```
<210> SEQ ID NO 49
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 49
agcaggaaat gtatgatttg aagtcttcag ttcaagaaaa tcagctctct          50

<210> SEQ ID NO 50
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 50
agctcctgaa atcagattca gacaataaca acagtgatga ctgtgggaat          50

<210> SEQ ID NO 51
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 51
ctagagaact gaatgttagt aaaatcggct cctttgctga accctcttca          50

<210> SEQ ID NO 52
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 52
tgtctcggca ttaatccgtt tatgtgatgt gtattccatt ccgctcgcca          50

<210> SEQ ID NO 53
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 53
gatcgaaccg ggccgttctc tcgtgggaga cgcaggcaca actctttata          50

<210> SEQ ID NO 54
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 54
acctccggtc aataagcagg agaatgcagg cactttgaac atcctcagca          50

<210> SEQ ID NO 55
<211> LENGTH: 50
<212> TYPE: DNA
<213> ORGANISM: Artificial Sequence
<220> FEATURE:
<223> OTHER INFORMATION: Synthetic Sequence
```

<400> SEQUENCE: 55
caacatggtc atttagaaat cggaggtgtg gatgctctct atttagcgga     50

<210> SEQ ID NO 56
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 56
tgtatatcaa agcctcttca tctataagga gctcttacca attaataaga     50

<210> SEQ ID NO 57
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 57
tttacttagt ctgtctttag catttaattg ggtgtaatca gttgcctatt     50

<210> SEQ ID NO 58
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 58
ccctacaagt agtgcgtcag ttccaggaca cgtcacctta accaacccaa     50

<210> SEQ ID NO 59
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 59
gaaataaata catgttgggt ggcaggggga ggtgaaggga gggtgtctgt     50

<210> SEQ ID NO 60
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 60
tttaatacat gaacagcctt tgccaatcgt gggtgaaatg acgttgccga     50

<210> SEQ ID NO 61
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 61
gcagattcag tagcagatgc cgttcaaaag gtcgatttaa gtagaagtgc     50

<210> SEQ ID NO 62
<211> LENGTH: 50
<212> TYPE: DNA

<213> ORGANISM: Artificial Sequence
<220> FEATURE:
<223> OTHER INFORMATION: Synthetic Sequence

<400> SEQUENCE: 62
aacttcaagt ttaggcttttt agctgggcac ggtggctcac gctggtaatc          50

<210> SEQ ID NO 63
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 63
agcagacgaa cactatcagc ttcagcatgt gaaccagctc cttgccagca          50

<210> SEQ ID NO 64
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 64
cagcagttca agaccagcct gggcaacata gcaagaccct gtctttattt          50

<210> SEQ ID NO 65
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 65
aaacccttac tgccggtgag gctgaaacgc tgatgaatat gatgatggca          50

<210> SEQ ID NO 66
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 66
aaggattgct acccatgtct catcaccagc acttacattc cttccctgca          50

<210> SEQ ID NO 67
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 67 gcccttttctt cacaggtcag tcagtactaa agtagtcgtt gccagcatct          50

<210> SEQ ID NO 68
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 68
tcaggaggct gagatagaag gattgtcttg agcccaggaa ttcaaggctg          50

```
<210> SEQ ID NO 69
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 69
agtctgttag atttggggtc acttaatact tcatctcacc gaactgtccc         50

<210> SEQ ID NO 70
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 70
ggaaaccaag gatgactgtg cttagagtat tgctttcttt cttgatttgt         50

<210> SEQ ID NO 71
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 71
ctctccacag gaggattgtg aagcagaaaa tgtgtgggag atgggaggct         50

<210> SEQ ID NO 72
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 72
cctgaaggcc acatgactcc tgatcatttt atccaaggac acatggatgc         50

<210> SEQ ID NO 73
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 73
gcattggctc caggcgtcac agtacctctt ccttatcacc ccagcggtcc         50

<210> SEQ ID NO 74
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 74
acaaatggaa aggacaaacc agaccttaca actgtttcgt atattacaga         50

<210> SEQ ID NO 75
<211> LENGTH: 50
<212> TYPE: DNA
<213> ORGANISM: Artificial Sequence
<220> FEATURE:
<223> OTHER INFORMATION: Synthetic Sequence
```

<210> SEQ ID NO 76
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 75
cgcaagaggg cagaccgata gaatcattgg taatgagcgc cggattacgc          50

<210> SEQ ID NO 76
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 76
actatcagaa tcttccagta caggacagaa acctaatgct tccagatggc          50

<210> SEQ ID NO 77
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 77
gcagtgagcc gagattgcat cattgcactc tagcctggac aacagagcta          50

<210> SEQ ID NO 78
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 78
cactagaaca gtgatttctt caggtggaga ggaacgactg gcatcccata          50

<210> SEQ ID NO 79
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 79
ttgactcctg agtatatggg ccaacgacca tgtaacaatg tttcttctga          50

<210> SEQ ID NO 80
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 80
gagctaccat ctgatctgtc tgtcttgacc acccggagtc ccactgtccc          50

<210> SEQ ID NO 81
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 81
tgtttctctg ccatttctca gggatgtatt ctattttgta gggaaaagcc          50

<210> SEQ ID NO 82
<211> LENGTH: 50
<212> TYPE: DNA

<210> SEQ ID NO 83
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 82
ttctgatcta aattctttat agttgtacat agcaatctca cagggttcct        50

<210> SEQ ID NO 83
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 83
agcaggtggg tttagcgctg ggagagcttt ggacagtgtt gttaggtcac        50

<210> SEQ ID NO 84
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 84
tcccacacct ccatttgaga gggcaaagga atgatcgaga ccaacacaca        50

<210> SEQ ID NO 85
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 85
agtgatgact gtgggaatat cctgccttca gacattatgg actttgtact        50

<210> SEQ ID NO 86
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 86
tgccagtgga ctactaaaac ccaaagtata taagaagggt atggttgatt        50

<210> SEQ ID NO 87
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 87
gcctcagcca cctactacag gaccgccaag aaagaagtt cccaaaacca        50

<210> SEQ ID NO 88
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 88
gatggtgttg atgatgggac agagagtgat actagtgtca cagccacaac        50

-continued

<210> SEQ ID NO 89
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 89
aaaggtgagg agagatttgt ttctctgcca tttctcaggg atgtattcta    50

<210> SEQ ID NO 90
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 90
gggatcaaag tctgttctgg cggcattgtg ggcttaggcg aaacggtaaa    50

<210> SEQ ID NO 91
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 91
tggaaggatt cacaccaaaa tattaagagt gtggttggat tatgggtgac    50

<210> SEQ ID NO 92
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 92
acccgaaagt ccatctatag ggagcatggg ttaaaataag catagggcat    50

<210> SEQ ID NO 93
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 93
agagcaaggt catggcaaca atcaggattt aactaggaac agtagcaccc    50

<210> SEQ ID NO 94
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 94
cgccaatgct tgttcaggca cgccagaagg atgccgcaga ccattatctg    50

<210> SEQ ID NO 95
<211> LENGTH: 50
<212> TYPE: DNA
<213> ORGANISM: Artificial Sequence
<220> FEATURE:
<223> OTHER INFORMATION: Synthetic Sequence

```
<400> SEQUENCE: 95
tcaggtggag aggaacgact ggcatcccat aatttatttc gggaggagga           50

<210> SEQ ID NO 96
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 96
actgctgcaa taacagcggc atctagcatc tgtgtgctcc cctccactca           50

<210> SEQ ID NO 97
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 97
ttcctatcca tcctgaggag tatcagagga agtaattcct tcacatggaa           50

<210> SEQ ID NO 98
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 98
tcccatgttc ttactatagt ttgtgtattg ccaagtctgt tgtgagccct           50

<210> SEQ ID NO 99
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 99
cgtttgatga tgtattgatt ccaggggcca tgcaggagct tgaagcactc           50

<210> SEQ ID NO 100
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 100
tttttggagt atgtaccacc tttacaatga ggaaggaaaa agtagcacaa           50

<210> SEQ ID NO 101
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 101
ctatgaattg aacaactagg tgagcctttt aatagtccgt gtctgagatt           50

<210> SEQ ID NO 102
<211> LENGTH: 50
<212> TYPE: DNA
```

<210> SEQ ID NO 102
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 102
tgagtgtcaa agactttaaa taaagaaaat gctactacca aaggtgttga            50

<210> SEQ ID NO 103
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 103
gaagtatgtg cccaattcta ctgatagtcc tggcccgtct cagatttcca            50

<210> SEQ ID NO 104
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 104
gggcttaccc cactctatgg agtaagatcc tatggtgaag aagacattcc            50

<210> SEQ ID NO 105
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 105
agaatccagc cagaggacag acctcagtac cacagtagcc actccatcct            50

<210> SEQ ID NO 106
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 106
accttgaagc tatctggaat gagcaacaga tcatccatta tcaacgaaca            50

<210> SEQ ID NO 107
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 107
ccggttgtgg tagtgggtgc ttggtaatcc tagctacttg ggaggctgag            50

<210> SEQ ID NO 108
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 108
atgtcacact aatttatgc ttttcatcct tattttccat ccaaagttgt             50

```
<210> SEQ ID NO 109
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 109
cccaacatca taaaaagatc taaatctagc atcatgtatt ttgaaccggc          50

<210> SEQ ID NO 110
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 110
cgaacgtcat caggcgtggc aggcggtgga cgagcgtccg catgctaatc          50

<210> SEQ ID NO 111
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 111
tgggcctctg tatcagtggg ttctgtatcc ctggactcaa ccaaccttgg          50

<210> SEQ ID NO 112
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 112
ccctcaccca aattccctaa gtgttaatat gtttctctgt gtgtatatat          50

<210> SEQ ID NO 113
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 113
cactttggga agccgaagca ggcagatcac ttgaggtcag gagttggaga          50

<210> SEQ ID NO 114
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 114
aagtacccct cacccaaatt ccctaagtgt taatatgttt ctctgtgtgt          50

<210> SEQ ID NO 115
<211> LENGTH: 50
<212> TYPE: DNA
<213> ORGANISM: Artificial Sequence
<220> FEATURE:
<223> OTHER INFORMATION: Synthetic Sequence
```

<400> SEQUENCE: 115
aaacacttcc acctcttcaa atttgcaaag gacagtggtt actgtaggca          50

<210> SEQ ID NO 116
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 116
attccattct acagcagctc aactgggaag aagcgaggca agagatcagc          50

<210> SEQ ID NO 117
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 117
agcacaaagt ttcccatttg cggaccagtt cttctgaagc acacattcca          50

<210> SEQ ID NO 118
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 118
taacttcaca ccctcccagc ttcctaatca tccaagtctg ttagatttgg          50

<210> SEQ ID NO 119
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 119
accaccagaa tcaggtgagt gaggagggca agaaggaatt gctgacccac          50

<210> SEQ ID NO 120
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 120
ccctttcttc acaggtcagt cagtactaaa gtagtcgttg ccagcatctg          50

<210> SEQ ID NO 121
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 121
tggaaacaac ccgaaagtcc atctataggg agcatgggtt aaaataagca          50

<210> SEQ ID NO 122
<211> LENGTH: 50
<212> TYPE: DNA

<213> ORGANISM: Artificial Sequence
<220> FEATURE:
<223> OTHER INFORMATION: Synthetic Sequence

<400> SEQUENCE: 122
tgtgaaggca aatagggtgt gattttgttc tatattcatc ttttgtctcc                50

<210> SEQ ID NO 123
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 123
tcagaactcc tgaatcttgg tgaaggattg ggtcttgaca gtaatcgtga                50

<210> SEQ ID NO 124
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 124
ggcagaacga acaccacatt ttgaccttgt aggggccata gaccatacat                50

<210> SEQ ID NO 125
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 125
aaactatcca gcaacatttg ggccagctaa acatgcttca tcgtcggtcc                50

<210> SEQ ID NO 126
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 126
tgcctacaac agaacctgtg gatagtagtg tctcttcctc tatctcagca                50

<210> SEQ ID NO 127
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 127
tgatcaggca attcggtcaa ttgtcactgt catcagaatc tgtcggccaa                50

<210> SEQ ID NO 128
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 128
ctgcaataac agcggcatct agcatctgtg tgctcccctc cactcagact                50

<210> SEQ ID NO 129
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 129
gcaatcctcc ttcaggcctg cttattgggg ttcagcctcc tccggatccc            50

<210> SEQ ID NO 130
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 130
tgccatttga agttattact agcaaaatta caaattattg cctactattc            50

<210> SEQ ID NO 131
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 131
acaacttatt gttctaagtg cagaagttca gatatcattg agactgagaa            50

<210> SEQ ID NO 132
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 132
cactatgaat tgaacaacta ggtgagcctt ttaatagtcc gtgtctgaga            50

<210> SEQ ID NO 133
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 133
ctaaggatga ctctggtcag agatacctgg cctggtctgg acacagtgcc            50

<210> SEQ ID NO 134
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 134
tccttggaag ctcagctcag ctcattggag tcaagccgca gagtccacac            50

<210> SEQ ID NO 135
<211> LENGTH: 50
<212> TYPE: DNA
<213> ORGANISM: Artificial Sequence
<220> FEATURE:
<223> OTHER INFORMATION: Synthetic Sequence

```
<400> SEQUENCE: 135
gcctctgtat cagtgggttc tgtatccctg gactcaacca accttggatt            50

<210> SEQ ID NO 136
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 136
tgttatatgc aaatgctgca ccatttgtc tagggacttg ggcatccatg             50

<210> SEQ ID NO 137
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 137
tcccatagct ctttgtttat accactctta ggtcacttag catgttctgt            50

<210> SEQ ID NO 138
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 138
acctgaagat gctggggaga aagaacatgt cactaagagt tctgttggcc            50

<210> SEQ ID NO 139
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 139
gtgcgtcagt tccaggacac gtcaccttaa ccaacccaag gttgcttggt            50

<210> SEQ ID NO 140
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 140
agggtggttt gctttctctg tgccagtagt gggcatgtag aggtaaggca            50

<210> SEQ ID NO 141
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 141
ttatagagaa ccaccatgtg actattggac ttatgtaact tgtattacaa            50

<210> SEQ ID NO 142
<211> LENGTH: 50
<212> TYPE: DNA
```

```
<213> ORGANISM: Artificial Sequence
<220> FEATURE:
<223> OTHER INFORMATION: Synthetic Sequence

<400> SEQUENCE: 142
agaccaacac acagattcta cccaatcagc aaactcctct ccagatgaag         50

<210> SEQ ID NO 143
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 143
ctcactgaag gaaggaacgg agctggcgtt agagacgatt acaagcggag         50

<210> SEQ ID NO 144
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 144
ccggtgatac tggtagttgg tgtgaaactc ggctgtatta atcacgcgat         50

<210> SEQ ID NO 145
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 145
ccctcattac taggaaatca tctcaggaga gaaattaaat ctataaatgg         50

<210> SEQ ID NO 146
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 146
tggaacagag aacttaaaga ttgatagacc tgaagatgct ggggagaaag         50

<210> SEQ ID NO 147
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 147
aggagatcga gaccatcctg gctaacacgg tgaaaccctg tctctactaa         50

<210> SEQ ID NO 148
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 148
tgagaacaag ttggagacat aaaccatttt acctctaaat attttagtgt         50
```

```
<210> SEQ ID NO 149
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 149
tgtcgtcgct gcaaattctg tcacgtttgt ggagggcaac atcaggctac            50

<210> SEQ ID NO 150
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 150
aggaattaca ggcaccacgg aaacgcacag tcaaagtgac actgacacct            50

<210> SEQ ID NO 151
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 151
agtcagtgag acacaaacta gctaagaaag tcaaccctgc ccacttgcca            50

<210> SEQ ID NO 152
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 152
tgcattatta tctgttgcaa atgtgaaggc aaatagggtg tgattttgtt            50

<210> SEQ ID NO 153
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 153
tacagataac ctgatctacc aagtggctaa acggaccgca gatttgtacg            50

<210> SEQ ID NO 154
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 154
aaacttgctc cctctagtac cccttcaaac attgcccctt ctgatgtggt            50

<210> SEQ ID NO 155
<211> LENGTH: 50
<212> TYPE: DNA
<213> ORGANISM: Artificial Sequence
<220> FEATURE:
<223> OTHER INFORMATION: Synthetic Sequence
```

<400> SEQUENCE: 155
actccatcca tgcaggcttt gggtgagagc ccagagtcat cttcatcaga           50

<210> SEQ ID NO 156
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 156
aagtgctgac aagagacgcg agagacgtgc ttccgaagga gtttccatat           50

<210> SEQ ID NO 157
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 157
accagctaaa gaaatgtttt gaagtatttt agagatttta ggaaggaatc           50

<210> SEQ ID NO 158
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 158
aaacagttaa attggaggta ttgttttaat ttcctgttcg aagcctagag           50

<210> SEQ ID NO 159
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 159
gcacttcaaa cacttatgga tataattaga taaattggca aatctgtaga           50

<210> SEQ ID NO 160
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 160
aagtctgggt gagttataca catgatgctc ttttatagag aaccaccatg           50

<210> SEQ ID NO 161
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 161
ttcttttcta gatctgtacc aagtgtgttc gctgtaagag ctgtggatcc           50

<210> SEQ ID NO 162
<211> LENGTH: 50
<212> TYPE: DNA

```
<213> ORGANISM: Artificial Sequence
<220> FEATURE:
<223> OTHER INFORMATION: Synthetic Sequence

<400> SEQUENCE: 162
acctcagtac cacagtagcc actccatcct ctggactcaa gaaaagaccc              50

<210> SEQ ID NO 163
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 163
cactttgcac tggaacttac aacacccgag caaggacgcg actctcccga              50

<210> SEQ ID NO 164
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 164
gacacttccc cgccgctgcc aggacccgct tctctgaaag gctctccttg              50

<210> SEQ ID NO 165
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 165
ccagccagcg gtccgcaacc cttgccgcat ccacgaaact tgcccatag              50

<210> SEQ ID NO 166
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 166
ctttgcactg gaacttacaa cacccgagca aggac                              35

<210> SEQ ID NO 167
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 167
caacccttgc cgcatccacg aaactttgcc catag                              35

<210> SEQ ID NO 168
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 168
ctcaacgtta gcttcaccaa caggaactat gacctcgact acgactcggt              50
```

```
<210> SEQ ID NO 169
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 169
ttagcttcac caacaggaac tatgacctcg actacgactc                              40

<210> SEQ ID NO 170
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 170
cgagaccttc atcaaaaaca tcatcatcca ggactgtatg                              40

<210> SEQ ID NO 171
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 171
gtatttctac tgcgacgagg aggagaactt ctaccagcag                              40

<210> SEQ ID NO 172
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 172
cgtttatagc agttacacag aatttcaatc ctagtatata gtacctagta                   50

<210> SEQ ID NO 173
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 173
gagactgaaa gatttagcca taatgtaaac tgcctcaaat tggactttgg                   50

<210> SEQ ID NO 174
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 174
ccttctaaca gaaatgtcct gagcaatcac ctatgaactt gtttcaaatg                   50

<210> SEQ ID NO 175
<211> LENGTH: 50
<212> TYPE: DNA
<213> ORGANISM: Artificial Sequence
<220> FEATURE:
<223> OTHER INFORMATION: Synthetic Sequence
```

<400> SEQUENCE: 175
ttacacaatg tttctctgta aatattgcca ttaaatgtaa ataactttaa          50

<210> SEQ ID NO 176
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 176
catctccgta ttgagtgcga agggaggtgc ccctattatt atttgacacc          50

<210> SEQ ID NO 177
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 177
gccactccag ccggcgagag aaagaagaaa agctggcaaa aggagtgttg          50

<210> SEQ ID NO 178
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 178
gtattgagtg cgaagggagg tgcccctatt attatttg          38

<210> SEQ ID NO 179
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 179
cttgtattta tggaggggtg ttaaagcccg cggctgag          38

<210> SEQ ID NO 180
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 180
aaaactttgt gccttggatt ttggcaaatt gttttcctca ccgccacctc          50

<210> SEQ ID NO 181
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 181
gagatagcag gggactgtcc aaaggggtg aaagggtgct ccctttattc          50

<210> SEQ ID NO 182
<211> LENGTH: 39
<212> TYPE: DNA

```
<213> ORGANISM: Artificial Sequence
<220> FEATURE:
<223> OTHER INFORMATION: Synthetic Sequence

<400> SEQUENCE: 182
aaaactttgt gccttggatt ttggcaaatt gttttcctc                    39

<210> SEQ ID NO 183
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 183
ggaatggttt ttaagactac cctttcgaga tttctgcctt atgaatatat          50

<210> SEQ ID NO 184
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 184
ttttatcact ttaatgctga gatgagtcga atgcctaaat agggtgtctt          50

<210> SEQ ID NO 185
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 185
ctcccattcc tgcgctattg acacttttct cagagtagtt atggtaactg          50

<210> SEQ ID NO 186
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 186
ttatcttaca actcaatcca cttcttctta cctcccgtta acattttaat          50

<210> SEQ ID NO 187
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 187
gatcttctca gcctattttg aacactgaaa agcaaatcct tgccaaagtt          50

<210> SEQ ID NO 188
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 188
tttcattggc agcttattta acgggccact cttattagga aggagagata          50
```

<210> SEQ ID NO 189
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 189
cattaagtct taggtaagaa ttggcatcaa tgtcctatcc tgggaagttg            50

<210> SEQ ID NO 190
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 190
catttccagt aaaataggga gttgctaaag tcataccaag caatttgcag            50

<210> SEQ ID NO 191
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 191
atcatttgca acacctgaag tgttcttggt aaagtccctc aaaaatagga            50

<210> SEQ ID NO 192
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 192
aatctggtaa ttgattattt taatgtaacc ttgctaaagg agtgatttct            50

<210> SEQ ID NO 193
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 193
gataattttg tccagagacc tttctaacgt attcatgcct tgtatttgta            50

<210> SEQ ID NO 194
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 194
gtctagaaaa acctgccaaa tatgatgaca tcaagaaggt ggtgaagcag            50

<210> SEQ ID NO 195
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 195
tacactgagc accaggtggt ctcctctgac ttcaacagcg acacccactc          50

<210> SEQ ID NO 196
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 196
ctggggctgg cattgccctc aacgaccact ttgtcaagct catttcctgg          50

<210> SEQ ID NO 197
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 197
cactgccaac gtgtcagtgg tggacctgac ctgccgtcta gaaaaacctg          50

<210> SEQ ID NO 198
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 198
aaatatgatg acatcaagaa ggtggtgaag caggcgtcgg agggcccct          50

<210> SEQ ID NO 199
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 199
cattgccctc aacgaccact ttgtcaagct catttcctg                     39

<210> SEQ ID NO 200
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 200
ctacactgag caccaggtgg tctcctctga cttcaacag                     39

<210> SEQ ID NO 201
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 201
tgatgctttt cctagattat tctctggtaa atcaaagaag tgggtttatg          50

<210> SEQ ID NO 202
<211> LENGTH: 50
<212> TYPE: DNA

```
<213> ORGANISM: Artificial Sequence
<220> FEATURE:
<223> OTHER INFORMATION: Synthetic Sequence

<400> SEQUENCE: 202
ctgtccagtt aatttctgac ctttactcct gcccttttgag tttgatgatg          50

<210> SEQ ID NO 203
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 203
tattctctgg taaatcaaag aagtgggttt atggaggtcc tcttgtgtcc          50

<210> SEQ ID NO 204
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 204
gatttctgga aaagagctag gaaggacagg caacttggca aatcaaagcc          50

<210> SEQ ID NO 205
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 205
caccgcaccc tggtctgagg ttaaatatag ctgctgacct ttctgtagct          50

<210> SEQ ID NO 206
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 206
gagaagctga gtcatgggta gttggaaaag gacatttcca ccgcaaaatg          50

<210> SEQ ID NO 207
<211> LENGTH: 42
<212> TYPE: DNA
<213> ORGANISM: Artificial Sequence
<220> FEATURE:
<223> OTHER INFORMATION: Synthetic Sequence

<400> SEQUENCE: 207
attattctct ggtaaatcaa agaagtgggt ttatggaggt cc                  42

<210> SEQ ID NO 208
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 208
ctgtccagtt aatttctgac ctttactcct gcccttttgag                    40
```

<210> SEQ ID NO 209
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 209
cctggtctga ggttaaatat agctgctgac ctttctgtag                40

<210> SEQ ID NO 210
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 210
gaaaagagct aggaaggaca ggcaacttgg caaatcaaag                40

<210> SEQ ID NO 211
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 211
gggagaagct gagtcatggg tagttggaaa aggacatttc                40

<210> SEQ ID NO 212
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 212
gaaagacaag gaaggaacac ctccacttac aaaagaagat aagacagttg     50

<210> SEQ ID NO 213
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 213
caaagtatgc caaagaaggt cttattcgca aaccaatatt tgataatttc     50

<210> SEQ ID NO 214
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 214
aaataacaca tggaaaggac atttcagagt taccaaaggg aaacaaagaa     50

<210> SEQ ID NO 215
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 215
gctgtcaaaa ccaaaatact tataaagaaa gggagaggaa atctggaaaa                50

<210> SEQ ID NO 216
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 216
ctcactctag aatatttgag tctgtaacct tgcctagtaa tcgaacttct                50

<210> SEQ ID NO 217
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 217
gtttatagag gatgaggatt atgaccctcc aattaaaatt gcccgattag                50

<210> SEQ ID NO 218
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 218
aaatgagagt aatgatagga gaagcagaag gtattcagtg tcggagagaa                50

<210> SEQ ID NO 219
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 219
gacacattac ataaactagg agaacttaag actacgaaca gaatatttgg                50

<210> SEQ ID NO 220
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 220
tgtgtatgaa ttccttcttt caagtgaact gatactagat ttatttaaga                50

<210> SEQ ID NO 221
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 221
cttaattata aagttggatg tcatttgaga aactctggga attggaagta                50

<210> SEQ ID NO 222
<211> LENGTH: 50
<212> TYPE: DNA

<213> ORGANISM: Artificial Sequence
<220> FEATURE:
<223> OTHER INFORMATION: Synthetic Sequence

<400> SEQUENCE: 222
taaataaatt cttattcagc tcctcgaagc aataattact ttccagtagg          50

<210> SEQ ID NO 223
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 223
ttaaaccgaa atcaggagta gttgtgtaaa gaacttattg gtaatgatgg          50

<210> SEQ ID NO 224
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 224
tgcttgtgga tacattgtaa caaatgctta taaatcattt ccaaactaat          50

<210> SEQ ID NO 225
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 225
ccaaggaaaa cagtaggtgt ggtatcaata taggaaacaa ataagtattt          50

<210> SEQ ID NO 226
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 226
taatcattaa gaaatactaa tttaagtatg gcaaaggaaa gcacaggtgc          50

<210> SEQ ID NO 227
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 227
tttctagcct attcaaatca atctggtcat ttatggtact ttcctattag          50

<210> SEQ ID NO 228
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 228
caataacagc atacatttct tgactggttg aatttcatta actatttggc          50

```
<210> SEQ ID NO 229
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 229
gcatttgtgt ttcttaggtg acagttgcta ggtagaattg aattaaatat        50

<210> SEQ ID NO 230
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 230
ttaacatttc tcaatatcag gcagagatca tatttaaaca gtttcaatct        50

<210> SEQ ID NO 231
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 231
ctgtgtattt gactgtgctt gggtatatta tacttttctt actgattgag        50

<210> SEQ ID NO 232
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 232
aaactgactt tatggagaga taaccctgtt tacctttaga aagaaggaag        50

<210> SEQ ID NO 233
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 233
aaaataaacc ctgtgattgt gatgcttaac ttaattttct acagtgaatc        50

<210> SEQ ID NO 234
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 234
gaataatttg ggacattgcc aggaatcaga atagtttact atctgaagta        50

<210> SEQ ID NO 235
<211> LENGTH: 50
<212> TYPE: DNA
<213> ORGANISM: Artificial Sequence
<220> FEATURE:
<223> OTHER INFORMATION: Synthetic Sequence
```

<400> SEQUENCE: 235
atgaaattga gggatagata cagtaagtga gttgtctaag attacatagt         50

<210> SEQ ID NO 236
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 236
gctttccaag tgatttcaca taaattattt attccttaca gtgctcaaat         50

<210> SEQ ID NO 237
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 237
attgtgataa gattttatat taattgtgct gttaggagtt ttggctgttt         50

<210> SEQ ID NO 238
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 238
tttcatgaga agtcattcag tatcattaag tatgctgatt tgtctccttt         50

<210> SEQ ID NO 239
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 239
agaaatttat ttggggttca gattcacatg ttgtaggtta gttatatact         50

<210> SEQ ID NO 240
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 240
ggatctcaaa tgtacagaaa tcacatctaa atgtcaattc ctgagttaag         50

<210> SEQ ID NO 241
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 241
ctgtatgttt ctgccattat acttatttgc ttacctgatt taaagttgtc         50

<210> SEQ ID NO 242
<211> LENGTH: 50
<212> TYPE: DNA

-continued

<213> ORGANISM: Artificial Sequence
<220> FEATURE:
<223> OTHER INFORMATION: Synthetic Sequence

<400> SEQUENCE: 242
tattaatcag tttgtttaaa tagaccatct ttcttgagaa cttgtgcaaa     50

<210> SEQ ID NO 243
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 243
gtatctatag tttgaaatta ggactatcct ctgtgtacta tgcaccaaag     50

<210> SEQ ID NO 244
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 244
tctgtaataa agctgtatgg ctgggtccat ttatttcaat attagttatt     50

<210> SEQ ID NO 245
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 245
ccaactataa ctgaaaatag gatgcttccc taagttttag taaaggattt     50

<210> SEQ ID NO 246
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 246
gtctttgaag aggagaattt cagccttttc ttaaatagtc caatacttta     50

<210> SEQ ID NO 247
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 247
attgttctgc ccccaacata     20

<210> SEQ ID NO 248
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 248
agaggcccag ctgtagttct     20

```
<210> SEQ ID NO 249
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 249
tccgtaagct cgaccctagt                                              20

<210> SEQ ID NO 250
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 250
gcgctcgttc tcctctaaac                                              20

<210> SEQ ID NO 251
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (11)...(16)
<223> OTHER INFORMATION: n = A, C, T, or G

<400> SEQUENCE: 251
ccgactcgag nnnnnnatgt gg                                           22

<210> SEQ ID NO 252
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 252
atagtttgtg tattgccaag tctgttg                                      27

<210> SEQ ID NO 253
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 253
ggcgctcgtt ctcctctaaa                                              20

<210> SEQ ID NO 254
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 254
accaccggga ccgctact                                                18

<210> SEQ ID NO 255
<211> LENGTH: 23
<212> TYPE: DNA
```

```
<213> ORGANISM: Artificial Sequence
<220> FEATURE:
<223> OTHER INFORMATION: Synthetic Sequence

<400> SEQUENCE: 255
gtggccctaa gacatgatca act                                              23

<210> SEQ ID NO 256
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 256
cccttccaca agtttt                                                      16

<210> SEQ ID NO 257
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 257
atcttgaatc aagtgccaaa                                                  20

<210> SEQ ID NO 258
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 258
actttctatt tccactggta ttaccacttt agtactctga atc                        43

<210> SEQ ID NO 259
<211> LENGTH: 44
<212> TYPE: DNA
<213> ORGANISM: Artificial Sequence
<220> FEATURE:
<223> OTHER INFORMATION: Synthetic Sequence

<400> SEQUENCE: 259
gaaagcatga agaataagtc acctgcactt cagaggccaa attt                       44

<210> SEQ ID NO 260
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 260
actttctatt tccactggta cttcagaggc caaattt                               37

<210> SEQ ID NO 261
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 261
gaaagcactt tagtactctg aatc                                             24
```

<210> SEQ ID NO 262
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 262
ataagggaca tatcctacat cctttacagt tcttaaattc c                41

<210> SEQ ID NO 263
<211> LENGTH: 57
<212> TYPE: DNA
<213> ORGANISM: Artificial Sequence
<220> FEATURE:
<223> OTHER INFORMATION: Synthetic Sequence

<400> SEQUENCE: 263
aggggatgtc aaatgtgatg ggatatgtca aggagggttt tattggactt gtttaaa    57

<210> SEQ ID NO 264
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 264
ataagggaca ttggacttgt ttaaa                25

<210> SEQ ID NO 265
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 265
aggggcagtt cttaaattcc                20

<210> SEQ ID NO 266
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 266
gattcagagt actaaagtgg taataccagt ggaaatagaa agt                43

<210> SEQ ID NO 267
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 267
aaatttggcc tctgaagtac cagtggaaat agaaagt                37

<210> SEQ ID NO 268
<211> LENGTH: 44
<212> TYPE: DNA
<213> ORGANISM: Artificial Sequence
<220> FEATURE:
<223> OTHER INFORMATION: Synthetic Sequence

```
<400> SEQUENCE: 268
aaatttggcc tctgaagtgc aggtgactta ttcttcatgc tttc                    44

<210> SEQ ID NO 269
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 269
gattcagagt actaaagtgc tttc                                          24

<210> SEQ ID NO 270
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 270
tttaaacaag tccaatgtcc cttat                                         25

<210> SEQ ID NO 271
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 271
ggaatttaag aactgcccct                                               20

<210> SEQ ID NO 272
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 272
ggaatttaag aactgtaaag gatgtaggat atgtcccttate t                     41

<210> SEQ ID NO 273
<211> LENGTH: 57
<212> TYPE: DNA
<213> ORGANISM: Artificial Sequence
<220> FEATURE:
<223> OTHER INFORMATION: Synthetic Sequence

<400> SEQUENCE: 273
tttaaacaag tccaataaaa ccctccttga catatcccat cacatttgac atcccct      57

<210> SEQ ID NO 274
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 274
ggaatttaag aacatcccct                                               20
```